United States Patent [19]
Amara et al.

[11] Patent Number: 6,074,828
[45] Date of Patent: Jun. 13, 2000

[54] AMINO ACID TRANSPORTERS AND USES

[75] Inventors: Susan G. Amara; Jeffrey L. Arriza, both of Portland, Oreg.

[73] Assignee: Oregon Health Sciences University, Portland, Oreg.

[21] Appl. No.: 09/042,913

[22] Filed: Mar. 17, 1998

Related U.S. Application Data

[62] Division of application No. 08/546,666, Oct. 23, 1995, Pat. No. 5,776,774, which is a division of application No. 08/140,729, Oct. 20, 1993, Pat. No. 5,658,782.

[51] Int. Cl.$^7$ .......................... C12Q 1/68; G01N 33/53; G01N 33/566; C12P 21/04
[52] U.S. Cl. ................................. 435/6; 435/7.8; 435/29; 435/69.1; 435/70.1; 436/501; 436/504
[58] Field of Search .................... 435/6, 7.8, 29, 435/69.1, 70.1; 436/501, 504

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,385,831 | 1/1995 | Mulvihill et al. | 435/69.1 |
| 5,424,185 | 6/1995 | Lam et al. | 435/6 |

OTHER PUBLICATIONS

Arriza et al. (1994) J. Neurosci., vol. 14, No. 9, pp. 5559–5569.
Kanai et al. (1992) Nature, 360: 466–471.
Kanai et al. (1993) Trends in Neurosci., vol. 16, No. 9, pp. 365–370.
Kanai et al., (1993) FASEB J., 7: 1450–1459.
Kanner, (1993), FEBS Lett., 325 (1,2): pp. 95–99.
Pines et al., (1992) Nature, 360: pp. 464–467.
Schloss et al. (1992) FEBS Lett., 307 (1): pp. 76–80.
Shashidharan et al., (1993), Biochim. Biophys. Acta., 1216: pp. 161–164.
Stelzner et al., (1993) FASEB J., 7(4/part 2): A575.
Storck et al., (1992), Proc. Natl. Acad. Sci., 89; pp. 10955–10959.
Uhl, (1992), Trends in Neurosci., 15(7): 265–268.
Anderson et al., (1989) J. Biol. Chem., 264: p. 8222–822.
Arriza et al., (1992) J. Neurosci., 12: 4045–4055.
Barish, (1983) J. Physiol., 342: 309–325.
Bertling et al., (1987) Bioscience Reports, 7: 107–112.
Blakely et al., (1991) Anal. Biochem., 194: 302–308.
Bouvier et al., (1992) Nature, 360: 471–474.
Bussolati et al., (1992) J.Biol. Chem., 267: 8330–8335.
Choi et al., (1987) Neurosci., 7: 357–358.
Chomczynski & Sacchi, (1987) Anal. Biochem., 162: 156–159.
Christensen (1990), Physiol. Rev., 70: 43: 77.
Christensen et al., (1967), J. Biol. Chem., 242: 5237–5246.
Eisenberg et al., (1984), J. Molec. Biol., 179: 125–142.
Engelke et al., (1992) J. Bacteriol., 171: 5551–5560.
Fairman, (1995) Human Excitatory Amino Acid Transporter 4, Genbank Accession No. U18244.
Felgner et al., (1987) Proc. Natl. Acad. Sci., 84: 7412–7417.
Georgiou, (1988) AICHE Journal, vol. 34, No. 8, pp. 1233–1248.
Gluzman, (1981) Cell, 23: 175–182.
Guastella et al., (1992) Proc. Natl. Sci., 89: 7189–7193.
Guastella et al., (1990) Science, 249: 1303–1306.
Kanai et al., (1994) J. Biol. Chem., vol. 269, No. 32, pp. 20599–20606.
Kanner & Schuldiner, (1987), CRC Crit. Rev. Biochem., 22: 1–38.
Kavanaugh et al., (1992) J. Biol. Chem., 267: 22007–22009.
Kim et al., (1991) Nature, 352: 725–728.
Kong et al., (1993) J. Biol. Chem., 268: 1509–1512.
Kozak, (1987) Nucleic Acid Res., 15: 8125–8132.
Maenz et al., (1992), J. Biol. Chem., 267: 1510–1516.
Makowske & Christensen, (1982) J. Biol. Chem., 257: 14635–14638.
Nicholls & Atwell, (1990), TIPS, 11: 462–468.
Olney et al., (1990) Science, 248: 596–599.
Quick and Lester, (1994) Methods in Neuroscience, 19: 261–279.
Saiki et al., (1988) Science, 239: 487–491.
Sanger et al., (1977) Proc. Natl. Acad. Sci., 74: 5463.
Smith & Johnson, (1988) Gene, 67: 31–40.
Smithies et al., (1985) Nature, 317: 230–234.
Thomas & Capecchi, (1987) Cell, 51: 503–512.
Wallace et al., (1990) J. Bacteriol., 172: 3214–3220.
Wang et al., (1991) Nature, 352: 729–731.
Dreyer et al., (1996) Arch. Ophthalmol., 114: 299–305.
Honda, (1996) Nippon Ganka Gakkst Zasshi, 100: 937–955.
Kalloniatis, (1995) J. Amer. Optom. Assoc., 66: 750–757.
Zerangue et al., (1995) J. Biol. Chem., 270: 6433–6435.
Kataoka et al., (1997) J. Neurosci., 17: 7017–7024.
Sheng et al., (1996) Neuron., 17: 575–578.

*Primary Examiner*—Lisa Hobbs
*Attorney, Agent, or Firm*—McDonnell Boehnen Hulbert & Berghoff

[57] ABSTRACT

The present invention relates to novel mammalian amino acid transporter proteins and the genes that encode such proteins. The invention is directed toward the isolation, characterization and pharmacological use of the human amino acid transporter proteins EAAT1, EAAT2, EAAT3 and ASCT1. The invention specifically provides isolated complementary DNA copies of mRNA corresponding to each of these transporter genes. Also provided are recombinant expression constructs capable of expressing each of the amino acid transporter genes of the invention in cultures of transformed prokaryotic and eukaryotic cells, as well as such cultures of transformed cells that synthesize the human amino acid transporter proteins encoded therein. The invention also provides methods for screening in vitro compounds having transport-modulating properties using preparations of transporter proteins from such cultures of cells transformed with recombinant expression constructs.

11 Claims, 42 Drawing Sheets

FIG. 1A

```
CACCTCTAGC  TCGGAGCGGC  GTGTAGCGCC

ATG  GAG  AAG  AGC  AAC  GAG  ACC  AAC                          54
                                    Met  Glu  Lys  Ser  Asn  Glu  Thr  Asn
                                     1                 5

GGC  TAC  CTT  GAC  AGC  GCT  CAG  GCG  GGG  CCT  GCC  GGG  CCC  GGA  GCT        102
Gly  Tyr  Leu  Asp  Ser  Ala  Gln  Ala  Gly  Pro  Ala  Gly  Pro  Gly  Ala
     10                    15                    20

CCG  GGG  ACC  GCG  GCA  GGA  CGC  TGC  CGT  CGG              150
Pro  Gly  Thr  Ala  Ala  Gly  Arg  Cys  Arg  Arg  Arg  Ala  Gly  Leu  Arg
 25                    30                    35                    40

CGC  CAA  GCG  CTG  GTG  CTC  CTG  TCC  GGG  GCG  GCG  CTG  GGC  GCG        198
Arg  Gln  Ala  Leu  Val  Leu  Leu  Ser  Gly  Ala  Ala  Leu  Gly  Ala
                45                    50                    55

GGC  CTG  GGC  GCG  GCA  AGC  CTG  CTG  CGC  ACG  CAG  GTC        246
Gly  Leu  Gly  Ala  Ala  Ser  Leu  Leu  Arg  Thr  Gln  Val
                60                    65                    70

ACC  TAC  CTG  GCC  TTC  CCC  GGG  GAG  CTC  CTC  CGC  ATG  ATG        294
Thr  Tyr  Leu  Ala  Phe  Pro  Gly  Glu  Leu  Leu  Arg  Arg  Met  Met
                75                    80                    85

ATC  ATC  CTG  CCG  GTG  GTC  TGC  AGC  CTG  GTG  TCG  GCC  TCG        342
Ile  Ile  Leu  Pro  Leu  Val  Cys  Ser  Val  Leu  Ala  Ala  Ser
                90                    95                   100
```

FIG. 1B

```
CTC GAT GCC AGC TGC CTC GGG CGT CTG GGC ATC CGT GTC GCC TAC          390
Leu Asp Ala Ser Cys Leu Gly Arg Leu Gly Ile Arg Val Ala Tyr
105             TGC Cys 110         CTG GGC Gly 115         120

TTT GGC CTC ACC ACA CTG AGT GCC GGC GCG TCG GCG GTG GCC TTG          438
Phe Gly Leu Thr Thr Leu Ser Ala Gly Ala Ser Ala Val Ala Leu
                125                     130                 135

TTC ATC AAG CTG GGA CCA TCC GGT GCG CAG CTT ACC GCC AGC GAC          486
Phe Ile Lys Leu Gly Pro Ser Gly Ala Gln Leu Thr Ala Ser Asp
        140                 145                     150

CTG GGG TCG CCT GTC CCC TTT AAA TAT AAA CCC CCT TCC GAG ACG GTG      534
Leu Gly Ser Pro Val Pro Phe Lys Tyr Lys Pro Pro Ser Glu Thr Val
                                165

GAC TCT CTC TTC CTC GAC CTG CCC GCC TAT CCT TCC AAT CTT GTG          582
Asp Ser Leu Phe Leu Asp Leu Pro Ala Tyr Pro Ser Asn Leu Val
                                175             180

GTT GCA GCT TCT CGT AAT ACG GAT TAT AAG ATC CCC GTC ACC CAG          630
Val Ala Ala Ser Arg Asn Thr Asp Tyr Lys Ile Pro Val Thr Gln
185             190             195                     200

AAC AGC TCT GGA CAT GAA ACC CCC ATA GGC ACT                         678
Asn Ser Ser Gly His Glu Thr Pro Ile Gly Thr
            205         210             215
```

FIG. 1C

```
GAG ATA GAA GGG AAC ATT TTA GGA TTG GTC CTG TTT GCT CTG GTG                                    726
Glu Ile Glu Gly Asn Ile Leu Gly Leu Val Leu Phe Ala Leu Val
            220             225             230

TTA CGA GTG GCC ATG TTA AAA CTA GAA GGC TCC GAA TTT GAC CTC ATC                                774
Leu Gly Val Ala Met Leu Lys Leu Glu Gly Ser Glu Phe Asp Leu Ile
        235             240             245

CGT TTC AAT TCC CTC AAC TCC AAT TCC GGC ATG ACG GCG GAG ATG GTG CTG TGG                        822
Arg Phe Asn Ser Leu Asn Ser Asn Ser Gly Met Thr Ala Glu Met Val Leu Trp
        250             255             260

ATT ATG TGG TAC GTA CCT GTG GGC ATC ATG TTC CCT GTT ACC AGC AAG                                870
Ile Met Trp Tyr Val Pro Val Gly Ile Met Phe Leu Val Thr Ser Lys
265         270             275             280

ATC GTG GAA ATG AAA AAA GAC ATC GTG CTG GTG CTG AGC CTG GGG                                    918
Ile Val Glu Met Lys Lys Asp Ile Val Leu Val Leu Ser Leu Gly
        285             290             295

TAC ATC TTC GCA TCT ATA TTG GGC CAT CAT ATT ACC AGC GGA GGA GTT                                966
Tyr Ile Phe Ala Ser Ile Leu Gly His His Ile Thr Ser Gly Gly Val
        300             305             310

CTG CCA ATT TAT TTT GTT TTC TTC ACA CGA AAA AAC CCA TTC AGA TTC                                1014
Leu Pro Ile Tyr Phe Val Phe Phe Thr Arg Lys Asn Pro Phe Arg Phe
315             320             325
```

FIG. 1D

| nt pos | Codons and amino acids |
|---|---|
| 1062 | CTC Leu, CTG Leu 330, GGC Gly, CTC Leu, GCC Ala, CCA Pro 335, TTT Phe, GCG Ala, ACA Thr, GCA Ala, TTT Phe 340, GCT Ala, ACC Thr, TGC Cys, TCC Ser |
| 1110 | AGC Ser 345, TCA Ser, GCG Ala, ACC Thr, CTT Leu, CCC Pro 350, TCT Ser, ATG Met, AAG Lys, TGC Cys 355, ATT Ile, GAA Glu, GAG Glu, AAC Asn, AAT Asn 360 |
| 1158 | GGT Gly, GTG Val, GAC Asp, AAG Lys, CTT Leu 365, ATC Ile, AGC Ser, AGG Arg, TTT Phe, ATT Ile 370, AGG Arg, ATG Met, AAG Lys, AAC Asn, AAC Asn |
| 1206 | GTG Val, ATG Met, GAC Asp, GGA Gly, GCA Ala 375, GCC Ala, ATC Ile, CTC Leu, CCC Pro, CTC Leu 380, CAG Gln, TTC Phe, GCC Ala, GGG Gly, ACC Thr |
| 1254 | ATT Ile, CAA Gln, CTC Leu, ACT Thr, GTT Val 385, GAG Glu, ATA Ile, AAC Asn, GCA Ala, GCC Ala 390, GCA Ala, TGT Cys, GTG Val, GTT Val, TTC Phe |
| 1302 | ATT Ile, CTA Leu, ACC Thr, GCG Ala, ACA Thr 395, TCC Ser, AGT Ser, GGA Gly, GCA Ala, CAG Gln 400, CAG Gln, ATT Ile, GGC Gly, GTG Val, CCA Pro |
| 1350 | GCT Ala 405, GGA Gly, GGG Gly, CTC Leu, ATT Ile, ACC Thr 410, CTC Leu, CTG Leu 415, GAG Glu, GCC Ala, ATT Ile, GGG Gly, CTG Leu 420 |

Key positions noted: 330, 335, 340, 345, 350, 355, 360, 365, 370, 375, 380, 385, 390, 395, 400, 405, 410, 415, 420, 425, 430, 435, 440.

FIG. 1E

| | | | | | | | | | | | | | | | | |
|---|---|---|---|---|---|---|---|---|---|---|---|---|---|---|---|---|
| CCT | ACT | CAT | GAC | CTG | CCT | CTG | ATC | GCT | GAC | TGG | ATT | GTG | GAC | | | 1398 |
| Pro | Thr | His | Asp | Leu | Pro | Leu | Ile | Ala | Asp | Trp | Ile | Val | Asp | | | |
| | | | | 445 | | | | 450 | | | | 455 | | | | |
| CGG | ACC | ACG | GTG | CTG | GTG | AAT | CTG | GAG | GGG | GAT | GCC | CTG | GGT | GCA | GGC | 1446 |
| Arg | Thr | Thr | Val | Leu | Val | Asn | Leu | Glu | Gly | Asp | Ala | Leu | Gly | Ala | Gly | |
| | | 460 | | | | | | 465 | | | | | 470 | | | |
| ATT | CTC | CAC | CTG | AAT | CAG | AAG | GCA | ACA | AAG | AAA | GGC | GAG | CAG | GAA | | 1494 |
| Ile | Leu | His | Leu | Asn | Gln | Lys | Ala | Thr | Lys | Lys | Gly | Glu | Gln | Glu | | |
| | | 475 | | | | 480 | | | | | 485 | | | | | |
| CTT | GCT | GAG | GTG | AAA | GAA | GTG | GCC | ATC | CCC | TGC | AAG | TCT | GAG | GAG | | 1542 |
| Leu | Ala | Glu | Val | Lys | Glu | Val | Ala | Ile | Pro | Cys | Lys | Ser | Glu | Glu | | |
| | 490 | | | | 495 | | | | | 500 | | | | | | |
| GAG | ACA | TCG | CCC | CTG | GTG | GTG | ACA | CAC | CAG | AAC | GCT | CCC | GTG | GCC | | 1590 |
| Glu | Thr | Ser | Pro | Leu | Val | Val | Thr | His | Gln | Asn | Ala | Pro | Val | Ala | | |
| 505 | | | | | 510 | | | | | 515 | | | | 520 | | |
| AGT | GCC | CCA | GAA | CTG | AAA | TCC | GAA | AAG | GAG | TCG | GTT | CTG | TGATGGGCT | | | 1636 |
| Ser | Ala | Pro | Glu | Leu | Lys | Ser | Glu | Lys | Glu | Ser | Val | Leu | | | | |
| | | | | 525 | | | | | 530 | | | | | | | |

GGGCTTTGGG CTTGCCTGCC AGCAGTGATG TCCCACCCTG TTCA 1680

FIG. 2A

```
AAAGAAGAGA CCCTCCTAGA AAAGTAAAAT           ATG ACT AAA AGC AAT GGA GAA GAG    54
                                           Met Thr Lys Ser Asn Gly Glu Glu
                                             1                 5

CCC AAG ATG GGG GGC AGG ATG GAG AGA TTC CAG CAG GGA GTC CTG AAA        102
Pro Lys Met Gly Gly Arg Met Glu Arg Phe Gln Gln Gly Val Leu Lys
     10                  15                  20

CGC ACA CTT TTG GCC AGG AAG AAA GTG CAG AAC ATT ACA AAG GAG GTT        150
Arg Thr Leu Leu Ala Arg Lys Lys Val Gln Asn Ile Thr Lys Glu Val
 25                  30                  35                 40

GTT AAA AGT TAC CTG TTT CGG AAT GCT TTT GTG CTG CTC ACA GAG ACC        198
Val Lys Ser Tyr Leu Phe Arg Asn Ala Phe Val Leu Leu Thr Glu Thr
             45                  50                  55

GCT GTC ATT GTG GGT ACA ATC CTT TTC GGA TTT ACC TCC CGA CCA TAC AGA    246
Ala Val Ile Val Gly Thr Ile Leu Phe Gly Phe Thr Ser Arg Pro Tyr Arg
 60                  65                  70

ATG AGC TAC CGG GAA GTC AAG TAC TTC TCC TTT CCT GGG GAA CTT CTG        294
Met Ser Tyr Arg Glu Val Lys Tyr Phe Ser Phe Pro Gly Glu Leu Leu
 75                  80                  85

ATG AGG ATG TTA CAG GTC CTG ATG CCA CTT ATC TCC AGT CTT        342
Met Arg Met Leu Gln Val Leu Met Pro Leu Ile Ser Ser Leu
 90                  95                 100
```

FIG. 2B

```
GTC  ACA  GGA  ATG  GCG  GCG  CTA  GAT  AGT  AAG  GCA  TCA  GGG  AAG  TGG  GAA    390
Val  Thr  Gly  Met  Ala  Ala  Leu  Asp  Ser  Lys  Ala  Ser  Gly  Lys  Trp  Glu
105                           110                 115                      120

TGC  GGA  GCT  GTA  GTC  TAT  TAT  ATG  ACT  ACC  ACC  ATC  ATT  GCT  GTG  GTG    438
Cys  Gly  Ala  Val  Val  Tyr  Tyr  Met  Thr  Thr  Thr  Ile  Ile  Ala  Val  Val
               125                      130                      135

ATT  GGC  ATA  ATC  ATC  GTC  ATT  ATC  ATC  CAT  CCT  GGG  AAG  GCT  ATT  AAG    486
Ile  Gly  Ile  Ile  Ile  Val  Ile  Ile  Ile  His  Pro  Gly  Lys  Ala  Ile  Lys
          140                           145                      150

GAA  AAC  ATG  CAC  AGA  GAA  GGC  GGC  AAA  ATG  TTA  AAT  CGA  GTA  ACA  GCA    534
Glu  Asn  Met  His  Arg  Glu  Gly  Gly  Lys  Met  Leu  Asn  Arg  Val  Thr  Ala
               155                      160                      165

GCC  TTC  CTG  GAC  TTG  ATC  AGG  ATG  AAC  ACC  AAT  CCA  AAG  AGC  CTG  GAA    582
Ala  Phe  Leu  Asp  Leu  Ile  Arg  Met  Asn  Thr  Asn  Pro  Lys  Ser  Leu  Glu
170                      175                      180

TGC  TTT  AAA  GAG  TTT  ATC  AAA  TAT  GAG  TAT  AGA  AGC  TTT  AAA            630
Cys  Phe  Lys  Gln  Phe  Ile  Lys  Tyr  Glu  Tyr  Arg  Ser  Phe  Lys
185                      190                      195                 200

GTG  CCC  ATC  GAG  GCC  AAC  GAA  ACG  CCT  GTG  GGT  GCT  GTG  ATA  AAC  AAT    678
Val  Pro  Ile  Gln  Ala  Asn  Glu  Thr  Leu  Val  Gly  Ala  Val  Ile  Asn  Asn
               205                      210                      215
```

FIG. 2C

| | | | | | | | | | | | | | | | |
|---|---|---|---|---|---|---|---|---|---|---|---|---|---|---|---|
| GTG<br>Val | TCT<br>Ser | GAG<br>Glu | GCC<br>Ala<br>220 | ATG<br>Met | GAG<br>Glu | ACT<br>Thr | CTT<br>Leu | ACC<br>Thr<br>225 | CGA<br>Arg | ATC<br>Ile | ACA<br>Thr | GAG<br>Glu<br>230 | CTG<br>Leu | GTC<br>Val | 726 |
| CCA<br>Pro | GTT<br>Val | CCA<br>Pro<br>235 | GGA<br>Gly | TCT<br>Ser | GTG<br>Val | AAT<br>Asn | GGA<br>Gly<br>240 | GTC<br>Val | AAT<br>Asn | GCC<br>Ala | CTG<br>Leu | GGT<br>Gly<br>245 | CTA<br>Leu | GTT<br>Val | 774 |
| TTC<br>Phe | TCC<br>Ser<br>250 | ATG<br>Met | TGC<br>Cys | TTC<br>Phe | GGT<br>Gly | TTT<br>Phe<br>255 | ATT<br>Ile | GTG<br>Val | GGA<br>Gly | CTG<br>Leu | ATG<br>Met<br>260 | AAC<br>Asn | AAG<br>Lys | CAG<br>Gln | GGG<br>Gly | 822 |
| GAG<br>Gln<br>265 | GCC<br>Ala | CTG<br>Leu | GAG<br>Glu | TTC<br>Phe<br>270 | TTT<br>Phe | GAT<br>Asp | TCT<br>Ser | CTT<br>Leu | AAC<br>Asn<br>275 | GAA<br>Glu | ATG<br>Met | ATC<br>Ile | ATG<br>Met | AGA<br>Arg<br>280 | 870 |
| CTG<br>Leu | GTA<br>Val | GCA<br>Ala | ATA<br>Ile<br>285 | ATG<br>Met | TGG<br>Trp | TAT<br>Tyr | GCC<br>Ala | CCC<br>Pro<br>290 | GTG<br>Val | GGT<br>Gly | GCC<br>Ala | ATT<br>Ile | ATT<br>Ile<br>295 | CTG<br>Leu | 918 |
| ATT<br>Ile | GCT<br>Ala | AAG<br>Lys<br>300 | ATT<br>Ile | ATG<br>Met | GAG<br>Glu | GAA<br>Glu<br>305 | GAC<br>Asp | ATG<br>Met | GGT<br>Gly | GTG<br>Val | ATT<br>Ile<br>310 | CTC<br>Leu | TTC<br>Phe | GGG<br>Gly | GGG<br>Gly | 966 |
| CAG<br>Gln | CTT<br>Leu | GCC<br>Ala<br>315 | ATG<br>Met | TAC<br>Tyr | ACC<br>Thr | GTG<br>Val<br>320 | ACT<br>Thr | GTC<br>Val | GAA<br>Glu<br>305 | GCT<br>Ala | TTA<br>Leu<br>325 | CTC<br>Leu | ATT<br>Ile | CAC<br>His | 1014 |

FIG. 2D

| | | | | | | | | | | | | | | | | |
|---|---|---|---|---|---|---|---|---|---|---|---|---|---|---|---|---|
| GCA<br>Ala | ATC<br>Ile | GTC<br>Val<br>330 | TTG<br>Leu | CCA<br>Pro | CTC<br>Leu<br>335 | CTC<br>Leu | TAC<br>Tyr | TTC<br>Phe | TTG<br>Leu | GTA<br>Val<br>340 | ACA<br>Thr | CGG<br>Arg | AAA<br>Lys | AAC<br>Asn | | 1062 |
| CCT<br>Pro<br>345 | GTT<br>Val | TTT<br>Phe | ATT<br>Ile | GGA<br>Gly<br>350 | TTT<br>Phe | GGG<br>Gly | CTG<br>Leu | CAA<br>Gln | TTG<br>Leu<br>355 | GCA<br>Ala | CTC<br>Leu | ATC<br>Ile | GCT<br>Ala | CTG<br>Leu<br>360 | | 1110 |
| GGG<br>Gly | ACC<br>Thr | TCT<br>Ser | AGT<br>Ser<br>365 | TCA<br>Ser | AGT<br>Ser | CCC<br>Pro | CTA<br>Leu | ACC<br>Thr<br>370 | ATC<br>Ile | CCC<br>Pro | ACC<br>Thr | TTC<br>Phe | AAG<br>Lys | TGC<br>Cys<br>375 | CTG<br>Leu | 1158 |
| GAA<br>Glu | AAT<br>Asn<br>380 | GGC<br>Gly | GTG<br>Val | TCT<br>Ser | GCC<br>Ala | CGC<br>Arg<br>385 | CTA<br>Leu | GTC<br>Val | ACC<br>Thr | ATC<br>Ile | TTC<br>Phe | AAG<br>Lys<br>390 | GTG<br>Val | CTC<br>Leu | CCC<br>Pro | 1206 |
| GTA<br>Val | GCC<br>Ala<br>395 | ATT<br>Ile | AAC<br>Asn | ATG<br>Met | GAT<br>Asp<br>400 | AAG<br>Lys | CGC<br>Arg | GGG<br>Gly | ACT<br>Thr | AGA<br>Arg<br>405 | TAT<br>Tyr | TTC<br>Phe | GAG<br>Glu | TTG<br>Leu | | 1254 |
| GCT<br>Ala | GCC<br>Ala<br>410 | ATT<br>Ile | TTC<br>Phe | CAA<br>Gln<br>415 | AAC<br>Asn | AAC<br>Asn | GAT<br>Asp | TTT<br>Phe | CTC<br>Leu<br>420 | GAA<br>Glu | GCT<br>Ala | GAG<br>Glu | AAC<br>Asn | TTC<br>Phe | GGA<br>Gly | 1302 |
| CAA<br>Gln<br>425 | ATT<br>Ile | ATC<br>Ile | AGC<br>Ser<br>430 | ATC<br>Ile | ACA<br>Thr | ACA<br>Thr | GCT<br>Ala<br>435 | GCC<br>Ala | AGT<br>Ser | ATT<br>Ile | GGG<br>Gly | GCA<br>Ala<br>440 | | | | 1350 |

FIG. 2E

| GCT Ala | ATT Ile | CCT Pro | CAG Gln 445 | GCG Ala | GGC Gly | CTG Leu | GTC Val | ACT Thr 450 | ATG Met | GTC Val | ATT Ile | GTG Val | CTG Leu 455 | ACA Thr | 1398 |
| TCT Ser | GTC Val | GGC Gly | CTG Leu 460 | ACT Thr | GAC Asp | ATC Ile 465 | ACG Thr | CTC Leu | ATC Ile | GCG Ala 470 | GTG Val | GAC Asp | 1446 |
| TGG Trp | TTC Phe | TTG Leu 475 | GAT Asp | CGC Arg | ACC Thr 480 | ACC Thr | ACC Thr | ATC Ile | GGA Gly | GAC Asp | TCC Ser | 1494 |
| CTG Leu | GCT Ala | GGG Gly | ATT Ile | GTG Val | CAC His | TTG Leu | TCA Ser | CGA Arg | CAT His 500 | GAA Glu | CTG Leu | AAG Lys | AAC Asn | 1542 |
| AGA Arg 505 | GAT Asp | GTT Val | ATG Met | GAA Glu | TCA Ser | AAC Asn | GTG Val | GAG Glu 515 | GAA Glu | ATT Ile | GGA Gly | GAA Glu | ATG Met | AAG Lys 520 | 1590 |
| AAA Lys | CCA Pro | TAT Tyr | CAA Gln | CTG Leu 525 | ATT Ile | GCA Ala | CAG Gln | GAC Asp | AAT Asn 530 | GAA Glu | ACT Thr | GAG Glu | AAA Lys | ATC Ile | 1638 |
| GAC Asp | AGT Ser | GAA Glu | ACC Thr 540 | AAG Lys | ATG Met | TAGACTAACA | TAAAGAAACA | CTTT | | | | | | | 1680 |

FIG. 3A

```
                                                                                                      54
GATAGTGCTG AAGAGGAGGG GCGTTCCCAG ACC ATG GCA TCT ACG GAA GGT GCC
                                    Met Ala Ser Thr Glu Gly Ala
                                     1               5

102
AAC AAT ATG CCC AAG CAG GTG GAA GTG CGA ATG CCA GAC AGT CAT CTT
Asn Asn Met Pro Lys Gln Val Glu Val Arg Met Pro Asp Ser His Leu
         10          15                          20

150
GGC TCA GAG GAA AAG CCC CAC CGG AAG CAC CTG CTG CGC CTG GGA TGT
Gly Ser Glu Glu Lys Pro His Arg Lys His Leu Leu Arg Leu Gly Cys
    25              30                      35

198
AAG CTG GGA AAT TGT ATG CTG CTG ACG GTG TTT GGT GTC ATC CCC ATC
Lys Leu Gly Asn Cys Met Leu Leu Thr Val Phe Gly Val Ile Pro Ile
 40                  45              50                          55

246
CCT GAT GTG GTT ATG ATG CCA TTC GCC ATA GGG GAT ATA CTC CCC ATG
Pro Asp Val Val Met Met Pro Phe Ala Ile Gly Asp Ile Leu Pro Met
             60                          65    70

294
ATG AAA ATG CTC ATT CTA GGT CTG AAA GGC CTA TCC AGC ATC ATG AGG
Met Lys Met Leu Ile Leu Gly Leu Lys Gly Leu Ser Ser Ile Met Arg
 75          80                      85

342
                                                    ATC ACA
                                                    Ile Thr
                                                90      95              100
```

FIG. 3B

| | | | | | | | | | | | | | | | |
|---|---|---|---|---|---|---|---|---|---|---|---|---|---|---|---|
| GGG | TTG | TCA | GGC | CTG | GAT | GCT | AAG | GCT | AGT | GGC | CGC | TTG | GGC | ACG | AGA | 390 |
| Gly | Leu | Ser | Gly | Leu | Asp | Ala | Lys | Ala | Ser | Gly | Arg | Leu | Gly | Thr | Arg | |
| | 105 | | | | | 110 | | | | | 115 | | | | | |
| GCC | ATG | GTG | TAT | TAC | ATG | TCC | ACG | ACC | ATC | ATT | CGC | GCA | GTA | CTG | GGG | 438 |
| Ala | Met | Val | Tyr | Tyr | Met | Ser | Thr | Thr | Ile | Ile | Arg | Ala | Val | Leu | Gly | |
| 120 | | | | | 125 | | | | | 130 | | | | | 135 | |
| GTC | ATT | CTG | GTC | TTG | GCT | ATC | CAT | CCA | GCT | GGC | CGC | AAG | CTG | AAG | 486 |
| Val | Ile | Leu | Val | Leu | Ala | Ile | His | Pro | Ala | Gly | Arg | Lys | Leu | Lys | |
| | | | | 140 | | | | | 145 | | | | | 150 | |
| CAG | CTG | GGG | CCT | GGG | AAG | AAT | CCA | GGC | GAA | CCC | AGC | TCC | CTG | GCC | 534 |
| Gln | Leu | Gly | Pro | Gly | Lys | Asn | Pro | Gly | Glu | Pro | Ser | Ser | Leu | Ala | |
| | | | 155 | | | | | 160 | | | | | 165 | | |
| TTC | CTG | GAC | CTT | ATT | CGA | AAT | CTC | TTC | CCT | GTG | AAC | CTT | GTC | GCC | 582 |
| Phe | Leu | Asp | Leu | Ile | Arg | Asn | Leu | Phe | Pro | Val | Asn | Leu | Val | Ala | |
| | | 170 | | | | | 175 | | | | | 180 | | | |
| TGC | TTT | CAA | CAG | CAA | ATT | ACA | GTG | ACG | AAG | ACA | AAA | GTC | GTT | CCA | 630 |
| Cys | Phe | Gln | Gln | Gln | Ile | Thr | Val | Thr | Lys | Thr | Lys | Val | Val | Pro | |
| | 185 | | | | | 190 | | | | | 195 | | | | |
| CCG | GAG | GAC | GAG | AAC | GCA | GCC | ACC · AGC | GCT | GAA | GCA | TCT | CTG | TTG | 678 |
| Pro | Glu | Asp | Glu | Asn | Ala | Ala | Thr Ser | Ala | Glu | Ala | Ser | Leu | Leu | |
| 200 | | | | | 205 | | | 210 | | | | | 215 | |

FIG. 3C

```
AAC GAG ACT GTG ACT GAG CCG GAG ACT AAG ATG GTT ATC AAG              726
Asn Glu Thr Val Thr Glu Pro Glu Thr Lys Met Val Ile Lys
            220         225         230

AAG GGC CTG GAG TTC AAG GAT GGG ATG AAC GTC TTA GGT CTG ATA GGG      774
Lys Gly Leu Glu Phe Lys Asp Gly Met Asn Val Leu Gly Leu Ile Gly
            235         240         245

TTT TTC ATT GCT TTT GGC ATC GCT AAG ATG GGA GAT CAG GCC              822
Phe Phe Ile Ala Phe Gly Ile Ala Lys Met Gly Asp Gln Ala
            250         255         260

AAG CTG ATG GTG GAT TTC AAC AAT ATT TTG GAG ATT GTA ATG AAG          870
Lys Leu Met Val Asp Phe Asn Asn Ile Leu Glu Ile Val Met Lys
            265         270         275

TTA GTG ATC ATG ATC TGG TAC TCT CCC CTG GGT ATC GCC TGC CTG          918
Leu Val Ile Met Ile Trp Tyr Ser Pro Leu Gly Ile Ala Cys Leu
    280         285         290         295

ATC TGT GGA AAG ATT ATC GCA AAG GAC TTA GAA GTG GTT GCT AGG          966
Ile Cys Gly Lys Ile Ile Ala Lys Asp Leu Glu Val Val Ala Arg
            300         305         310

CAA CTG GGG ATG TAC GTA ACA GTG ATA GGC CTC ATC ATC CAC              1014
Gln Leu Gly Met Tyr Val Thr Val Ile Gly Leu Ile Ile His
            315         320         325
```

FIG. 3D

| | | | | | | | | | | | | | | | |
|---|---|---|---|---|---|---|---|---|---|---|---|---|---|---|---|
| GGG | GGC | ATC | TTT | CTC | CCC | TTG | ATT | TAC | TTT | GTA | GTG | ACC | AGG | AAA | AAC | 1062 |
| Gly | Gly | Ile | Phe | Leu | Pro | Leu | Ile | Tyr | Phe | Val | Val | Thr | Arg | Lys | Asn | |
| | | 330 | | | | | 335 | | | | | 340 | | | | |
| CCC | TTC | TCC | CTT | TTT | GCT | GGC | ATT | TTC | CAA | GCT | TGG | ATC | ACT | GCC | CTG | 1110 |
| Pro | Phe | Ser | Leu | Phe | Ala | Gly | Ile | Phe | Gln | Ala | Trp | Ile | Thr | Ala | Leu | |
| | 345 | | | | | 350 | | | | | 355 | | | | | |
| GGC | ACC | GCT | TCC | AGT | GCT | GGA | ACT | TTG | CCT | GTC | ACC | TTT | CGT | TGC | CTG | 1158 |
| Gly | Thr | Ala | Ser | Ser | Ala | Gly | Thr | Leu | Pro | Val | Thr | Phe | Arg | Cys | Leu | |
| 360 | | | | | 365 | | | | | 370 | | | | | 375 | |
| GAA | AAT | CTG | GAT | GGG | ATT | AAG | CGT | GTG | ACT | AGA | TTC | GTC | CTT | CCT | 1206 |
| Glu | Asn | Leu | Asp | Gly | Ile | Lys | Arg | Val | Thr | Arg | Phe | Val | Leu | Pro | |
| | | | | 380 | | | | 385 | | | | | 390 | | | |
| GTT | GGA | GCA | ACC | TTT | GAT | ATG | AAC | ATG | GGT | ACA | CTT | TAT | GAA | GCG | GGA | 1254 |
| Val | Gly | Ala | Thr | Phe | Asp | Met | Asn | Met | Gly | Thr | Leu | Tyr | Glu | Ala | Gly | |
| | | | 395 | | | | | | 400 | | | | 405 | | | |
| GCC | GCC | ATC | TTT | ATA | AGC | CAA | ATG | AAT | GGT | ACC | GTT | CTG | GAT | GGA | 1302 |
| Ala | Ala | Ile | Phe | Ile | Ser | Gln | Met | Asn | Gly | Thr | Val | Leu | Asp | Gly | |
| | 410 | | | | | | 415 | | | | 420 | | | | |
| CAG | ATT | GTG | ACT | GTA | AGC | CTC | ACA | GCC | ACC | CTG | GCA | AGC | GTG | GGA | GCG | 1350 |
| Gln | Ile | Val | Thr | Val | Ser | Leu | Thr | Ala | Thr | Leu | Ala | Ser | Val | Gly | Ala | |
| | 425 | | | | | 430 | | | | | 435 | | | | | |

FIG. 3E

| | | | | | | | | | | | | | | | |
|---|---|---|---|---|---|---|---|---|---|---|---|---|---|---|---|
| GCC<br>Ala<br>440 | AGT<br>Ser | ATC<br>Ile | CCC<br>Pro | AGT<br>Ser | GCC<br>Ala<br>445 | GGG<br>Gly | CTG<br>Leu | GTC<br>Val | ACC<br>Thr | ATG<br>Met<br>450 | CTC<br>Leu | CTC<br>Leu | ATT<br>Ile | CTG<br>Leu | ACA<br>Thr<br>455 | 1398 |
| GCC<br>Ala | GTG<br>Val | GGC<br>Gly | CTG<br>Leu | CCA<br>Pro<br>460 | ACA<br>Thr | GAG<br>Glu | GAC<br>Asp | ATC<br>Ile | AGC<br>Ser<br>465 | TTG<br>Leu | CTG<br>Leu | GTG<br>Val | GCT<br>Ala | GTG<br>Val<br>470 | GAC<br>Asp | 1446 |
| TGG<br>Trp | CTG<br>Leu | GAC<br>Asp<br>475 | AGG<br>Arg | ATG<br>Met | AGA<br>Arg | ACT<br>Thr | TCA<br>Ser<br>480 | GTC<br>Val | AAT<br>Asn | GTT<br>Val | GGT<br>Gly<br>485 | GTG<br>Val | GAC<br>Asp | TCT<br>Ser | | 1494 |
| TTT<br>Phe | GGG<br>Gly | GCT<br>Ala<br>490 | ATA<br>Ile | GTC<br>Val | TAT<br>Tyr | CAC<br>His<br>495 | CTC<br>Leu | TCC<br>Ser | AAG<br>Lys | TCT<br>Ser | GAG<br>Glu<br>500 | CTG<br>Leu | GAT<br>Asp | ACC<br>Thr | | 1542 |
| ATT<br>Ile | GAC<br>Asp<br>505 | TCC<br>Ser | GAG<br>Glu | CAT<br>His | GTG<br>Val<br>510 | CGA<br>Arg | GAA<br>Glu | GAT<br>Asp | ATT<br>Ile | GAA<br>Glu<br>515 | ATG<br>Met | ACC<br>Thr | AAG<br>Lys | ACT<br>Thr | | 1590 |
| CAA<br>Gln<br>520 | TCC<br>Ser | ATT<br>Ile | TAT<br>Tyr | GAT<br>Asp | GAC<br>Asp<br>525 | ATG<br>Met | AAG<br>Lys | AAC<br>Asn | CAC<br>His | AGG<br>Arg<br>530 | GAA<br>Glu | AGC<br>Ser | AAC<br>Asn | ATT<br>Asn<br>535 | | 1638 |
| CAA<br>Gln | TGT<br>Cys | GTC<br>Val | TAT<br>Tyr | GCT<br>Ala<br>540 | GCA<br>Ala | CAC<br>His | AAC<br>Asn | TCT<br>Ser | GTC<br>Val<br>545 | ATA<br>Ile | GTA<br>Val | GAT<br>Asp | GAA<br>Glu | TGC<br>Cys<br>550 | AAG<br>Lys | 1686 |

FIG. 3F

```
GTA ACT CTG GCA GCC AAT GGA AAG TCA GCC GAC TGC AGT GTT GAG GAA      1734
Val Thr Leu Ala Ala Asn Gly Lys Ser Ala Asp Cys Ser Val Glu Glu
        555                 560                 565

GAA CCT TGG AAA CGT GAG AAA TAAGGATATG AGTCTCAGCA AATTCTTGAA         1785
Glu Pro Trp Lys Arg Glu Lys
        570

TAAACTCCCC AGCGT                                                     1800
```

FIG. 4A

```
ATAGCGGGCGA CAGCC ATG AAA GGG CCG GCG AGG AAA GGA TGC CCG AGT TGG           51
                  Met Lys Gly Pro Ala Arg Lys Gly Cys Pro Ser Trp
                   1           5              10

AAG CGC TTC CTG AAG AAT CCG TGG AAC ACC TCC CTG GTG GTG GCC GCG            99
Lys Arg Phe Leu Lys Asn Pro Trp Asn Thr Ser Leu Val Val Ala Ala
        15              20       25

GTG CTA GGC AAT ACA ACC ATT TAC TTC TTT GCT CCT ATT ATA GGA TGC          147
Val Leu Gly Asn Thr Thr Ile Tyr Phe Phe Ala Pro Ile Ile Gly Cys
        30              35      40

CTC ACT CTA GAG AAA CTC TTG ATT ATC GCA TTA GTA TCC GAA ATT CTA          195
Leu Thr Leu Glu Lys Leu Leu Ile Ile Ala Leu Val Ser Glu Ile Leu
 45              50              55              60

ATG GGG ATG CTG AAA GCT TTG CCA AAC GTA TCC GGA AGC ATG ATT GGT          243
Met Gly Met Leu Lys Ala Leu Pro Asn Val Ser Gly Ser Met Ile Gly
                 65              70              75

ATT ACA GGT TCC GAT CTG AAC ACT ATA TCC AAA ATT GCT GTT ATT             291
Ile Thr Gly Val Ser Asp Leu Asn Thr Ile Ser Lys Ile Ala Val Ile
         80              85              90

CTG CGC GCT GTC TAT TTC TGT ACC CTC ATT GCT GTT ATT                      339
Leu Arg Ala Val Tyr Phe Cys Thr Leu Ile Ala Val Ile
         95             100             105
```

FIG. 4B

| | | | | | | | | | | | | | | | |
|---|---|---|---|---|---|---|---|---|---|---|---|---|---|---|---|
| CTA<br>Leu | GGT<br>Gly<br>110 | ATT<br>Ile | GTG<br>Val | CTG<br>Leu | GTG<br>Val | GTG<br>Val<br>115 | AGC<br>Ser | ATC<br>Ile | AAG<br>Lys | CCT<br>Pro | GGT<br>Gly<br>120 | GTC<br>Val | ACC<br>Thr | CAG<br>Gln | AAA<br>Lys | 387 |
| GTG<br>Val<br>125 | GGT<br>Gly | GAA<br>Glu | ATT<br>Ile | GCG<br>Ala | AGG<br>Arg<br>130 | ACA<br>Thr | GGC<br>Gly | AGC<br>Ser | ACC<br>Thr | CCT<br>Pro<br>135 | GAA<br>Glu | GTC<br>Val | AGT<br>Ser | ACG<br>Thr | GTG<br>Val<br>140 | 435 |
| GAT<br>Asp | GCC<br>Ala | ATG<br>Met | GAT<br>Asp<br>145 | CTC<br>Leu | ATC<br>Ile | AGG<br>Arg | AAT<br>Asn | ATG<br>Met<br>150 | TTC<br>Phe | CCT<br>Pro | GAG<br>Glu | GTC<br>Val | AAT<br>Asn | CTT<br>Leu<br>155 | GTC<br>Val | 483 |
| CAG<br>Gln | GCC<br>Ala | TGT<br>Cys | TTT<br>Phe<br>160 | TTA<br>Leu | CAG<br>Gln | TAC<br>Tyr | AAA<br>Lys | ACT<br>Thr<br>165 | AAG<br>Lys | CGT<br>Arg | TTC<br>Phe | GAA<br>Glu | GTG<br>Val<br>170 | AAG<br>Lys | CCT<br>Pro | 531 |
| CCC<br>Pro | AGC<br>Ser | GAT<br>Asp<br>175 | CCA<br>Pro | GCA<br>Ala | ATG<br>Met | AAC<br>Asn | AAG<br>Lys | GAA<br>Glu | ACA<br>Thr | GAG<br>Glu | GAA<br>Glu | GTG<br>Val<br>170 | GAA<br>Glu | AAT<br>Asn | GTC<br>Val | 579 |
| ATG<br>Met | ACA<br>Thr<br>190 | ACT<br>Thr | GCA<br>Ala | ATT<br>Ile | TCC<br>Ser | AAG<br>Lys<br>195 | AAA<br>Lys | ACA<br>Thr | AAG<br>Lys<br>200 | TCC<br>Ser | TTC<br>Phe<br>185 | TAC<br>Tyr | AAA<br>Lys | GCT<br>Ala | GTT<br>Val | 627 |
| GGC<br>Gly<br>205 | ATG<br>Met | TAT<br>Tyr | TCA<br>Ser | GAT<br>Asp | GGC<br>Gly<br>210 | GGC<br>Gly | GTC<br>Val | AAC<br>Asn | CTG<br>Leu | GGC<br>Gly<br>215 | TTG<br>Leu | ATT<br>Ile | ATT<br>Ile | TTT<br>Phe | TGC<br>Cys<br>220 | 675 |
| CTT<br>Leu | GTC<br>Val | TTT<br>Phe | GGA<br>Gly | CTT<br>Leu<br>225 | GTC<br>Val | ATT<br>Ile | GGA<br>Gly | AAA<br>Lys | ATG<br>Met<br>230 | GGA<br>Gly | AAG<br>Lys | GGA<br>Gly | CAA<br>Gln<br>235 | ATT<br>Ile | | 723 |

FIG. 4C

```
CTG GTG GAT TTC TTC AAT GCT TTG AGT GAT GCA ACC ATG AAA ATC GTT    771
Leu Val Asp Phe Phe Asn Ala Leu Ser Asp Ala Thr Met Lys Ile Val
            240                 245                 250

CAG ATC ATC ATG TGT TAT ATG CCA CTA GGT ATT TTG TTC ATT GCT        819
Gln Ile Ile Met Cys Tyr Met Pro Leu Gly Ile Leu Phe Ile Ala
        255                 260                 265

GGG AAG GAA ATA GAC TGG GAA GTT ATA ATC TTC CGC AAG CTG GGC        867
Gly Lys Glu Ile Asp Trp Glu Val Ile Ile Phe Arg Lys Leu Gly
        270                 275                 280

CTT TAC ATG GCC ACA GTC TAT TTC CTG ACT GGG CTT GCA ATC CAC TCC    915
Leu Tyr Met Ala Thr Val Tyr Phe Leu Thr Gly Leu Ala Ile His Ser
            285                 290                 295      300

ATT CTC CCG ATA TTC ATG GCC CAG GCT ATA GTC GTA ATT CCT TTC CGA    963
Ile Leu Pro Ile Phe Met Ala Gln Ala Ile Val Val Ile Pro Phe Arg
        305                 310                 315

TTT GCC ATG GGA CTC CTC GCT ACA CTC GCT ATG CCT ATC TCT           1011
Phe Ala Met Gly Leu Leu Ala Thr Leu Ala Met Pro Ile Ser
            320                 325                 330

TCC AGT TCA GCA ACA CCT GTC GTC TTC CGC TGT GCT GAA AAT           1059
Ser Ser Ser Ala Thr Pro Val Val Phe Arg Cys Ala Glu Asn
    335                 340                 345
```

FIG. 4D

| | | | | | | | | | | | | | | | | | |
|---|---|---|---|---|---|---|---|---|---|---|---|---|---|---|---|---|---|
| AAC<br>Asn | CAG<br>Gln<br>350 | GTG<br>Val | GAC<br>Asp | AAG<br>Lys | AGG<br>Arg | ATC<br>Ile<br>355 | ACT<br>Thr | CGA<br>Arg | TTC<br>Phe | CTG<br>Val | TTA<br>Leu<br>360 | CCC<br>Pro | GTT<br>Val | GGT<br>Gly | GCA<br>Ala | | 1107 |
| ACA<br>Thr<br>365 | ATC<br>Ile | AAC<br>Asn | ATG<br>Met | GAT<br>Asp | GGG<br>Gly<br>370 | ACC<br>Thr | GCG<br>Ala | CTC<br>Leu | TAT<br>Tyr | GAA<br>Glu<br>375 | GCA<br>Ala | CCC<br>Pro | GTG<br>Val | GCG<br>Ala | GTG<br>Val<br>380 | | 1155 |
| TTT<br>Phe | ATT<br>Ile | GCA<br>Ala | CAG<br>Gln | TTG<br>Leu<br>385 | AAT<br>Asn | GAC<br>Asp | CTG<br>Leu | GAC<br>Asp | TTG<br>Leu<br>390 | GGC<br>Gly | ATT<br>Ile | GGG<br>Gly | CAG<br>Gln | GCA<br>Ala | ATC<br>Ile<br>395 | | 1203 |
| ACC<br>Thr | ATC<br>Ile<br>400 | AGT<br>Ser | ATC<br>Ile | GCA<br>Ala | ACA<br>Thr | GCC<br>Ala<br>405 | TCT<br>Ser | AGC<br>Ser | ATC<br>Ile | GGA<br>Gly | GCT<br>Ala<br>410 | CAG<br>Gln | GGG<br>Gly | GTG<br>Val | ATT<br>Ile | | 1251 |
| CTG<br>Leu | GCT<br>Ala<br>415 | GGC<br>Gly | CTG<br>Leu | ACC<br>Thr | ATG<br>Met<br>420 | GTG<br>Val | ATT<br>Ile | GTG<br>Val | GCC<br>Ala | AGT<br>Ser<br>425 | TGG<br>Trp | GGC<br>Gly | CTC<br>Leu | | | | 1299 |
| CCC<br>Pro<br>430 | GCC<br>Ala | GAG<br>Glu | GAT<br>Asp | ACC<br>Thr<br>435 | ATC<br>Ile | CTG<br>Leu | ATT<br>Ile | GTC<br>Val<br>440 | GCT<br>Ala | GAC<br>Asp | TGG<br>Trp | GGC<br>Gly | CTG<br>Leu | | | | 1347 |
| GAC<br>Asp<br>445 | CGG<br>Arg | TTC<br>Phe | AGG<br>Arg | ATG<br>Met<br>450 | GTC<br>Val | AAC<br>Asn | GTC<br>Val | CTT<br>Leu | GGT<br>Gly<br>455 | TTT<br>Phe | GGG<br>Gly | GCT<br>Ala | GAT<br>Asp | ACT<br>Thr<br>460 | | | 1395 |

FIG. 4E

```
GGC ATT GTG GAA AAG CTC TCC AAG GAG CTG GAG ATG GAT GTT        1443
Gly Ile Val Glu Lys Leu Ser Lys Glu Leu Glu Met Asp Val
            460             465             470             475

TCA TCT GAA GTC AAC ATT GTG AAT CCC TTT GCC TTG GAA TCC ACA ATC 1491
Ser Ser Glu Val Asn Ile Val Asn Pro Phe Ala Leu Glu Ser Thr Ile
                480             485             490

CTT GAC AAC GAA GAC TCA GAC ACC AAG AAG TCT TAT GTC AAT GGA GGC 1539
Leu Asp Asn Glu Asp Ser Asp Thr Lys Lys Ser Thr Val Asn Gly Gly
            495             500             505

TTT GCA GTA GAC AAG TCT GAC ATC TCA TTC ACC GAG ACC TCA CAG       1587
Phe Ala Val Asp Lys Ser Asp Ile Ser Phe Thr Glu Thr Ser Gln
    510             515             520

TTC TAGGGCCCCT GGCTGCAGAT GACTGGAAAC AAGGAAGGAC ATTTCGTGAG       1640
Phe
525

AGTCATCTCA AACACGGCTT AAGGAAAAGA GAAA                            1674
```

FIG. 5A

```
ASCT1                                MEKSNETNGLYDSAQAGPAAGPGAPGTAAGRARRCARFLRRQALVLL..TVSGVLAGAGLGAAIR.GL
GLAST1  MTKSNGEEPRMGSRMTRFQQGVRKRTLLAKKKVQNITKEDVKSYLFRNAFVLL..TVSAVIVGTILGFALRPY.
GLT1              MASTEGANNMPKQVEVRMHDSHLSSEEPKHRNLGMRMCDKLGKNLLLSLTVFGVILGAVCGLLRLAA
EAAC1                                                  MGKPARKGCDSKRFLKNNWLLLS.TVVAVLGIVIGVLVREYS

66  SLSRTQVTYLAFPGEMLLRMLRVIILPLVVCSLVSQAASIDASCLQRLGGIRVAYFGL.TTLSASALAVALAFI
 72  KMSYREVKYFSFPGELLMRMLQVLVIPLIISSEVTGMAALDSKASGKMGM.RAVVYYMTTTIAVVIGIIIVI
 69  PIHPDVVMLIAFPGDILMRMLKVLILPLIISSLITGLSGLDAKASGRLGT.RAMVYYMSTTIAAVIGVILLA
 43  NLSTLDKFYFAFPGEILMRMLKLVILPLIVSSMITGVAALDSNVSGKIGL.RAVLYFCTTIIAVILGIVLVVS

130  IKPGSGAQTLQSSDLGLEDSGPPPVPKETVDSFLDLARNLFPSNLVAAFRTYATDYKV........TONSSS
145  IHPGKGT.KENMYREGKIVOVTA.......ADAFLDLIRNMFPPNLVEACFKQFKTSYEKRSFKVPIQANETLLG
142  IHPGNPKLKKQLGPGKKNDEVSS.......LDAFLDLIRNLFPENLVQACFOQIQTVTKKVLVAPPS.EEANTTK
116  IKPGVTQKVDEIDRTGSTPEVST......VDAMLDLIRNMFPENLVQACFQQYKTTREEV..TASDDTGKNGTE

205  GNVTHEKIPIGTEI...........EGMNILGLVLFALVLGVALKKLGSEGEDLIRFFNSLNEATVLNSW
212  AVINVSEAMETLTRIREEMVPVPGSVN.GVNALGLVVFSMCFGFVIGNMKEQGGALREFEDSLNEAIVRLVAV
209  AVISLINETMNEAPEETKIVIKKGLEFKDGMNVLGLIGFFIAEGIAMGKMGVAGGADGGVLOMSERDCHEVSDM
182  ESVTAVMTTAVSENRTKEYRVVGLYS..DGINVLGLIVFCLVFGLVIGKMGEKGGILVDFFNALSDATVKIVQI

265  IMWYVPVGIMFLVGSRIVEMKDIIVLVTSLGKYIFASILGHVITHGGIVLPLIYFVFTRKNPFRFLLGLLAPFAT
285  IMWYAPLGILFLIAGKILEMEDMGVIGGOLAMYTVTIVGLLIHAVILPLIYFLVTRKNPFWVFIGGLLOALIT
283  DHVVFPAGTACLICGKIIAIKDLEVVAROLGMYMITIVVGLIIHGGIFLPLIYEVVTRKNPFSFFAGIFQAWII
254  IMCYMPLGILFLIAGKIIEVEDWEIF.RKLGLYMVTLSGLAIHSIVILPLIYFIVRKNPFRFAMGMTQALLT

339  AFATCSSSATIPSMKCIEENNGVDKRISRFILPIGATVNMDGAAIFQCVAAVFIAGLNNIELNAGOIFGLVT
350  ALGTSSSSATLPITFKCLEENNGVDKRITRFVLPVGATINMDGTALYEALAAIFIAGVNNFDLNFGQIITISIT
357  ALGTASSAGTLPVTFRCLEDNLGIDKRVTRFVLPVGATINMDGTALYEAVAAIFIAGMNGVILDGGQIVTVSLI
327  ALMISSSSATLPVTFRCAEEKNRVDKRITRFVLPVGATINMDGTALYEAVAAVFIAGLNDMDLSIGQIITISVT
```

FIG. 5B

```
     ATASSVGAAGVPAGGVLTIATILEAIGLPTHDLPLILAVDWIVDRTTTVVNVEGDALGAGILHMINQKATKKGE
413  ATAASIGAAGIPQAGLVTMVIVLTSVGLPTDDITLIIAVDWFLDRLRTTNVLGDSLGAGIVEHLSRHELKNRD
433  ATLASIGAASIPSAGLVTMLLILTAVGLPTEDISLLVAVDWLLDRMRTSVNVGDSFGAGIVHLSKSELDTID
431  ATAASIGAAGVPQAGLVTMVIVLSAVGLPAEDVTLLIAVDWLLDRFRTVVNVLGDAFGTGIVEKLSKKELEQMD
401

487  QELAEVKVEAIPNCKSEETSPLVTHQNPAGPVASAPELESKESVL       532
507  VEMGNSVIEENEMKKPYQLIAQDNEPEKPVADSETKM        543
505  SQHRMHEDIEMTKTQSVYDDTKNHRESNSNQCVYAAHNSVVIDECKVTLAANGKSADCSVEEEPWKREK      573
475  VSSEVNIVNPFALESATLDNEDSDTKKSYINGGFAVDKSDTISFTQTSQF     524
```

FIG. 11

```
EAAT1    MTKSNGEEPKMGGRMERFQQGVRKRTLLAKKKV N TKKQVKSYLFGNPFVLL..TVTAVIVGI.LGFIRPY.
EAAT2            MASTEGANNMPKQVEVRMPDSHLGSEEPKHRMLGLRLCDKLGKNLLLTLTVFGVILGAVCGGLLRLAS
EAAT3                                      MGKPARKGCPSWKRFLKNNWVLLS.TVAAVLIGITTGVLVREHS
                                                                        ───1───

RMSYREVKYFSFPGELIMRMLQMLVLPLIISSLVTGMAALDSKASGKMGMRAVVYYMTTTIAVIGIIVIII
  72     PIMPDVVMLIAFPGDIIMRMLKMLILPLIISSLITGLSGIDAKASGRLGTRAMVYYMSTTIAAVLGVLVLAI
  69      N LSTLEKFYFAFPGEILMRMLKLILLIPLIISSMITGVAALDS N VSGKIGLRAVVYYFGTTLIAVILGIVLVSI
  44                                             ───2───                       ───3───

HPGKGT KENMHREGKIVRVTAADAFLDLIRNMFPPNLVEACFKQFKTGYEKRSFKVPIQA N  B TLVGAVIN NY S
 146     HPGNPKLKKQLGPGKKNDEVSSLDAFLDLIRNLFPENLVQACFQQIQTVTKKVLVAPPPDEE  A N  TSAEVSLL N
 143     KPGVTQKVGEIARTGSTPEVSTVDAMIDLIRNMFPENLVQACFQQVKTKRFEV..KPPSDPF  N M  TEESFTAVM
 118                                                                       ───5───

EAMETLTRITEELVPVPGSVN.GVNALGLVVFSMCFGFVIGNMKEQGQALREFFDSLNEAIMRLVAVIM M TAPE
 219     ETVTEVPEETKMVIKKGLEFKDGMNVLGLIGEFIAFGIAMGRMGDQAKLMVDEFNILNEIVMKIVIMIM M YSPI
 217     TTAIS N KTKFYKIVGMYS..DGINVLGLIVFCLVFGLVIGKMGEKGQILVDFFNALSDATMKIVQIIMCVMPL
 190                                                                ───6───

GILFLIAGKIVEMEDMGVIGGQLAMYTVTVIGLLHAVIVIPLLYELVTRKNPWVFIGGLIQALTTALGTSSS
 292     GIACLICGKITAIKDLEVVARQLGMYMYTVIIGLIIHGGIIFSLFAGIFQAWITALGTASS
 291     GILFLIAGKTIEVEDWFIF.RKLGLYMATVLTGLAIHSIVILPLIYFIVRKNPFFAMGMAQALTALMISSS
 261                                                ───7───
                                                                  ───8───

SATLPITEKCLEENNGVDKRVTRFVLPVGATINMDGTALYEALAATFIAQVNNFELNFGQIITSITATAASIG
 366     AGTLPITFKCLEENLGIDKRVTRFVLPVGATINMDGTALYEAVAAIFIAQMNGVVIDGGQIVTVSLTATLASVG
 385     SATLPITFKCAEENNQVDKRITRFVLPVGATINMDGTALYEAVAAVFIAQLNDLDLGIGQIITSITATSASIG
 334
```

FIG. 11A

```
440  AAGIPQAGLVTMVTVLTSVGLPTDDITLLIIAVDWFLDRLRTTTNVLGDSLGAGTVEHLSRHEEKNRDVEMGNSV
439  AASIPSAGLVTMLLITTAVGLPTEDISLLVAVDWLLDRMRTSVNVVGDSFGAGIVYHLSKSEIDTIDSQMRVHE
408  AAGVPQAGLVEMVTVLSAVGLPAEDVTLIIAVDWLLIDRFRTMVNVLGDAFGTGIVEKLSKKELEQMDVSSEVNI

514  IEENEMKKPYQLIAQDNLTEKPIDSETKM  542
513  DIEMTKTQSIYDDMKNHRESNSNQCVYAAHNSVIVDECKVTLAANGKSADCSVEEPWKREK  574
482  VNPFALESTILDNEDSDTKKSYVNGGFAVDKSDTISFTQTSQF  525
```

AMINO ACID TRANSPORTERS AND USES

This application is a divisional of U.S. Ser. No. 08/546,666, filed Oct. 23, 1995, now U.S. Pat. No. 5,776,774, which is a divisional of U.S. Ser. No. 08/140,729, filed Oct. 20, 1993, now U.S. Pat. No. 5,658,782, issued Aug. 19, 1997. The disclosures of each of these prior applications are considered as being part of the disclosure of the application and are explicitly incorporated by reference herein.

This invention was made with government support under National Institute of Health grants DA07595 and DA03160. The government has certain rights to this invention.

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding each of four novel human amino acid transporter genes. The invention also relates to the construction of recombinant expression constructs comprising such cDNAs from each of the four novel himan amino acid transporter genes of the invention, said recombinant expression constructs being capable of expressing amino acid transporter proteins in cultures of transformed prokaryotic and eukaryotic cells. Production of the transporter proteins in such cultures is also provided. The invention relates to the use of such cultures of such transformed cells to produce homogeneous compositions of each transporter protein. The invention also provides cultures of such cells producing transporter proteins for the characterization of novel and useful drugs. Antibodies against and epitopes of these transporter proteins are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain (see Nicholls & Attwell, 1990, TiPS 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, Nature 360: 464–467).

Glutamate is one example of such an amino acid. Glutamate is an excitatory neurotransmitter (i.e., excitatory neurons use glutamate as a neurotransmitter). When present in excess (>about 300 μM; Bouvier et al., 1992, Nature 360: 471–474; Nicholls & Attwell, ibid.; >5 μM for 5 min.; Choi et al., 1987, J. Neurosci. 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke, anoxia and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptimal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, J. Biol. Chem. 242: 5237–5246 report the discovery of a neutral amino acid transporter (termed the ACS transporter) in Erlich ascites tumor cells.

Makowske & Christensen, 1982, J. Biol. Chem. 257: 14635–14638 provide a biochemical characterization of hepatic amino acid transport.

Kanner & Schuldiner, 1987, CRC Crit. Rev. Biochem. 22: 1–38 provide a review of the biochemistry of neurotransmitters.

Olney et al., 1990, Science 248: 596–599 disclose that the amino acid cysteine is a neurotoxin when present in excess extracellularly.

Wallace et al., 1990, J. Bacteriol. 172: 3214–3220 report the cloning and sequencing of a glutamate/aspartate transporter gene termed gltP from *Escherichia coli* strain K12.

Kim et al., 1991, Nature 352: 725–728 report the discovery that a cationic amino acid transporter is the cell surface target for infection by ecotropic retroviruses in mice.

Wang et al., 1991, Nature 352: 729–731 report the discovery that a cationic amino acid transporter is the cell surface target for infection by ecotropic retroviruses in mice.

Maenz et al., 1992, J. Biol. Chem. 267: 1510–1516 provide a biochemical characterization of amino acid transport in rabbit jejunal brush border membranes.

Bussolati et al., 1992, J. Biol. Chem. 267: 8330–8335 report that the ASC transporter acts in an electrochemically neutral manner so that sodium ion co-transport occurs without disrupting the normal membrane potential of the cells expressing the transporter.

Engelke et al., 1992, J. Bacteriol. 171: 5551–5560 report the cloning of a dicarboxylate carrier from *Rhizobium meliloti*.

Guastella et al., 1992, Proc. Natl. Acad. Sci. USA 89: 7189–7193 disclose the cloning of a sodium ion and chloride ion-dependent glycine transporter from a glioma cell line that is expressed in the rat forebrain and cerebellum.

Kavanaugh et al., 1992, J. Biol. Chem. 267:22007–22009 report that biochemical characterization of a rat brain GABA transporter expressed in vitro in *Xenopus laevis* oocytes.

Storck et al., 1992, Proc. Natl. Acad. Sci. USA 89: 10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, Nature 360: 467–471 disclose the cloning and sequencing of a sodium ion-dependent, high affinity glutamate transporter from rabbit small intestine termed EAAC1.

Kong et al., 1993, J. Biol. Chem. 268: 1509–1512 report the cloning and sequencing of a sodium-ion dependent neutral amino acid transporter of the A type that is homologous to a sodium-ion dependent glucose transporter.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids, each nucleic acid having a nucleotide sequence of a novel amino acid transporter gene. The nucleic acids provided by the invention each comprise a complementary DNA (cDNA) copy of the corresponding mRNA transcribed in vivo from each of the amino acid transporter genes of the invention. Also provided are the deduced amino acid sequences of each the cognate proteins of the cDNAs provided by the invention.

This invention provides nucleic acids, nucleic acid hybridization probes, recombinant eukaryotic expression constructs capable of expressing the amino acid transporters of the invention in cultures of transformed cells, such cultures of transformed eukaryotic cells that synthesize the amino acid transporters of the invention, homogeneous compositions of each of the amino acid transporter proteins, and antibodies against and epitopes of each of the amino acid transporter proteins of the invention. Methods for characterizing these transporter proteins and methods for using these proteins in the development of agents having pharmacological uses related to these transporter proteins are also provided by the invention.

In a first aspect, the invention provides a nucleic acid having a nucleotide sequence encoding a human neutral amino acid transporter that is the ASCT1 transporter (SEQ ID No:2). In this embodiment of the invention, the nucleotide sequence includes 1680 nucleotides of the human ASCT1 cDNA comprising 1596 nucleotides of coding sequence, 30 nucleotides of 5' untranslated sequence and 54 nucleotides of 3' untranslated sequence. In this embodiment of the invention, the nucleotide sequence of the ASCT1 transporter consists essentially of the nucleotide sequence depicted in FIG. 1 (SEQ ID No:2). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding ASCT1 disclosed herein.

The corresponding ASCT1 protein molecule, having the deduced amino acid sequence consisting essentially of the sequence shown in FIG. 1 (SEQ ID No.:3), is also claimed as an aspect of the invention. The use of the term "consisting essentially of" herein is as described above. Similarly, the corresponding ASCT1 protein molecule, having the deduced amino acid sequence consisting essentially of the sequence shown in FIG. 1 (SEQ ID No.:3), is also claimed as an aspect of the invention. ASCT1 protein molecules provided by the invention are understood to have substantially the same biological properties as the ASCT1 protein molecule encoded by the nucleotide sequence described herein.

In another aspect, the invention comprises a homogeneous composition of the 55.9 kD mammalian ASCT1 transporter or derivative thereof, said size being understood to be the size of the protein before any post-translational modifications thereof. The amino acid sequence of the ASCT1 transporter or derivative thereof preferably consists essentially of the amino acid sequence of the human ASCT1 transporter protein shown in FIG. 1 (SEQ ID No:3).

In a second aspect, the invention provides a nucleic acid having a nucleotide sequence encoding a human excitatory amino acid transporter that is the EAAT1 transporter (SEQ ID No:4). In this embodiment of the invention, the nucleotide sequence includes 1680 nucleotides of the human EAAT1 cDNA comprising 1626 nucleotides of coding sequence, 30 nucleotides of 5' untranslated sequence and 24 nucleotides of 3' untranslated sequence. In this embodiment of the invention, the nucleotide sequence of the EAAT1 transporter consists essentially of the nucleotide sequence depicted in FIG. 2 (SEQ ID No:4). The use of the term "consisting essentially of" herein is as described above.

In another aspect, the invention comprises a homogeneous composition of the 59.5 kilodalton (kD) mammalian EAAT1 transporter or derivative thereof, said size being understood to be the size of the protein before any post-translational modifications thereof. The amino acid sequence of the EAAT1 transporter or derivative thereof preferably consists essentially of the amino acid sequence of the human EAAT1 transporter protein shown in FIG. 2 (SEQ ID No:5). EAAT1 protein molecules provided by the invention are understood to have substantially the same biological properties as the EAAT1 protein molecule encoded by the nucleotide sequence described herein.

In a third aspect, the invention provides a nucleic acid having a nucleotide sequence encoding a human excitatory amino acid transporter that is the EAAT2 transporter (SEQ ID No:6). In this embodiment of the invention, the nucleotide sequence includes 1800 nucleotides of the human EAAT2 cDNA comprising 1722 nucleotides of coding sequence, 33 nucleotides of 5' untranslated sequence and 45 nucleotides of 3' untranslated sequence. In this embodiment of the invention, the nucleotide sequence of the EAAT2 transporter consists essentially of the nucleotide sequence depicted in FIG. 3 (SEQ ID No:6). The use of the term "consisting essentially of" herein is as described above.

The corresponding EAAT2 protein molecule, having the deduced amino acid sequence consisting essentially of the sequence shown in FIG. 3 (SEQ ID No.:7), is also claimed as an aspect of the invention. EAAT2 protein molecules provided by the invention are understood to have substantially the same biological properties as the EAAT2 protein molecule encoded by the nucleotide sequence described herein.

In another aspect, the invention comprises a homogeneous composition of the 62.1 kD mammalian EAAT2 transporter or derivative thereof, said size being understood to be the size of the protein before any post-translational modifications thereof. The amino acid sequence of the EAAT2 transporter or derivative thereof preferably consists essentially of the amino acid sequence of the human EAAT2 transporter protein shown in FIG. 3 (SEQ ID No:7).

In yet another aspect, the invention provides a nucleic acid having a nucleotide sequence encoding a human excitatory amino acid transporter that is the EAAT3 transporter (SEQ ID No:8). In this embodiment of the invention, the nucleotide sequence includes 1674 nucleotides of the human EAAT3 cDNA comprising 1575 nucleotides of coding sequence, 15 nucleotides of 5' untranslated sequence and 84 nucleotides of 3' untranslated sequence. In this embodiment of the invention, the nucleotide sequence of the EAAT3 transporter consists essentially of the nucleotide sequence depicted in FIG. 4 (SEQ ID No:8). The use of the term "consisting essentially of" herein is as described above.

The corresponding EAAT3 protein molecule, having the deduced amino acid sequence consisting essentially of the sequence shown in FIG. 4 (SEQ ID No.:9), is also claimed as an aspect of the invention. EAAT3 protein molecules provided by the invention are understood to have substantially the same biological properties as the EAAT3 protein molecule encoded by the nucleotide sequence described herein.

In another aspect, the invention comprises a homogeneous composition of the 57.2 kD mammalian EAAT3 transporter or derivative thereof, said size being understood to be the size of the protein before any post-translational modifications thereof. The amino acid sequence of the EAAT3 transporter or derivative thereof preferably consists essentially of the amino acid sequence of the human EAAT3 transporter protein shown in FIG. 4 (SEQ ID No:9).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of these transporter genes in various tissues of mammals, including humans. It is also an object of the present invention to provide nucleic acid hybridization probes derived from the sequences of the amino acid transporter genes of the invention to be used for the detection and diagnosis of genetic diseases. It is an object of this invention to provide nucleic acid hybridization probes derived from the DNA sequences of the amino acid transporter genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporters of the invention. It is a particular object to provide monoclonal antibodies against these amino acid transporters, must preferably the human excitatory and neutral amino acid transporters as herein disclosed. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of an amino acid transporter of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the amino acid transporters of the invention. Chimeric antibodies immunologically reactive against the amino acid transporter proteins of the invention are also within the scope of this invention.

The present invention provides recombinant expression constructs comprising a nucleic acid encoding an amino acid transporter of the invention wherein the construct is capable of expressing the encoded amino acid transporter in cultures of cells transformed with the construct. Preferred embodiments of such constructs comprise the human EAAT1 cDNA (SEQ ID No.:4), the human EAAT2 cDNA (SEQ ID No.:6), the human EAAT3 cDNA (SEQ ID No.:8), and human ASCT1 cDNA (SEQ ID No.:2), each construct being capable of expressing the amino acid transporter encoded therein in cells transformed with the construct.

The invention also provides cultures cells transformed with the recombinant expression constructs of the invention, each such cultures being capable of and in fact expressing the amino acid transporter encoded in the transforming construct.

The present invention also includes within its scope protein preparations of prokaryotic and eukaryotic cell membranes containing at least one of the amino acid transporter proteins of the invention, derived from cultures of prokaryotic or eukaryotic cells, respectively, transformed with the recombinant expression constructs of the invention. In a preferred embodiment, each preparation of such cell membranes comprises one species of the amino acid transporter proteins of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells transformed with a recombinant expression construct of the invention are contacted with such a compound, and the effect of the compound on the transport of the appropriate amino acid is assayed. Additional preferred embodiments comprise quantitative analyses of such effects.

The present invention is also useful for the detection of analogues, agonists or antagonists, known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A through 1E illustrate the nucleotide (SEQ ID No.:2) and amino acid (SEQ ID No.:3) sequences of the human ASCT1 neutral amino acid transporter.

FIGS. 2A through 2E illustrate the nucleotide (SEQ ID No.:4) and amino acid (SEQ ID No.:5) sequences of the human EAAT1 excitatory amino acid transporter.

FIGS. 3A through 3F illustrate the nucleotide (SEQ ID No.:6) and amino acid (SEQ ID No.:7) sequences of the human EAAT2 excitatory amino acid transporter.

FIGS. 4A through 4E illustrate the nucleotide (SEQ ID No.:8) and amino acid (SEQ ID No.:9) sequences of the human EAAT3 excitatory amino acid transporter.

FIGS. 5A and 5B present an amino acid sequence comparison between human ASCT1, GLAST1, GLT1 and EAAC1.

FIGS. 11 and 11A illustrate the degree of predicted amino acid sequence homology between the novel human glutamate transporters EAAT1, EAAT2 and EAAT3; overbars indicate nine regions of hydrophobicity determined using the algorithm of Eisenberg et al., and potential sites of N-linked glycosylation are shown by the circled asparagine (N) residues.

DETAILED DESCRIPTION OF THE PREFERRED EMBODIMENTS

Figure 6A:
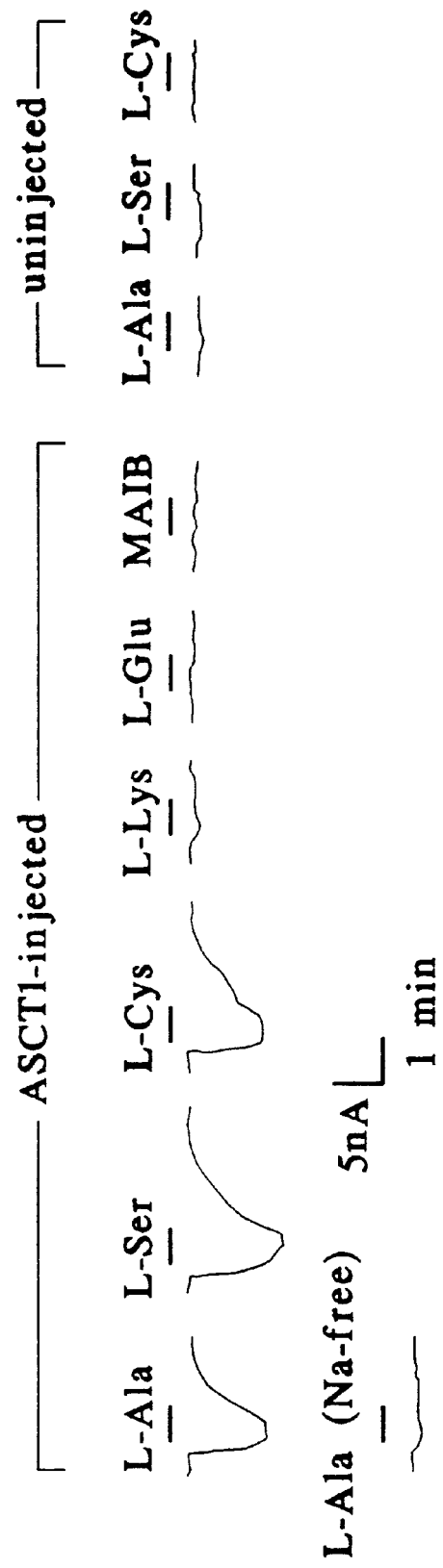
FIGS. 6A through 6C illustrate transmembrane electrochemical currents in *Xenopus laevis* oocytes microinjected with RNA encoding ASCT1 and contacted with the indicated amino acids (FIG. 6A); the amino acid concentration dependence of such electrochemical currents (FIG. 6B); and a plot of normalized current vs. amino acid concentration illustrating the kinetic parameters of amino acid transport (FIG. 6C).

The term "human amino acid transporter EAAT1" as used herein refers to proteins consisting essentially of, and having substantially the same biological activity as, the protein encoded by the nucleic acid depicted in FIGS. 2A through 2E (SEQ ID No.:4). This definition is intended to encompass natural allelic variations in the EAAT1 sequence. Cloned nucleic acid provided by the present invention may encode EAAT1 protein of any species of origin, including, for example, mouse, rat, rabbit, cat, and human, but preferably the nucleic acid provided by the invention encodes EAAT1 receptors of mammalian, most preferably human, origin.

The term "human amino acid transporter EAAT2" as used herein refers to proteins consisting essentially of, and having substantially the same biological activity as, the protein encoded by the nucleic acid depicted in FIGS. 3A through 3F (SEQ ID No.:6). This definition is intended to encompass natural allelic variations in the EAAT2 sequence. Cloned nucleic acid provided by the present invention may encode EAAT2 protein of any species of origin, including, for example, mouse, rat, rabbit, cat, and human, but preferably the nucleic acid provided by the invention encodes EAAT2 receptors of mammalian, most preferably human, origin.

The term "human amino acid transporter EAAT3" as used herein refers to proteins consisting essentially of, and having substantially the same biological activity as, the protein encoded by the nucleic acid depicted in FIGS. 4A through 4E (SEQ ID No.:8). This definition is intended to encompass natural allelic variations in the EAAT3 sequence. Cloned nucleic acid provided by the present invention may encode EAAT3 protein of any species of origin, including, for example, mouse, rat, rabbit, cat, and human, but preferably the nucleic acid provided by the invention encodes EAAT3 receptors of mammalian, most preferably human, origin.

The term "human amino acid transporter ASCT1" as used herein refers to proteins consisting essentially of, and having substantially the same biological activity as, the protein encoded by the nucleic acid depicted in FIGS. 1A through 1E (SEQ ID No.:2). This definition is intended to encompass natural allelic variations in the ASCT1 sequence. Cloned nucleic acid provided by the present invention may encode ASCT1 protein of any species of origin, including, for example, mouse, rat, rabbit, cat, and human, but preferably the nucleic acid provided by the invention encodes ASCT1 receptors of mammalian, most preferably human, origin.

Each of the nucleic acid hybridization probes provided by the invention comprise DNA or RNA consisting essentially of the nucleotide sequence of one of the amino acid transporters, depicted in FIGS. 1A through 1E, FIGS. 2A through 2E, FIGS. 3A through 3F and FIGS. 4A through 4E (SEQ ID Nos.:2,4,6,8), or any portion thereof effective in nucleic acid hybridization. Mixtures of such nucleic acid hybridization probes are also within the scope of this embodiment of the invention. Nucleic acid probes as provided herein are useful for detecting amino acid transporter gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and U.S. Pat. No. 4,683,202 to Mullis.

Each of the amino acid transporter proteins may be synthesized in host cells transformed with a recombinant expression construct comprising a nucleic acid encoding the particular amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, J. Biol. Chem. 264: 8222–8229). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182). Transformed host cells may express the amino acid transporter protein, but host cells transformed for purposes of cloning or amplifying nucleic acid hybridization probe DNA need not express the transporter. When expressed, each of the amino acid transporters of the invention will typically be located in the host cell membrane. See, Sambrook et al., ibid.

Cultures of cells derived from multicellular organisms are a desirable host for recombinant amino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. COS-7 cells are preferred.

The invention provides homogeneous compositions of each of the human EAAT1, EAAT2, EAAT3 and ASCT1 amino acid transporter proteins produced by transformed eukaryotic cells as provided herein. Each such homogeneous composition is intended to be comprised of the corresponding amino acid transporter protein that comprises at least 90% of the protein in such a homogenous composition. The invention also provides membrane preparation from cells expressing each of the amino acid transporter proteins as the result of transformation with a recombinant expression construct, as described herein.

Amino acid transporter proteins made from cloned genes in accordance with the present invention may be used for screening amino acid analogues, or agonist or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a particular amino acid transporter, pure preparations of membranes containing the transporter can be obtained.

The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter proteins or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter proteins of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses one of the amino acid transporters provided by the invention, or any cell or cell line that expresses one of the amino acid transporters of the invention, or any epitope thereof, as a result of molecular or genetic engineering, or that has been treated to increase the expression of an endogenous or heterologous amino acid transporter protein by physical, biochemical or genetic means. Preferred cells are E. coli and insect SF9 cells, most preferably E. coli cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably E. coli cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Human Neutral Amino Acid Transporter cDNA

In order to clone a novel human neutral amino acid transporter, a cDNA library was prepared from human motor cortex mRNA using standard techniques [see Sambrook et al., 1990, *Molecular Cloning: A Laboratory Manual* (Cold Spring Harbor Press: New York)]. Briefly, total RNA was isolated using the method of Chomczynski & Sacchi (1987, Anal. Biochem. 162: 156–159), wherein the tissue is disrupted and solubilized in a solution containing guanidinium isothiocyanate and the RNA purified by phenol/chloroform extractions. Total cellular RNA thus isolated was then enriched for poly (A$^+$) mRNA by oligo (dT) chromatography. A mixture of oligo (dT)-primed and random-primed mRNA was converted to cDNA using the Superscript Choice System (Bethesda Research Labs, Gaithersburg, Md.). cDNA was ligated into the cloning vector λZAPII (Strategene, La Jolla, Calif.), packaged into phage heads using commercially-available packaging extracts (Strategene) and used to infect E. coli. Lawns of infected bacterial cells were used to make plaque lifts for hybridization using standard conditions (see Sambrook, et al., ibid.).

This cDNA library was hybridized with a $^{32}$P-labeled oligonucleotide having the following sequence:

```
5'-CTG(A/G)GC(A/G)ATGAA(A/G)ATGGCAGCCAGGGC(C/T)TCATACAGGGCTGTGCC-    (SEQ ID NO:1)
(A/G)TCCATGTT(A/G)ATGGT(A/G)GC-3'.
```

(This oligonucleotide was obtained commercially from Oligos, Etc., Wilsonville, Oreg.). This oligonucleotide was chosen on the basis of shared homology between a cloned rat glutamate transporter gene (GLAST1) and the bacterial glutamate transporter gene gltP (see Storck et al, ibid. and Wallace et al., ibid.), which suggested an important and conserved structural motif. Hybridization was performed at 50° C. in a solution containing 0.5M Na$_2$HPO$_4$ (pH 7.15)/ 7% sodium dodecyl sulfate (SDS) and the filters were washed at 60° C. in 2×SSPE [0.36M NaCl/20 mM sodium phosphate (pH 7.7)/2 mM ethylenediamine tetraacetic acid (EDTA)] and 1% SDS. Hybridizing clones were identified by autoradiography at −70° C. using tungsten-containing intensifying screens (DuPont-NEN, Wilmington, Del.).

More than 20 positively-hybridizing clones were detected in screening experiments using the above-described primer. One of these clones was excised from the cloning vector in vivo by superinfection with a defective filamentous phage that recognizes and excises cloned insert sequences along with adjacent modified phage replication-form sequences (termed pBluescript SK and available from Strategene). This clone contained a 2.7 kilobase (kb) insert, which was sequenced using the dideoxy-chain termination method of Sanger et al. (1977, Proc. Natl. Acad. Sci. USA 74: 5463), using Sequenase 2.0, a modified form of bacteriophage T7 DNA polymerase (U.S. Biochemical Corp., Cleveland, Ohio). The nucleotide sequence of the portion of this clone containing an open reading frame (encoding the ASCT1 gene) is shown in FIGS. 1A through 1E.

This ASCT1 clone (SEQ ID No.:2) was found to be comprised of about 180 bp of 5' untranslated region, about 900 bp of 3' untranslated region and an open reading frame of 1596 bp encoding the ASCT1 transporter protein (comprising 532 amino acids). The initiator methionine codon was found to be the first methionine codon 3' to an in-frame stop codon and embedded within the consensus sequence for eukaryotic translation initiation (see Kozak, 1987, Nucleic Acids Res 15: 8125–8132). The ASCT1 amino acid sequence (SEQ ID No.:3; also shown in FIGS. 1A through 1E) was found to exhibit similarity to other known glutamate transporter subtypes (an amino acid sequence comparison is shown in FIGS. 5A and 5B). An amino acid comparison between glutamate transporters from rat (GLAST1 and GLT-1) and rabbit (EAAC1) showed 39%, 34% and 39% sequence identity (respectively) between these amino acid transporter proteins (shown in FIGS. 5A and 5B by shaded boxes). This degree of sequence identity is comparable to the sequence identity between these glutamate subtypes themselves. Both the amino and carboxyl termini were found to be divergent between these transporter proteins, and diversity was also found in the extracellular domains of these putative protein sequences, which contain conserved potential N-glycosylation sites (shown in FIGS. 5A and 5B by open boxes). It was noted that a highly conserved sequence (comprising the amino acids -LYEA-) in the glutamate transporters was replaced by the unrelated amino acid sequence -IFQC- in the ASCT1 sequence (at positions 385–387 of the ASCT1 amino acid sequence shown in FIGS. 5A and 5B). 6–10 putative transmembrane domains were found using the algorithm of Eisenberg et al. (1984, J. Molec. Biol. 179: 125–142). On the basis of these data ASCT1 was determined to encode a related but distinct and novel member of the amino acid transporter family.

EXAMPLE 2

Isolation of Human Excitatory Amino Acid Transporter cDNA

The remaining (>20) positively-hybridizing clones from the human motor cortex cDNA library detected by hybridization with the primer described in Example 1 (SEQ ID No.:1) were isolated and the corresponding plasmids obtained by in vivo excision after superinfection with defective phage as described in Example 1 above. These resulting plasmids were isolated and purified using conventional techniques (see Sambrook et al., ibid.). Four classes of clones were distinguished based on differential hybridization experiments using each clone as a hybridization probe against a panel of the remaining clones one after another, where conditions of hybridization stringency were varied to distinguish between each of the classes.

Representative clones from each class were sequenced as described in Example 1. One class of clones represented the ASCT1 cDNA sequences described in Example 1. The other three classes were found to encode novel proteins having amino acid sequences homologous to but distinct from the human ASCT1 sequence. Clone GT5 was determined to contain a 4.0 kb insert encoding a protein having a predicted amino acid sequence (termed EAAT1; SEQ ID No.:4) homologous to but distinct from the rat GLAST1 cDNA clone of Storck et al. (ibid.). Clone GT13 was determined to contain a 2.5 kb insert comprising an open reading frame corresponding to a full-length coding sequence for a novel human transporter gene termed EAAT2 (SEQ ID No.:6). Clone GT11 was found to contain a partial sequence of another novel human transporter termed EAAT3. The EAAT3 clone was used to re-screen the cDNA library described in Example 1. The result of these re-screening experiments was the isolation of Clone GT11B containingza full-length open reading frame encoding EAAT3 (SEQ ID No.:8).

FIGS. 11 and 11A show the results of alignment of the predicted amino acid sequences of the three novel glutamate transporters of the invention. Nine regions of Eisenberg algorithm predicted hydrophobicity are denoted by overlining, and potential sites of N-linked glycosylation (consensus sequence N-X-S/T, where X is any amino acid) are indicated by the circles asparagine (N) residues. EAAT1 shares 47% (253/542) amino acid sequence identity with EAAT2 and 46% (262/574) sequence identity with EAAT3, whereas the EAAT2 sequence is 45% (259/574) identical to the predicted EAAT3 sequence. Cross-species comparisons of the predicted amino acid sequences of these novel human glutamate transporters revealed the following relationships: EAAT1 was found to be 96% homologous with the rat GLAST1 sequence (Storck et al., ibid.); EAAT2 was found to be 90% homologous with the rat GLT1 sequence (Pines et al., 1992, ibid.); and EAAT3 was found to be 93% homologous with the rabbit EAAC1 sequence (Kanai & Hediger, 1992, ibid.). These results indicate that EAAT1, EAAT2 and EAAT3 are related but distinct members of the glutamate transporter family of amino acid transporters.

EXAMPLE 3

Functional Expression of the ASCT1 Amino Acid Transporter Gene in Xenopus Oocytes The sequence similarity between ASCT1 and the glutamate transporters GLAST1, EAAC1 and GLT-1 suggested that the protein encoded by ASCT1 was an amino acid transporter. The ability of the ASCT1 gene product to transport amino acids, and the identity of which amino acids might be transported by this gene product, was assayed in *Xenopus laevis* oocytes following microinjection of in vitro synthesized ASCT1 RNA.

Briefly, the coding sequence of the ASCT1 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For ASCT1, the sense primer contained a KpnI recognition sequence (GGTAC↓C), and the antisense primer contained an XbaI recognition sequence (T↓CTAGA) at their respective 5' termini. Each of the PCR primers used for amplifying ASCT1 sequences had the following sequence:

```
ASCT1 sense primer:
5'-CGCGGGTACCGCCATGGAGAAGAGCAAC-3';  (SEQ ID NO:10)

ASCT1 antisense primer:
5'-CGCGTCTAGATCACAGAACCGACTCCTTG-3'. (SEQ ID NO:11)
```

PCR amplification was performed for 30 cycles, each cycle comprising 1 minute at 94° C., 30 seconds at 55° C. and 2 minutes at 72° C. Following the PCR, the product of the amplification reaction was purified using standard techniques (Saiki et al., 1988, Science 239: 487–491). The DNA then digested with the restriction enzymes KpnI and XbaI and then cloned into the polylinker of an oocyte transcription vector (pOTV; see Wang et al., 1991, Nature 352: 729–731) that had been digested with KpnI and XbaI. Synthetic RNA was then transcribed in vitro from this clone using the method of Kavanaugh et al. (1992, J. Biol. Chem. 267: 22007–22009) employing bacteriophage T7 RNA polymerase (New England Biolabs, Beverly, Mass.). 20–50 nL of ASCT1 RNA (at a concentration of about 400 µg/mL) was injected into defolliculated stage V–VI Xenopus oocytes excised from female *Xenopus laevis* anesthetized by immersion in 3-aminobenzoic acid for 60 min. Excised oocytes were treated with collagenase II (Sigma Chemical Co., St. Louis, Mo.) in calcium-free Barth's saline solution [comprising 88 mM NaCl, 1 mM KCl, 2.4 mM NaHCO$_3$, 0.82 mM MgSO$_4$, 7.5 mM Tris-HCl (pH 7.6), 50 U/mL Nystatin (Sigma) and 0.1 mg/mL gentamycin (Sigma)] for 60 min., and then incubated overnight at 15° C. in 50% Leibowitz's L-15 media (Grand Island Biological Co. (GIBCO), Long Island, N.Y.). After overnight incubation the oocytes were mechanically defolliculated and then were injected with ASCT-1 RNA and incubated at 19° C. for 48 h (see Kim et al., 1991, Nature 352: 725–728 for further details of Xenopus oocyte preparation and microinjection).

Amino acid transport in such oocytes was assayed using [$^3$H] alanine, [$^3$H] serine or [$^{35}$S] cysteine (obtained from New England Nuclear, Boston, Mass.). Briefly, microinjected oocytes were patch-clamped at −60 mV using a Dagan TEV-200 clamp amplifier with an Axon Instruments (Foster City, Calif.) TL-1 A/D interface controlled by pCLAMP software (Axon Instruments) (see Kavanaugh et al., 1992, J. Biol. Chem. 267: 22007–22009 for a detailed review of this methodology) and continuously superfused with ND-96 buffer (consisting of 96 mM NaCl/2 mM KCl/1.8 mM CaCl$_2$/1 mM MgCl$_2$/5 mM HEPES, pH 7.5). For transport measurements, this solution was changed to a solution containing varying concentrations of the radiolabeled amino acids in ND-96 buffer.

Figure 6B:
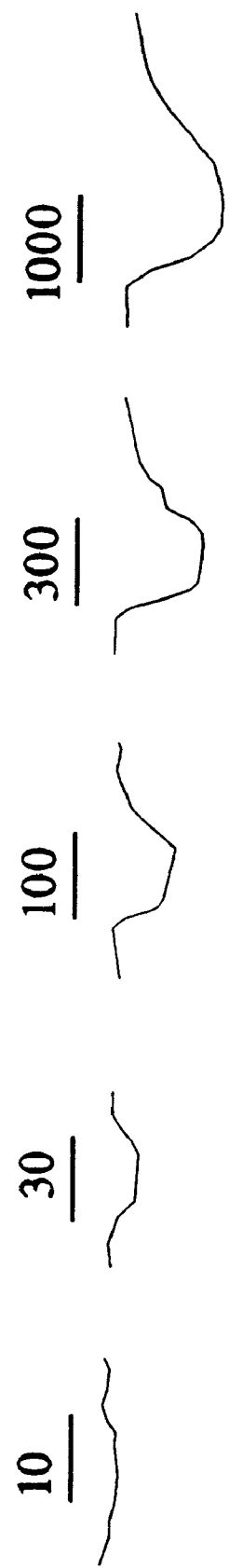
Figure 6C:
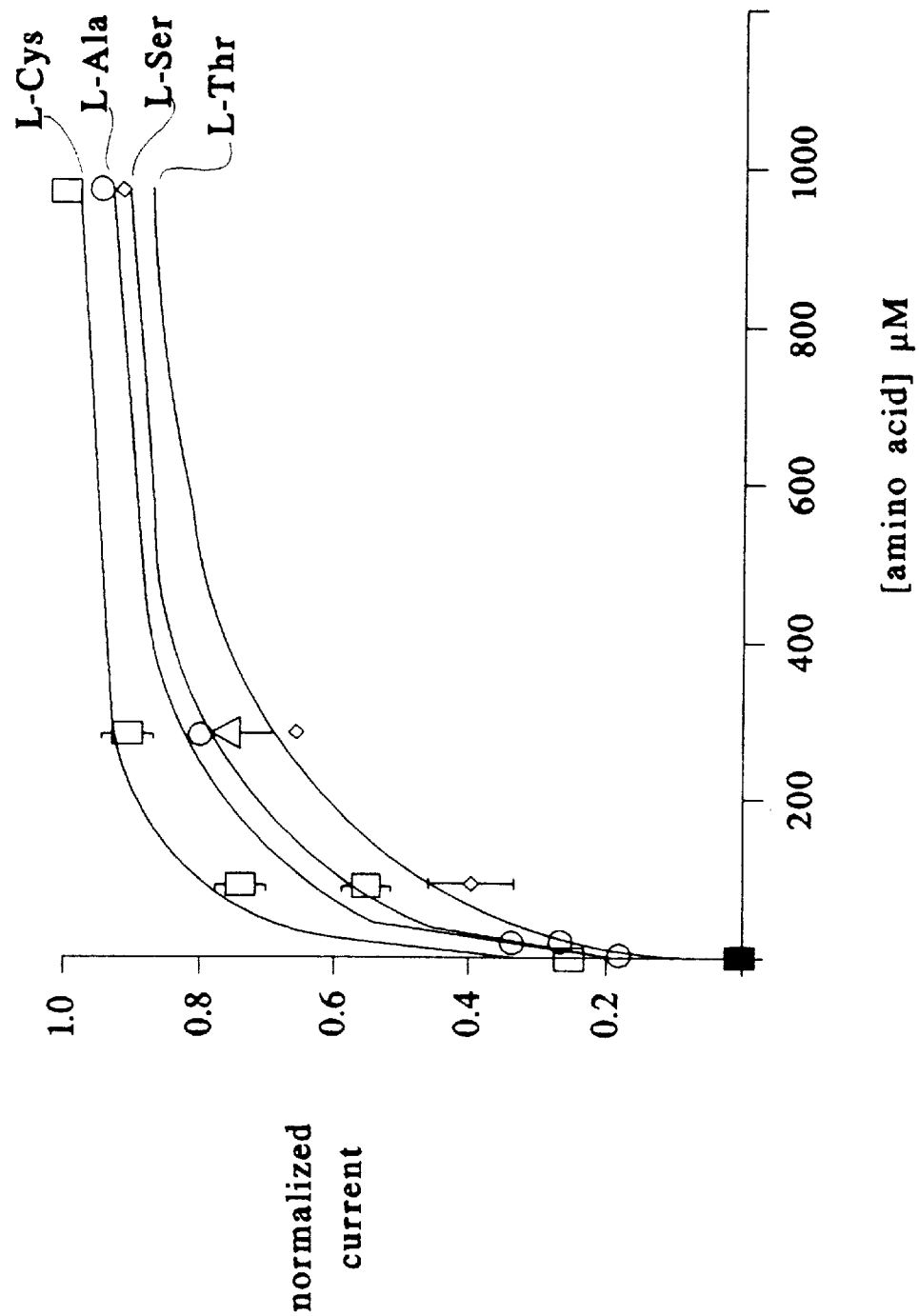

Three types of experiments were performed, the results of each being shown in FIGS. 6A through 6C. As shown in FIG. 6A, when such oocytes were contacted with ND-96 buffer containing L-alanine, L-serine or L-Cysteine, a hyperpolarization of the cell plasma membrane was produced as the result of inward currents of Na$^+$ ion, as has been associated with other known amino acid transporters (see Nicholls, ibid.). In contrast, the amino acids L-lysine, L-glutamine, proline, glycine, methionine, arginine, glutamine, asparagine, and leucine, and the amino acid analogues N-methylalanine, had no effect at much higher concentrations (i.e., about 1 mM). Another amino acid analogue, 2-methylaminoisobutyric acid (MAIB), which is known to be specific for the amino acid transporter type A (Christensen et al., 1967, J. Biol. Chem. 242: 5237–5246), also had no effect at concentrations of 1 mM. Further, in competition experiments, contacting such oocytes with a solution containing MAIB at a concentration of 10 mM had no effect on the rate of uptake of [$^3$H] alanine present at 100 µM. The response of the oocytes was also stereospecific (D-alanine was found to produce only 12±3% of the response produced by treatment of these oocytes with L-alatine) and Na$^+$ ion-specific (no response was detected when Na$^+$ ions were replaced by tris-hydroxyethylaminomethane buffer, shown in FIG. 6A). The rate of radiolabeled amino acid uptake (in pmol/min per oocyte, determined at an amino acid concentration of 100 µM) for the amino acids alanine, cysteine and serine are shown in Table I.

The uptake currents measured in ASCT1-injected oocytes were found to be both dose-dependent and saturable. FIG. 6B illustrates the dose-dependency of the electrochemical response of ASCT 1-injected oocytes to L-alanine. The intensity of the response (equivalent to the amount of current flow into the cell) increased with the concentration of L-alanine from 10µM to 1 mM. The saturability of this response is shown in FIG. 6C. In this Figure, the current, normalized to the maximum response obtained with L-alanine, is shown plotted against the extracellular amino acid concentration of each amino acid tested. For the L-stereoisomers of alanine, serine, cysteine and threonine, the inward current flux was found to saturate and reach a plateau at concentrations from 400–1000 µM. More detailed analyses of the kinetics of amino acid influx were performed by least squares linear regression analysis of induced inward current ([I]) plotted as a function of substrate amino acid concentration ([S]), using the equation shown in the legend of Table II. Data were averaged from all oocytes tested, and the results expressed as the mean±standard error are shown in Table II.

These results indicated that the cloned ASCT1 cDNA derived from human motor cortex mRNA encoded an amino acid transporter that was specific for Alanine, Serine, Cysteine (and Threonine) and that amino acid transport activity was accompanied by an inward current flow mediated by sodium ions. These results demonstrated that the novel amino acid transporter isolated herein was related to but distinct from other, known transporters, such as the so-called ASC amino acid transporters (Christensen et al., ibid.).

EXAMPLE 4

Functional Expression of the Glutamate Amino Acid Transporter Genes in Xenopus Oocytes Similar series of experiments were performed using RNA synthesized in vitro from constructs containing each of the cloned glutamine transporter genes of the invention. In these experiments, each of the PCR primers used to amplify each of the glutamate transporter genes had the following sequence:

EAAT1 sense primer:
(SEQ ID NO:12)
5'-CGCGGGTACCAATATGACTAAAAGCAATG-3';

EAAT1 antisense primer:
(SEQ ID NO:13)
5'-CGCGTCTAGACTACATCTTGGTTTCACTG-3';

EAAT2 sense primer:
(SEQ ID NO:14)
5'-CGCGGGTACCACCATGGCATCTACGGAAG-3';

EAAT2 antisense primer:
(SEQ ID NO:15)
5'-CGCGTCTAGATTATTTCTCACGTTTCCAAG-3';

EAAT3 sense primer:
(SEQ ID NO:16)
5'-CGCGGGTACCGCCATGGGGAAACCGGCG-3';

EAAT3 antisense primer:
(SEQ ID NO:17)
5'-CGCGGGATCCCTAGAACTGTGAGGTCTG-3'.

As can be determined by inspection of these sequences, each of the sense primers contained a KpnI recognition sequence (GGTAC↓C), and each of the antisense primers contained an XbaI recognition sequence (T↓CTAGA) at the 5' terminus of each primer for EAAT1 and EAAT2. For EAAT3, the sense primer contained a KpnI recognition sequence, and the antisense primer contained a BamHI recognition sequence (G↓GATCC) at the 5' terminus of each primer.

PCR amplification was performed for 30 cycles, each cycle comprising 1 minute at 94° C., 30 seconds at 50° C. and 2 minutes at 72° C. Following the PCR, each of the PCR products was isolated and cloned into pOTV as described in Example 3, from which RNA encoding each glutamate transporter was synthesized in vitro as described.

Figure 12A:
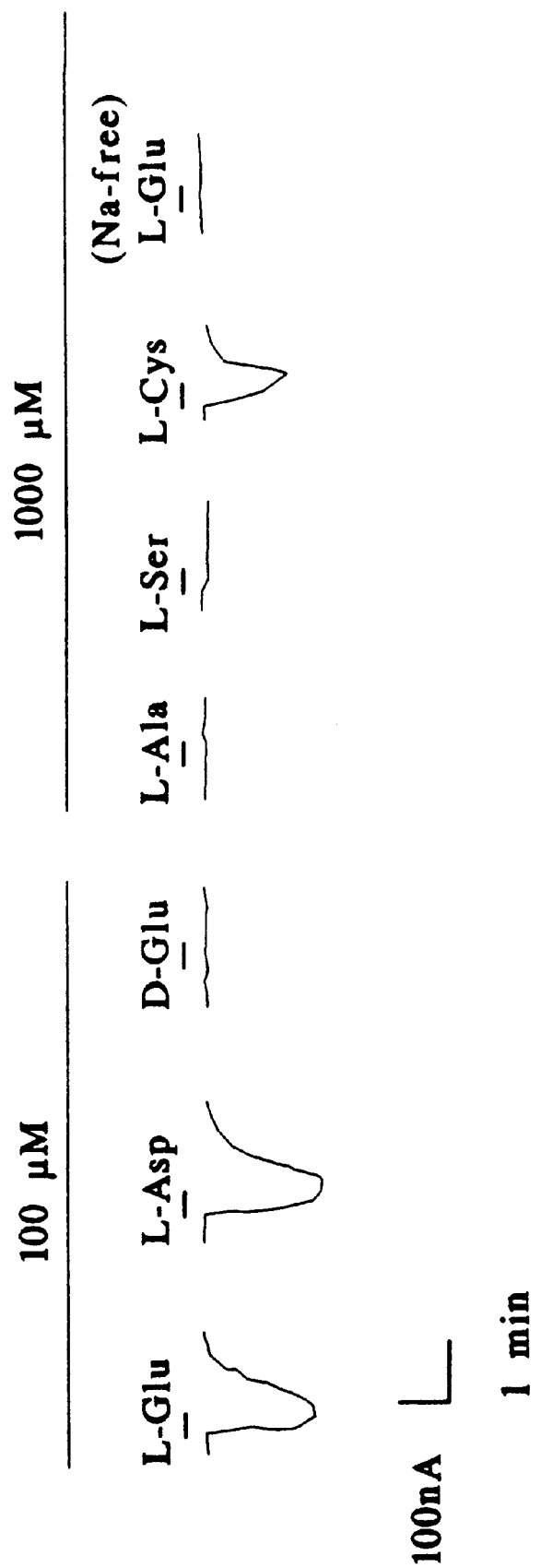
FIGS. 12A through 12C illustrate electrogenic uptake of various amino acids (FIG. 12A) and the concentration dependence of such uptake of L-glutamate (FIGS. 12B and 12C) in *Xenopus laevis* oocytes expressing the EAAT1 amino acid transporter.
Figure 12B:
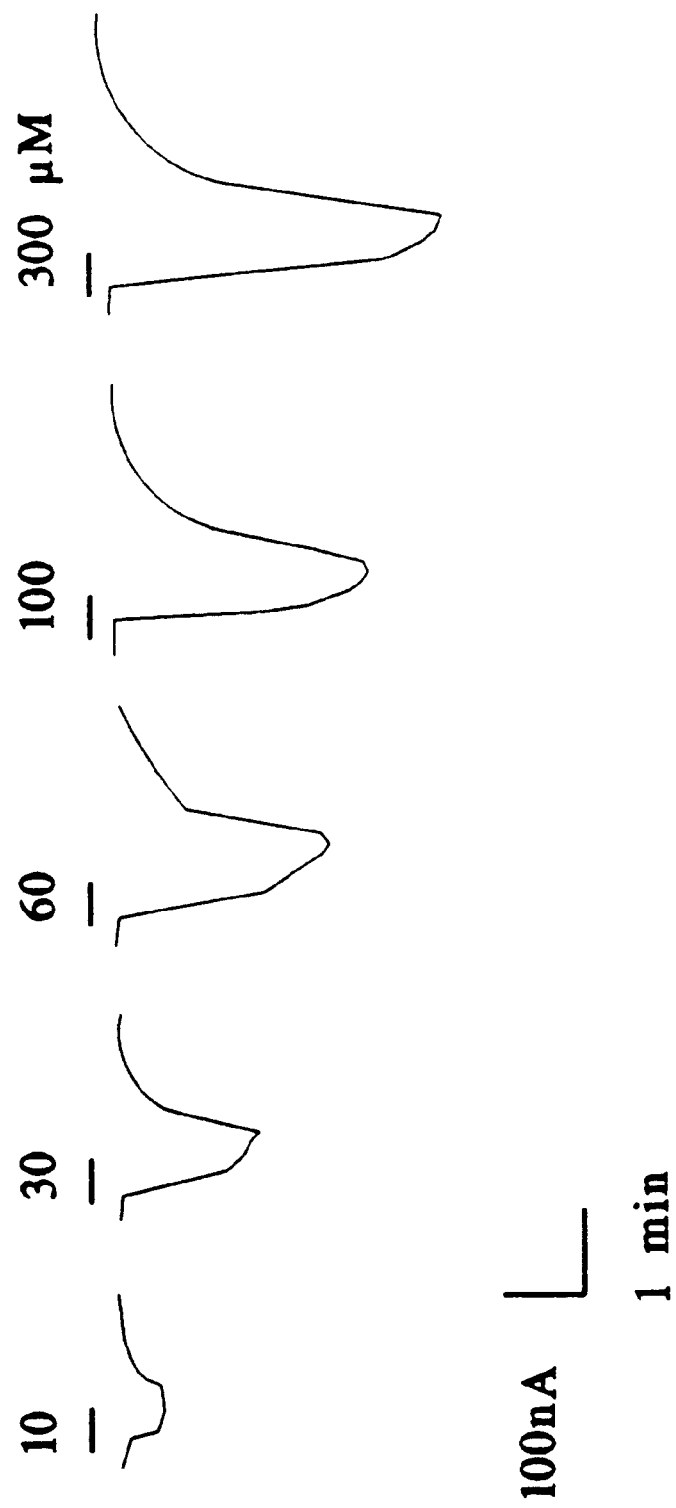
Figure 12C:
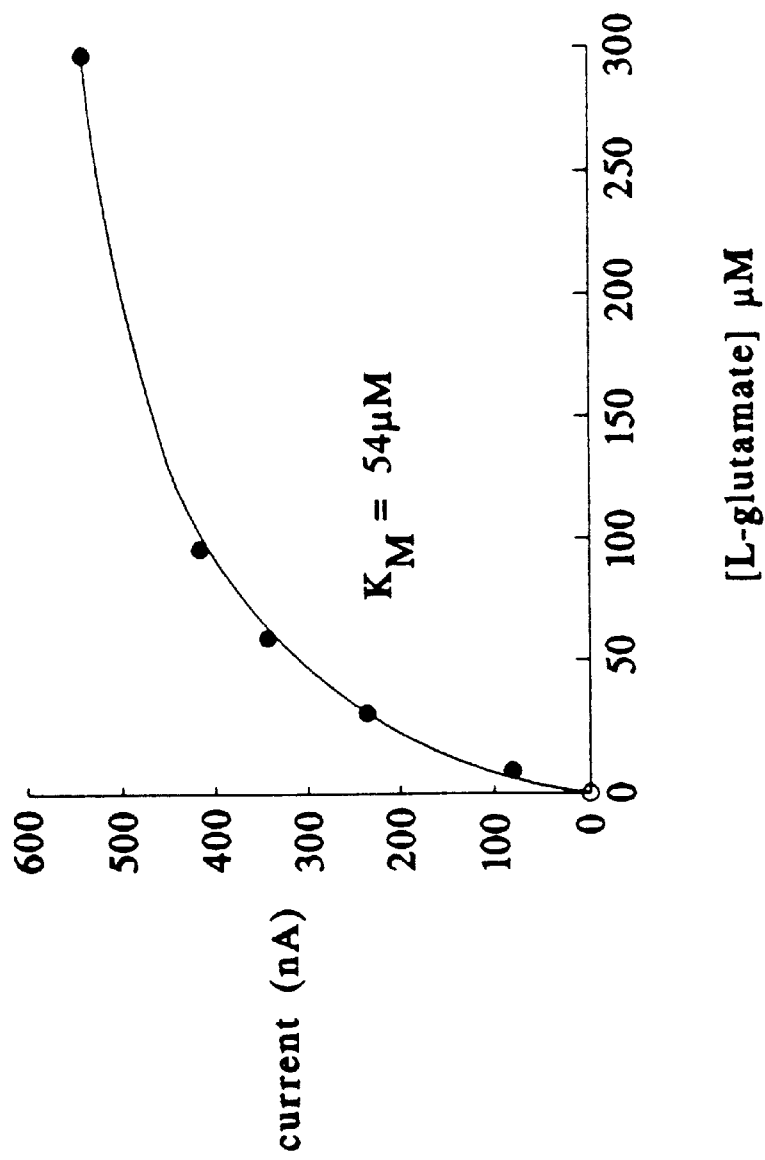

Such RNA preparations were each introduced into Xenopus oocytes as described in Example 3 to enable expression therein. Amino acid uptake experiments were performed on such oocytes expressing each of the glutamate transporters, also as described in Example 3. Results of such experiments are shown in FIGS. 12A through 12C. FIG. 12A shows electrogenic uptake of various amino acids in EAAT1-expressing oocytes. Both L-glutamate and L-aspartate caused inward currents as high as several microamps when added to the incubation media (ND-96) at a concentration of 100 $\mu$M. In contrast, incubation of EAAT1-expressing oocytes with L-alanine and L-serine at ten-fold higher concentrations (i.e., 1000 $\mu$M) did not result in electrogenic uptake of these amino acids. Uptake was found to be stereospecific, since L-glutamate incubation did not result in the generation of an inward electric current, and sodium-ion specific, since electrogenic uptake of L-glutamate was abolished by incubation in sodium ion-free media (choline was used to replace sodium in these incubations).

These experiments also demonstrated the surprising result that cysteine, when present at high enough extracellular concentrations (i.e., 1000 $\mu$M) was capable of being electrogenically transported by the EAAT1 transporter. Cysteine had not previously been reported to be a glutamate transporter substrate; however, amino acid sequence analysis of the EAAT1 transporter showed structural similarities between EAAT1 and the ASCT1 transporter, which was demonstrated herein to transport cysteine (see Example 3). As will be discussed in detail below, the EAAT1 transporter displays a $K_m$ for glutamate of 54 $\mu$M; in contrast, the $K_m$ for cysteine was found to be 300 $\mu$M. The EAAT1 transporter thus displays a pattern of substrate specificity that is distinct from that of any known glutamate transporter.

FIGS. 12B and 12C illustrate the results of biochemical analysis of substrate affinity of the EAAT1 transporter for glutamate, said results being plotted as current versus substrate concentration to yield an estimate of the $K_m$. These experiments were performed essentially as described for the ASCT1 transporter in Example 3. Patch-clamped oocytes expressing the EAAT1 transporter were incubated with varying extracellular concentrations of L-glutamate, and the magnitude of the resulting inward currents determined. From these experiments, the plotted relationship between the magnitude of the inward current and the extracellular L-glutamate concentration was determined, resulting in an estimate for $K_m$ equal to 54 $\mu$M for L-glutamate. These results were in good agreement with results obtained in COS-7 cells expressing the EAAT1 transporter, described hereinbelow (see Example 5).

EXAMPLE 5

Functional Expression of the Amino Acid Transporter Genes in COS-7 Cells

DNA fragments comprising the coding sequences of the novel glutamate transporter genes of the invention were excised from the pOTV constructs described in Example 3 and subcloned into the mammalian expression plasmid pCMV5 (Anderson et al., 1989, J. Biol. Chem. 264: 8222–8229). These mammalian expression constructs were used for transient expression assays of glutamate transporter protein function after transfection of each of these constructs into COS-7 cells (Gluzman, 1981, Cell 23: 175–182).

Each of the pCMV5 constructs corresponding to EAAT1, EAAT2 and EAAT3 were introduced into COS-7 cells by DEAE-dextran facilitated transfection (see Sambrook et al., ibid.). Two day following transfection, the transfected cells were washed three times in phosphate-buffered saline (PBS) and then incubated with a mixture of radiolabeled amino acid ([$^3$H]-L-glutamate or [$^3$H]-D-aspartate; Dupont-NEN) and non-radiolabeled amino acid for 10 min. After incubation, the cells were washed three times with ice-cold PBS, solubilized with a solution of 0.1% sodium dodecyl sulfate (SDS) and the amount of radioactivity associated with the cells determined using standard liquid scintillation counting methods. The results of these experiments showed that cells transfected with each of the glutamate transporter constructs accumulated significantly-higher (between 10- and 100-fold higher) amounts of radioactivity than did mock (i.e., pCMV5 plasmid) transfected COS-7 cells (which accumulation represented endogenous COS-7 cell uptake of radioactive glutamate). The course of radioactive glutamate uptake was found to be linear for at least 20 min in assays performed at room temperature.

Figure 7A:
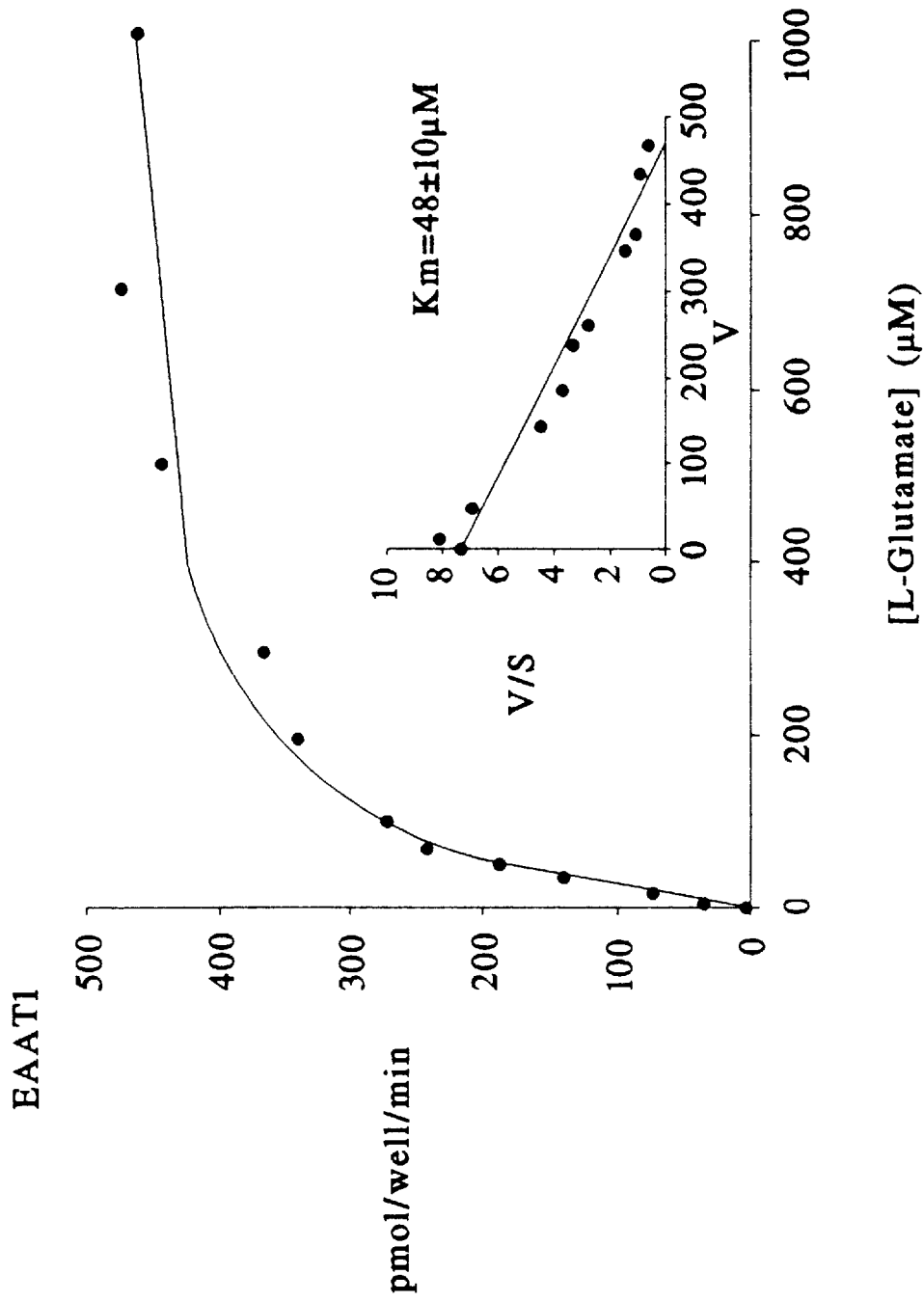
FIGS. 7A through 7F present glutamate transporter kinetics of EAAT1 (FIGS. 7A and 7B), EAAT2 (FIGS. 7C and 7D) and EAAT3 (FIGS. 7E and 7F).
Figure 7B:
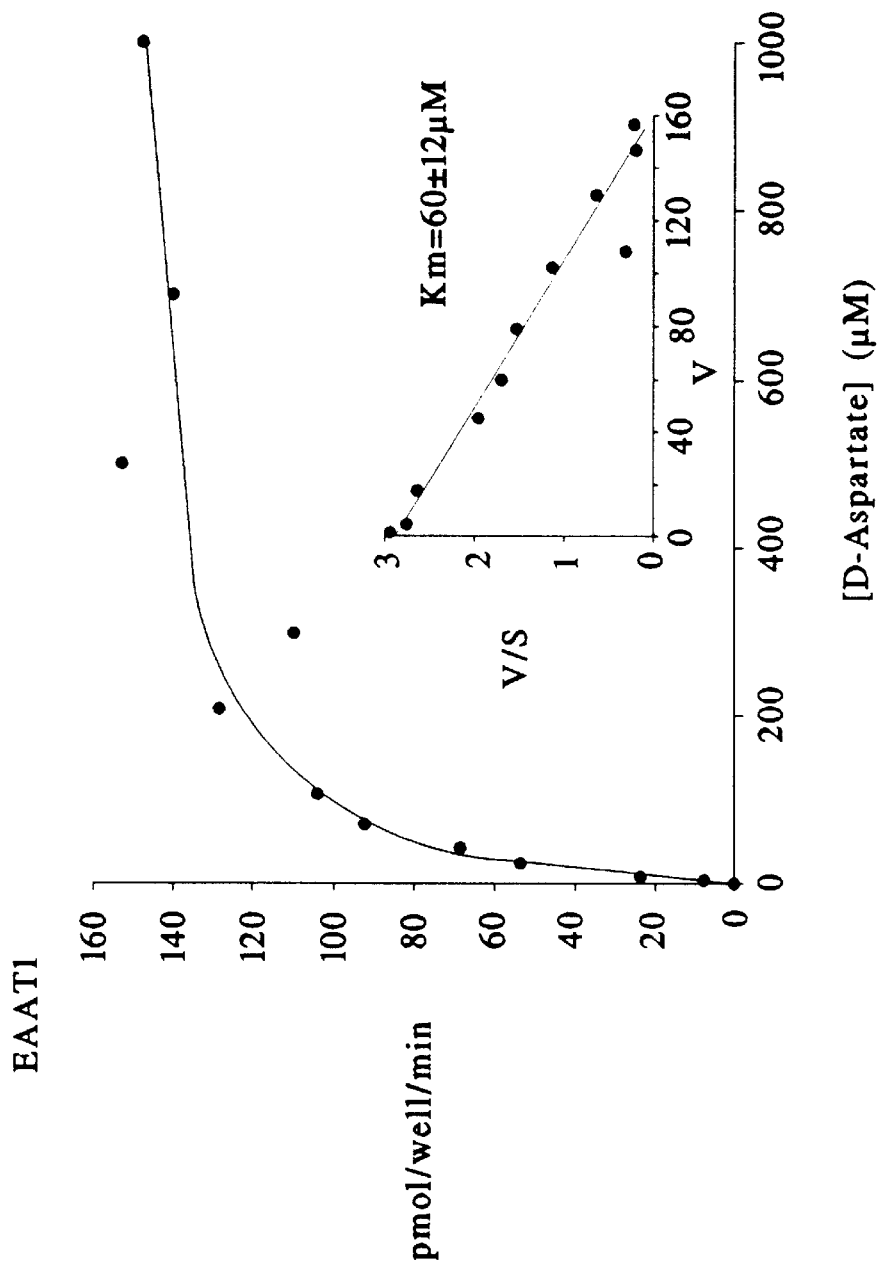
Figure 7C:
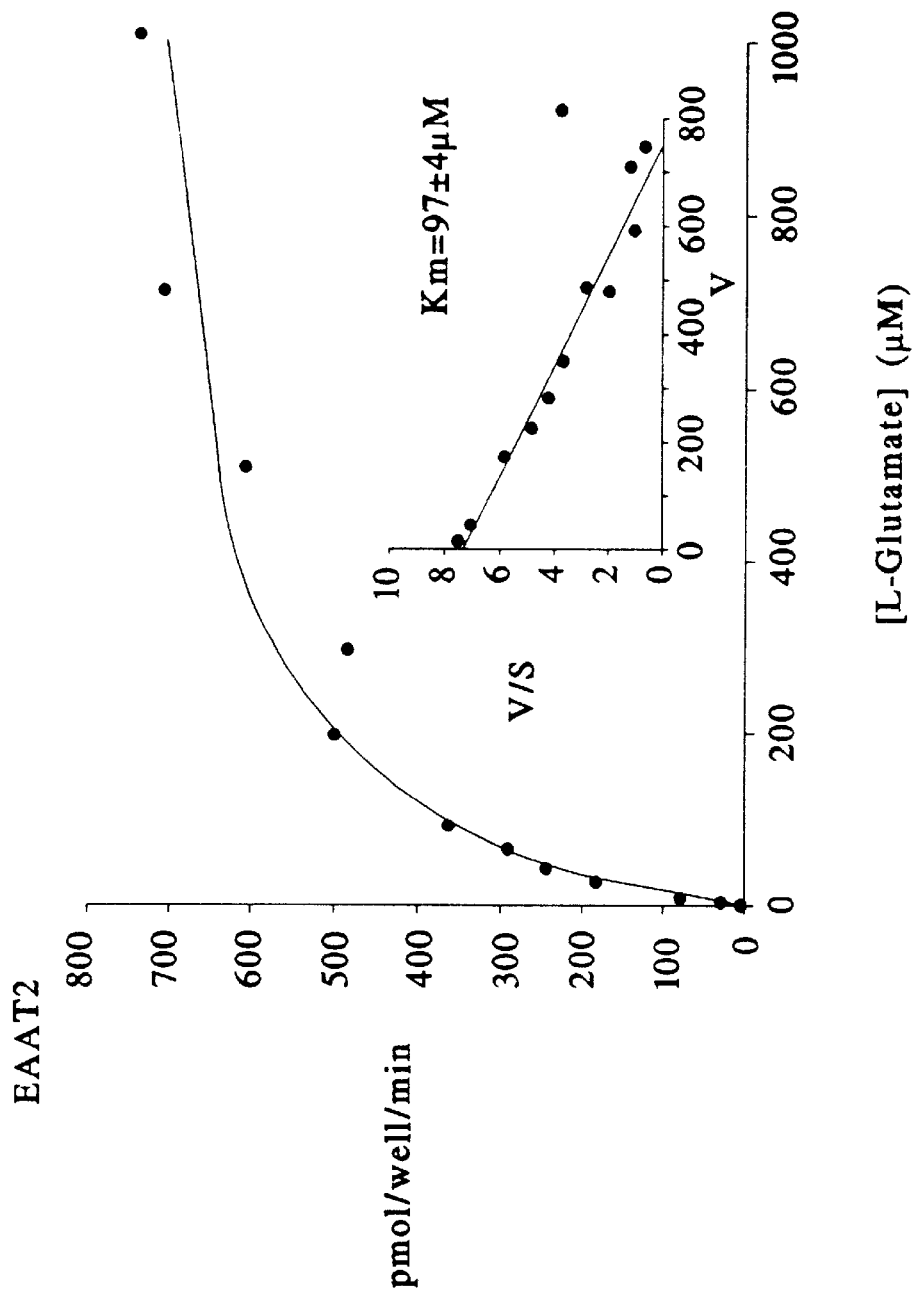
Figure 7D:
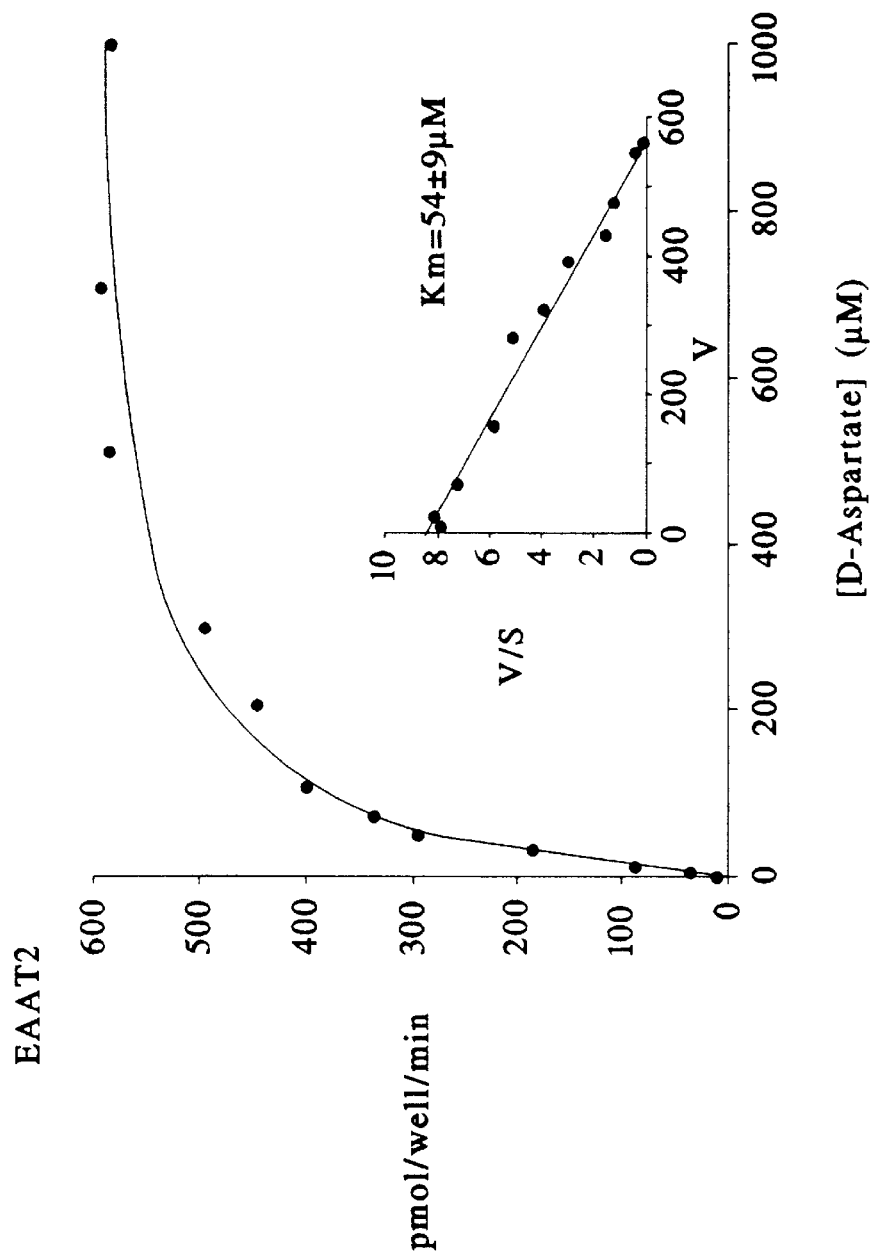
Figure 7E:
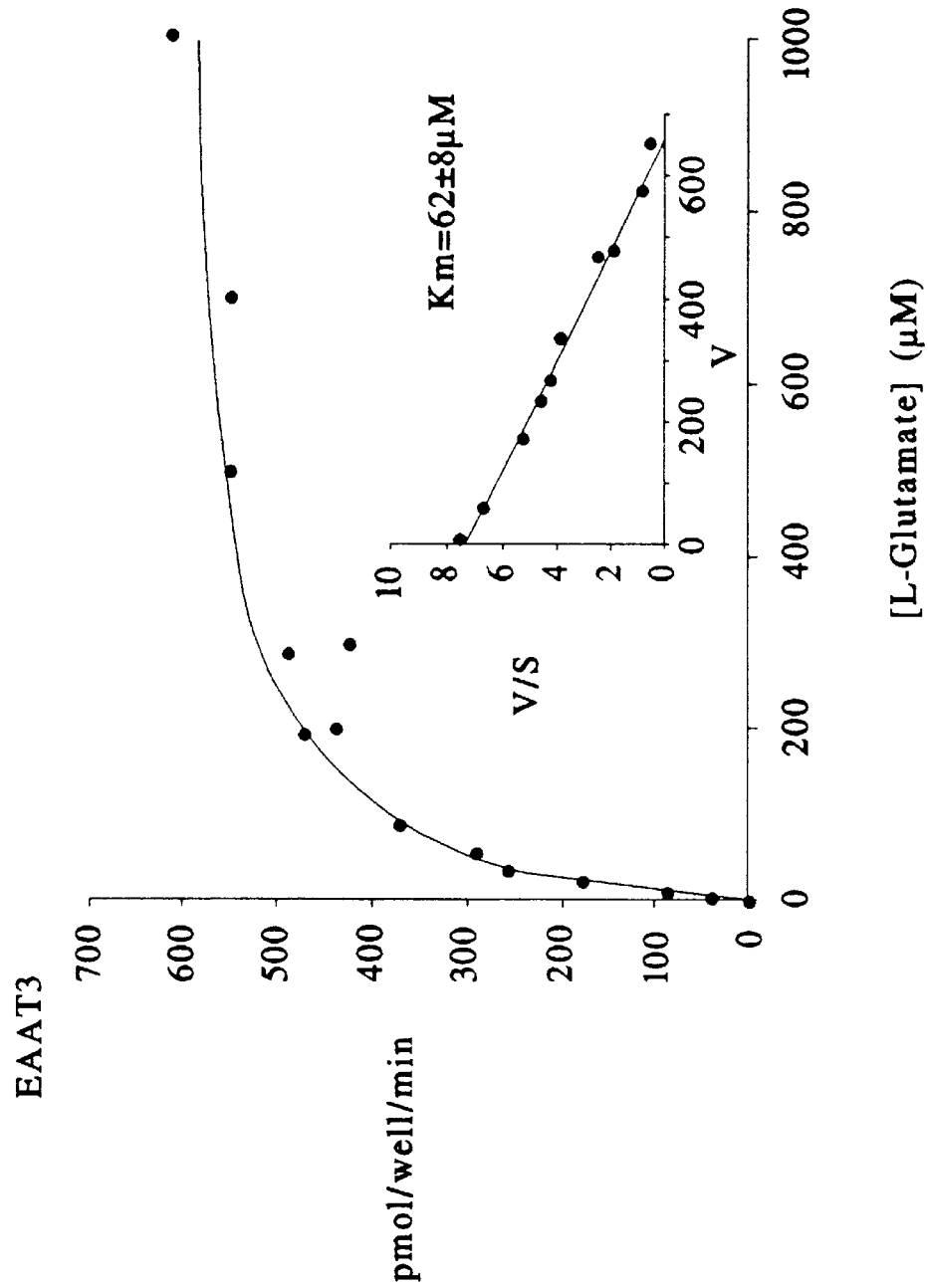
Figure 7F:
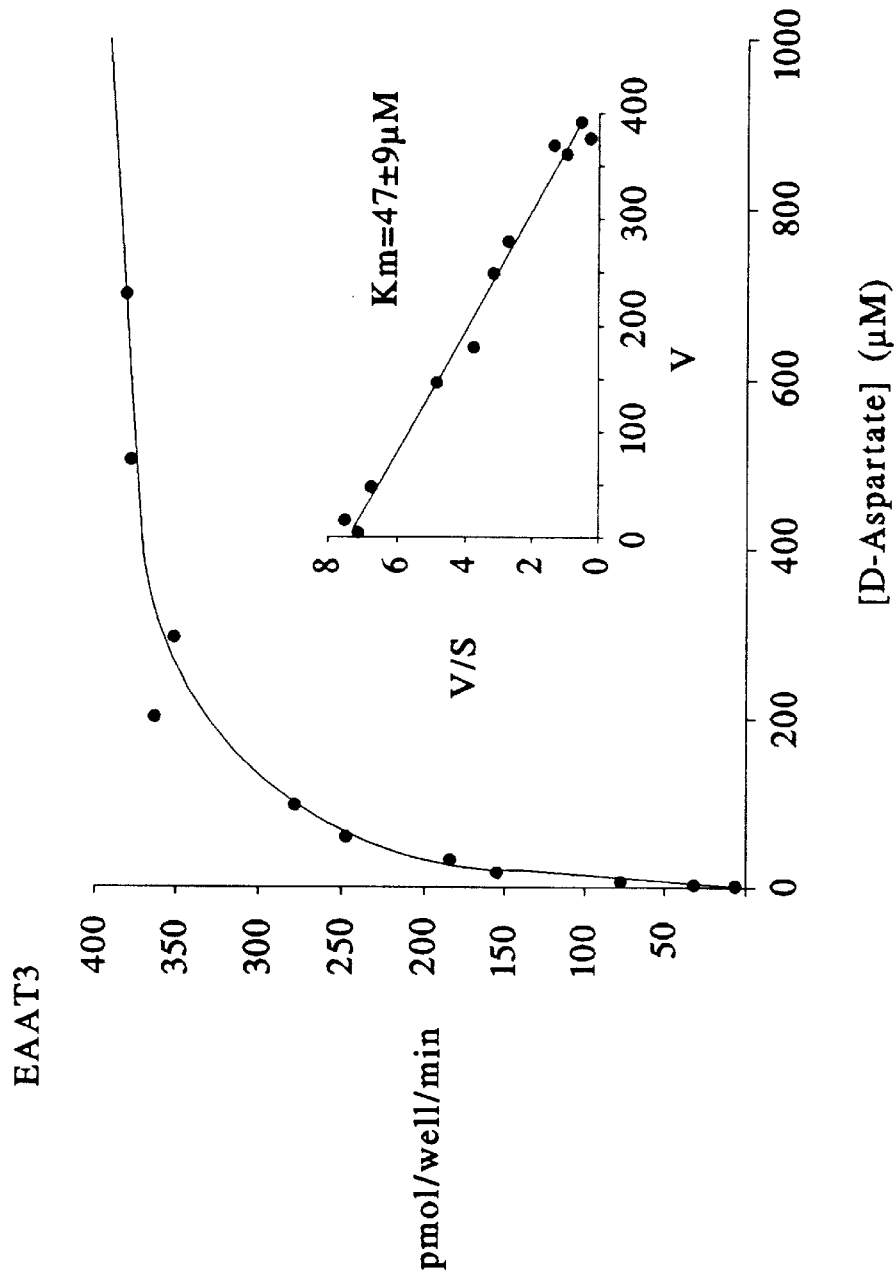

These results are shown in FIGS. 7A through 7F. In the Figure, EAAT1 transporter kinetics of glutamate uptake are depicted in FIG. 7A and of aspartate are shown in FIG. 7B. Similarly, EAAT2 kinetics for glutamate and aspartate are shown in FIGS. 7C and 7D, respectively. Finally, EAAT3 kinetics are shown in FIG. 7E (glutamate) and FIG. 7F (aspartate). Each data point was determined by incubating a COS cell culture transfected with the appropriate pCMV5-glutamate transporter clone with 100 nM of radiolabeled amino acid and increasing amounts of unlabeled amino acid. Results are plotted as uptake velocity (in pmol/cell culture/min) minus endogenous uptake versus total amino acid concentration, and each data point was performed in triplicate. The results show that both glutamate and aspartate uptake mediated by each of the three novel human glutamate transporters is saturable. Insets in each Panel depict Eadie-Hofstee plots of initial velocity data, from which $K_m$ values were determined. The $K_m$ values are shown as the mean±standard error based on at least three independent experiments. These results show that each of the three novel transporter proteins comprising the instant invention is functionally competent as an amino acid transporter when expressed in a culture of mammalian cells, and that each of the novel transporters encoded by the cDNA clones EAAT1, EAAT2 and EAAT3 displays a collection of biochemical properties consistent with their designation as human glutamate transporter proteins.

EXAMPLE 6

Inhibitor Potency Analyses Using COS7 Cells Expressing Amino Acid Transporter Proteins COS-7 cell cultures transformed with pCMV5-human glutamate transporter constructs as described in Example 4 were used to characterize the pharmacological properties of each of these transporter proteins relative to a variety of known glutamate transporter inhibitors. These assays were performed essentially as described in Example 4, with the exception that varying amounts of each of a number of known inhibitor compounds were included in the incubations.

Figure 8A:
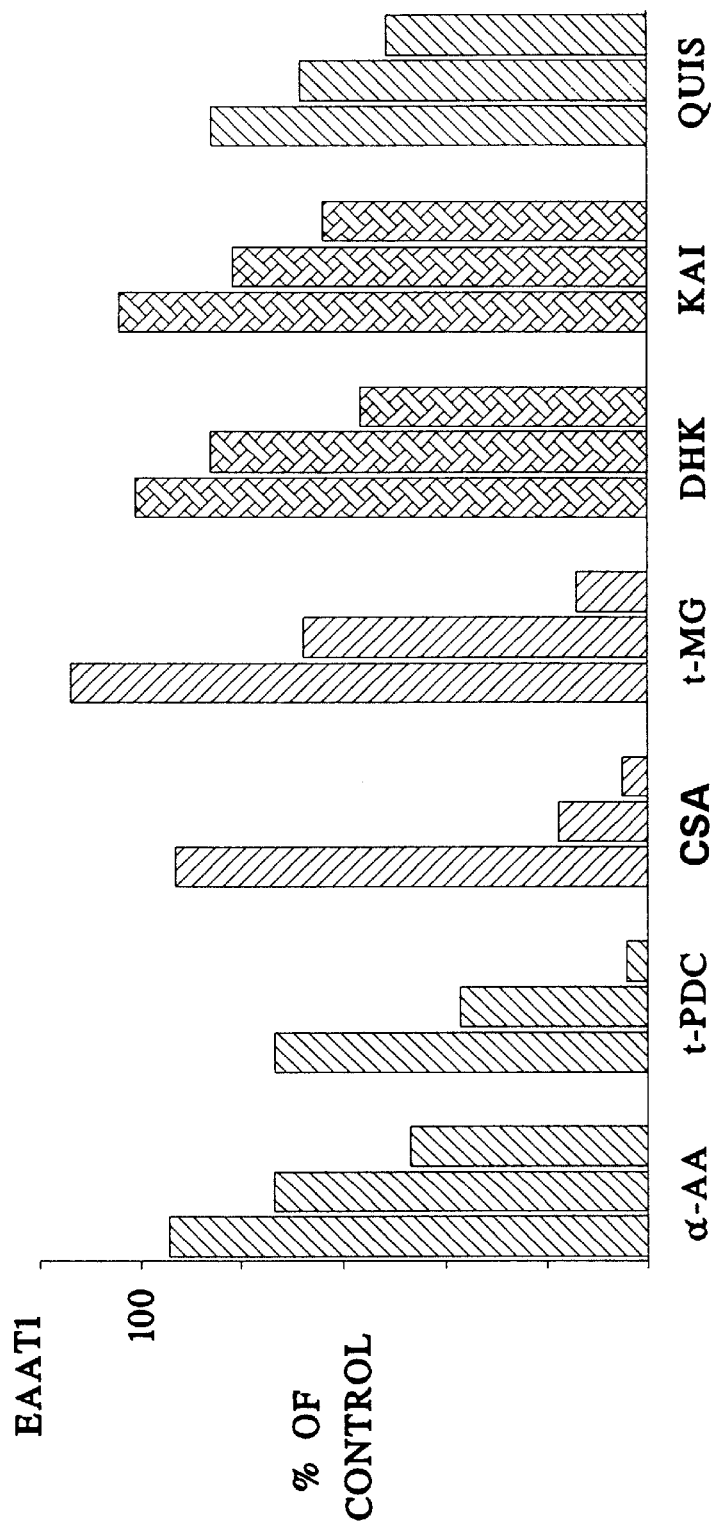
FIGS. 8A through 8C represent the pharmacological responsiveness of glutamate transport by the human excitatory amino acid transporters EAAT1, EAAT2 and EAAT3 when contacted with the indicated competitors/inhibitors at 1 $\mu$M L-glutamate and inhibitor/competitor concentrations of 3 $\mu$M, 100 $\mu$M or 3 mM.
Figure 8B:
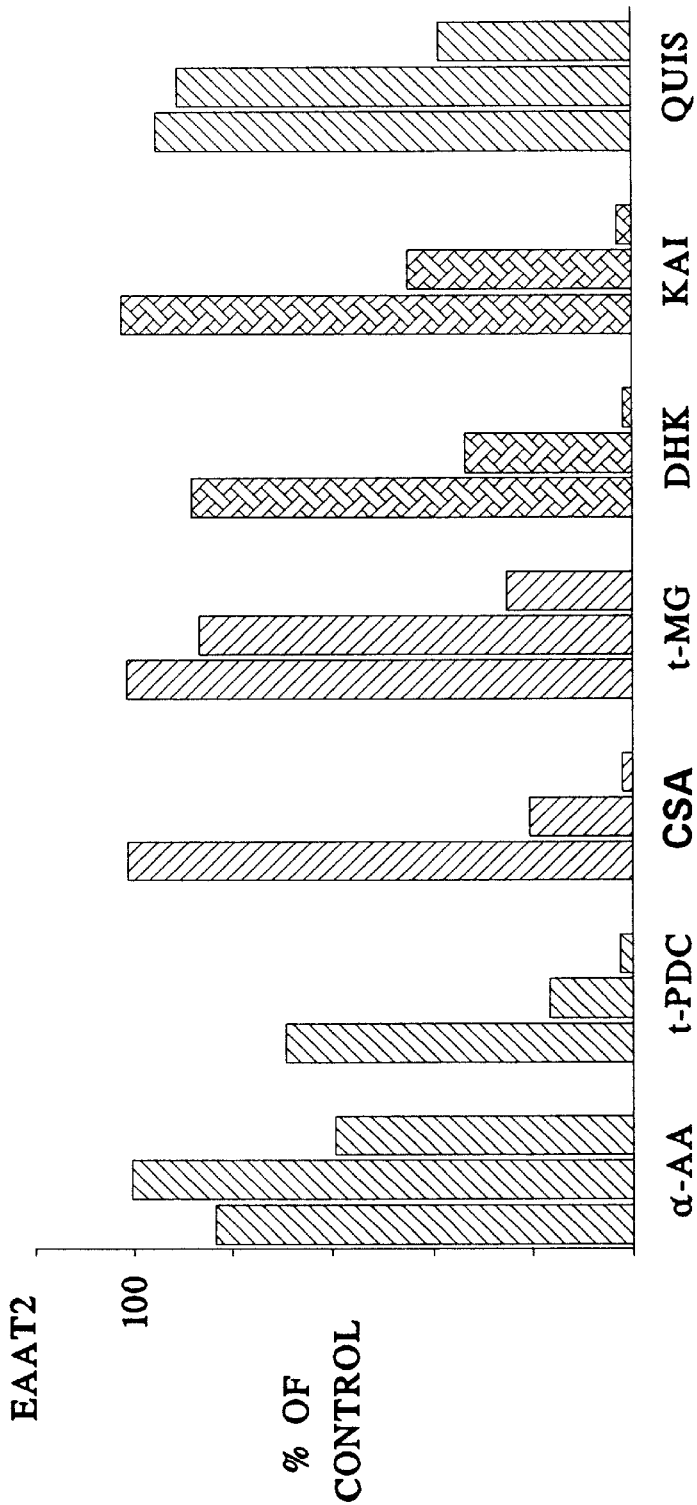
Figure 8C:
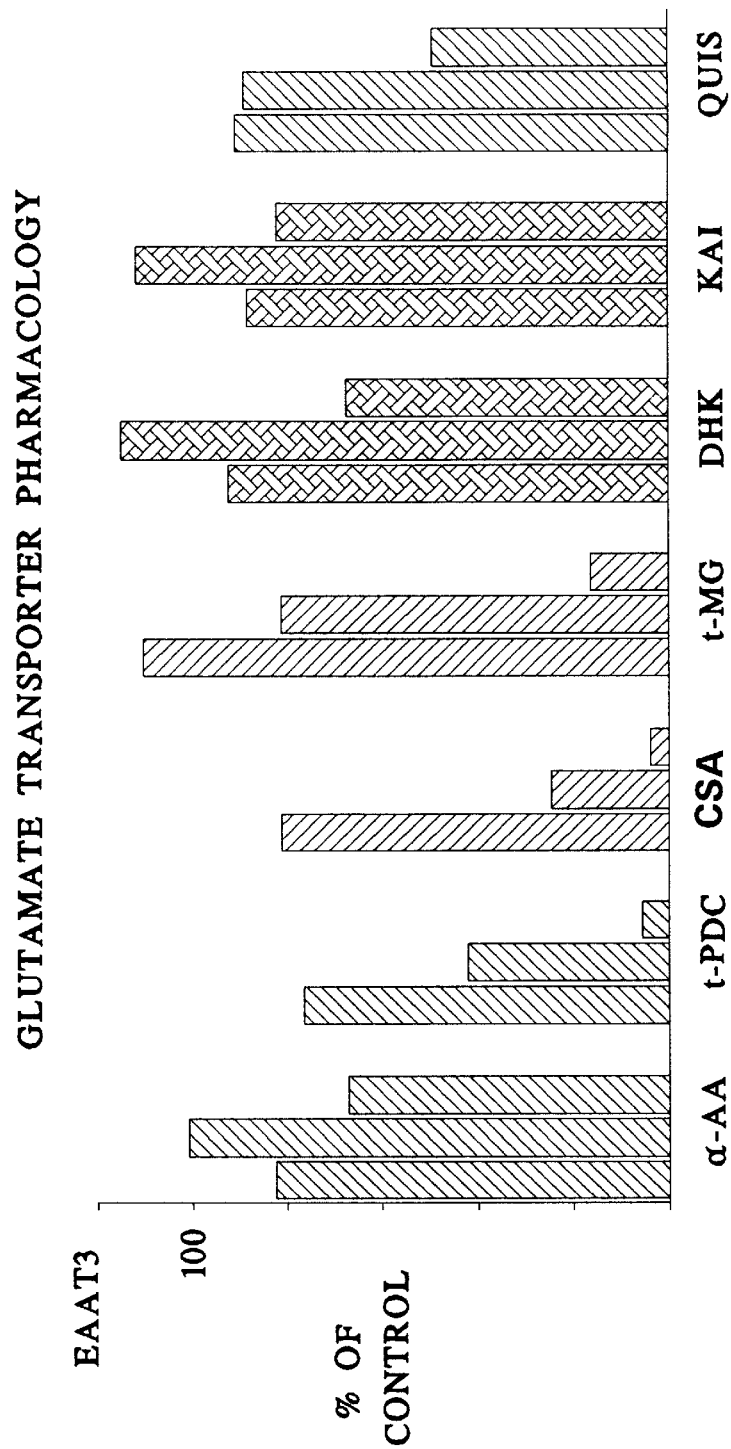

The results of these experiments are shown in FIGS. 8A through 8C. The data in FIGS 8A through 8C represent the pharmacological responsiveness of glutamate transport by the human excitatory amino acid transporters EAAT1, EAAT2 and EAAT3 when contacted with the following competitors/inhibitors: L-threo-β-hydroxyaspartate (THA); L-trans-pyrrolidine-2,4-dicarboxylate (PDC); L-serine-O-sulfate (SOS); dihydrokainate (DHK); and kainate (KAI). In these experiments, uptake of 1 μM of [$^3$H]-L-glutamate was determined in the presence of the indicated amounts of each of the inhibitors. As can be seen from the Figures, each of the glutamate transporter proteins of the invention displays a characteristic pattern of sensitivity to the inhibitors. Thus, the relative potency of inhibition of radiolabeled glutamate uptake was found to be as follows for the EAAT1 and EAAT3 transporter proteins:

THA<PDC<SOS<<DHK, KAI, whereas the inhibition pattern for EAAT2 was as follows:

PDC<THA<DHK<KAI<SOS.

These results, as well as results obtained from similar experiments performed with L-cysteate, L-Cysteine sulfinic acid, β-glutamate and L-aspartate-β-hydroxymate, are shown in Table III. Even though the relative pattern of inhibition was the same for EAAT1 and EAAT3, the results shown in the Table support the finding that each of the glutamate transporters of the invention is uniquely characterized by its sensitivity to this panel of glutamate uptake inhibitors.

In addition, a number of reported inhibitors were found to be ineffective when tested with COS cell culture expressing each of the novel glutamate transporter proteins of the invention. These include cis-1-aminocyclobutane-1,3-dicarboxylate, L-pyroglutamic acid, S-sulfo-L-cysteine, N-acetyl aspartylglutamate, N-methyl-D-aspartate (NMDA) and quisqualate. α-aminoadipate, a classical inhibitor of glutamate uptake, exhibited only low potency when tested against all three EAAT subtypes. These results of functional assays support the conclusion arrived at from structural analysis (i.e., nucleic acid and amino acid sequence analyses) that the glutamate transporter cDNAs and proteins of the invention are novel mammalian transporter species.

EXAMPLE 7

Tissue Distribution of Amino Acid Transporter Expression

The tissue distribution of mRNA corresponding to expression of the amino acid transporters disclosed herein was determined in various tissues by Northern hybridization experiments (see Sambrook et al., ibid.). The results of these experiments are shown in FIGS. 9 and 10.

A panel of tissue samples was examined by Northern hybridization analysis performed under high stringency conditions as follows. A nylon filter containing 2 μg human peripheral tissue poly(A)$^+$ RNA was obtained from Clonetech Laboratories (Palo Alto, Calif.), and a similar filter was prepared containing human brain region RNA as follows. Total RNA was isolated from human brain region tissue obtained from the Oregon Brain Repository and 20 μg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with $^{32}$P-labeled amino acid transporter-specific probes for each transporter to be analyzed. Probes were derived from amino acid transporter coding sequences and labeled using $^{32}$P-labeled dCTP by the random primer method (Boehringer-Mannheim, Indianapolis Ind.). Filters were hybridized overnight at 42° C. individually with each radiolabeled probe (at a concentration of 10$^6$ cpm/mL) in a solution of 5×SSPE/50% formamide/7.5×Denhardt's solution (comprising 0.15 g/100 mL each of Ficoll, polyvinylpyrrolidone and bovine serum albumin)/2% SDS and 100 μg/mL denatured salmon-sperm DNA. Following hybridization, filters were washed twice for 30 min at room temperature in 2×SSPE/0.1% SDS and twice for 20 min at 50° C. in 0.1×SSPE/0.1% SDS. Hybridizing RNAs were visualized by autoradiography at −70° C. using intensifying screens. The filters were subsequently re-probed as described with a radiolabeled human β-actin probe (Clonetech) as a positive control.

Figure 9:
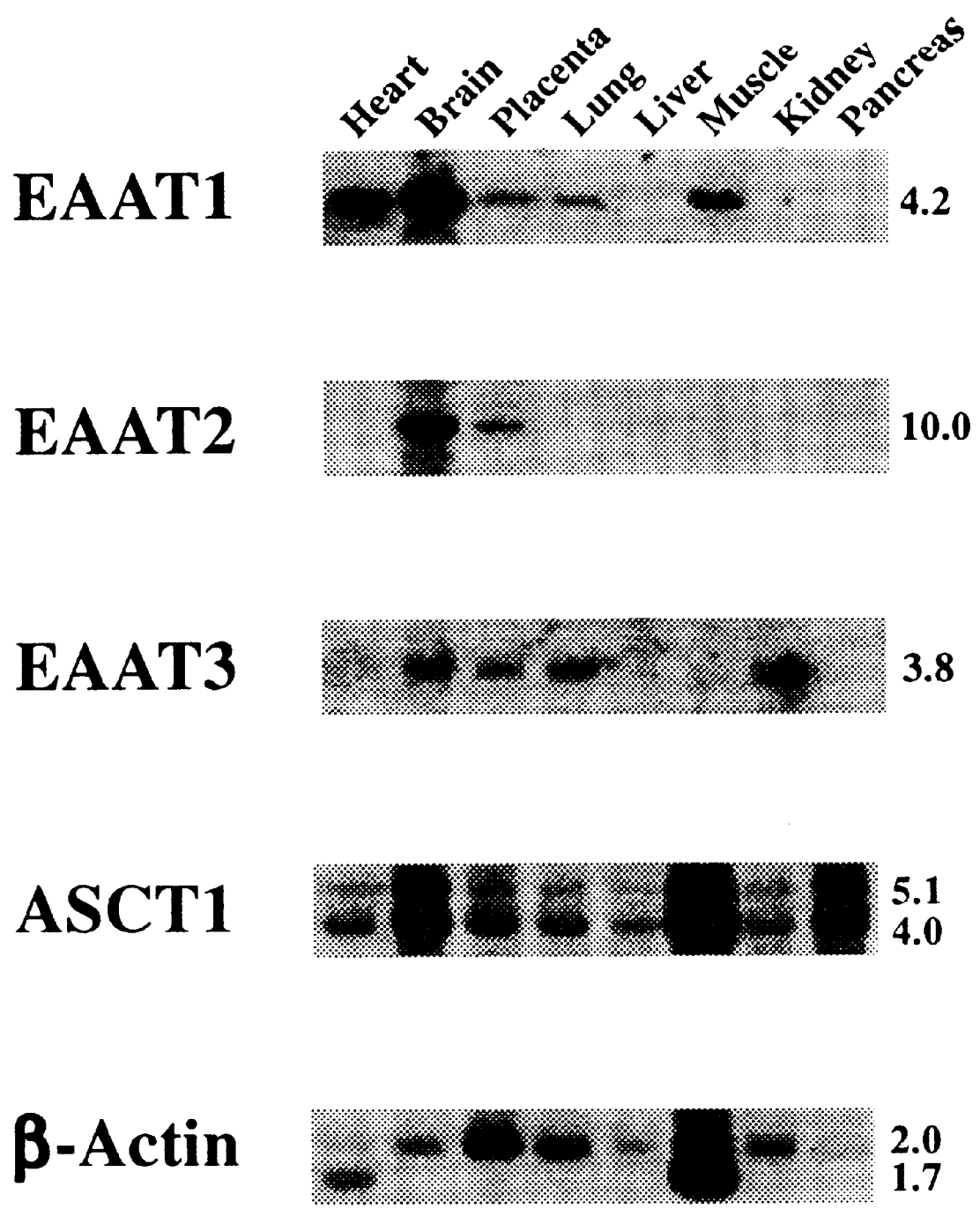
FIG. 9 shows the pattern of expression of EAAT1, EAAT2, EAAT3 and ASCT1 in human tissues; β-actin is shown as a control for amount of RNA in each lane.
Figure 10:
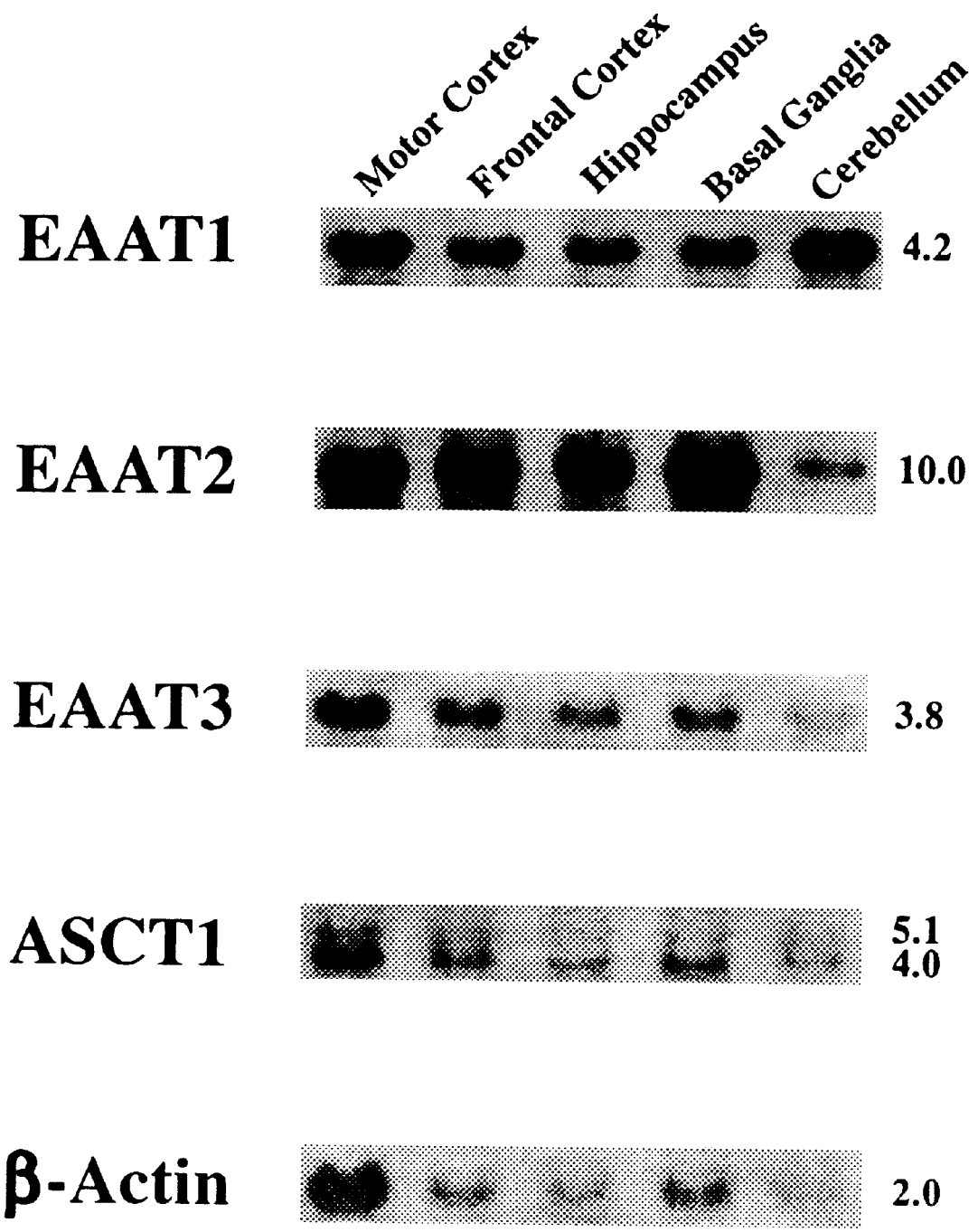
FIG. 10 shows the pattern of expression of EAAT1, EAAT2, EAAT3 and ASCT1 in human brain tissue; β-actin is shown as a control for the amount of RNA in each lane.

The results of these experiments are shown in FIGS. 9 and 10. FIG. 9 illustrates expression of each of the amino acid transporters in human heart, brain, placenta, lung, liver, muscle, kidney and pancreas. The size (in kb) of the transcripts corresponding to expression of each transporter are displayed along the right-hand border of each panel. As is seen from these autoradiographs, EAAT1 is expressed predominantly in brain, heart and muscle, to a lesser extent in placenta and lung, weakly in liver, and at levels below the ability of this assay to detect in kidney and the pancreas (if at all). EAAT2 is expressed in brain, and to a lesser extent in placenta; expression was not detected in any other tissue tested. EAAT3 is expressed predominantly in the kidney, but significant expression was also detected in brain, placenta, and lung. ASCT1 is expressed in all tissues tested as at least one of three differently-sized transcripts, possibly corresponding to differential RNA processing during expression of this transporter (which result might be due in the alternative to the utilization of alternative polyadenylation sites found in the 3' untranslated region). These results demonstrate that the amino acid transporters disclosed herein are encoded by separate and distinct, albeit related, genes and that each transporter has a unique pattern of tissue-specific expression.

FIG. 10 shows the distribution of these amino acid transporter transcripts in different human brain regions. Varying expression levels were found for each of the amino acid transporters in all brain regions examined. These results support the conclusion that the amino acid transporters of the invention may play an important role in normal brain function, and that disruption of amino acid transport by these transporter may be important determinants in organic brain dysfunction, as a result of ischemia or anoxia.

EXAMPLE 8

Construction of Vaccinia Virus-recombinant Expression Constructs for Functional Expression of Amino Acid Transporters Using an alternative approach, the amino acid transporter proteins of the invention are expressed in human HeLa (vulval adenocarcinoma) cells via a vaccinia virus-based construct. In these experiments, each of the amino acid transporter cDNAs of the invention are excised from their respective pOTV-containing constructs and subcloned into a modified pBluescript (Strategene) vector wherein each of the amino acid transporter cDNAs described above is under the control of a bacteriophage T7 RNA polymerase promoter (as is described in Blakely et al., 1991, Anal. Biochem. 194: 302–308), termed pT7-AAT constructs. HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with each of the amino acid transporter constructs described above (i.e. the pT7-AAT constructs) using a lipofectin-mediated (Bethesda Research Labs, Gaithersburg, Md.) transfection protocol (see Felgner et al., 1987, Proc. Nad. Acad. Sci. USA 84: 7413–7417). Cells are then incubated for 12–24 h before being assayed for amino acid transporter expression as described in Example 5.

EXAMPLE 9

Construction of Fusion Proteins-recombinant Expression Constructs for Expresion of Immunologically-active Epitopes of Amino Acid Transporters The amino acid transporter proteins of the invention are expressed as fusion proteins in bacteria to produce immunologically-active epitopes. In these experiments, each of the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNAs are translationally in-frame with sequences encoding glutathione-S-transferase (described in Arriza et al., 1992, J. Neurosci. 12: 4045–4055), termed pGST-AAT constructs. After introduction of the pGST-AAT constructs into bacterial cells (E. coli, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against each of the amino acid transporters of the invention by inoculation of rabbits with 300–500 µg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual*, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

| Amino Acid (1 mM)* | ASCT1 RNA-injected Oocytes** | Water-injected Oocytes** |
|---|---|---|
| Alanine | 18 ± 2 | 0.6 ± 0.1 |
| Serine | 20 ± 5.1 | 0.4 ± 0.1 |
| Cysteine | 19.2 ± 5.9 | 1.0 ± 0.3 |

*n = 5;
**pmol/min per oocyte:

TABLE II

| Amino Acid* | $K_m$ (µM) | $I_{max}$** |
|---|---|---|
| Alanine | 71 ± 14 | (1.0) |
| Serine | 88 ± 11 | 1.2 ± 0.08 |
| Cysteine | 29 ± 6 | 1.0 ± 0.04 |
| Threonine | 137 ± 19 | 1.4 ± 0.03 |
| Valine | 390 ± 8 | 0.6 ± 0.11 |

NOTE: data is expressed as the mean of at least 5 determinations ± standard error.
*All amino acids were the L-stereoisomer
**$I_{max}$ was determined by least squares fit to the equation:
$I = I_{max} \times ([S]/(K_m + [S]))$
where $I_{max}$ is the maximal current and $K_m$ is the transport constant

TABLE III

Glutamate uptake inhibition constants.

| Compound | Ki (in $\mu$M) determined for each transporter[a] | | |
|---|---|---|---|
| | EAAT1 | EAAT2 | EAAT3 |
| THA (L-threo-β-hydroxyaspartate) | 32 ± 8 | 19 ± 6 | 25 ± 5 |
| PDC (L-trans-pyrrolidine-2,4-dicarboxylate) | 79 ± 7 | 8 ± 2 | 61 ± 14 |
| SOS (L-Serine-O-sulfate) | 107 ± 8 | 1157 ± 275 | 150 ± 52 |
| DHK (Dihydrokainate) | >1 mM | 23 ± 6 | >1 mM |
| KAI (Kainate) | >1 mM | 59 ± 18 | >1 mM |
| L-cysteate | 10 ± 3 | 10 ± 2 | 19 ± 9 |
| L-cysteine sulfinic acid | 14 ± 7 | 6 ± 1 | 17 ± 2 |
| β-glutamate | 297 ± 118 | 156 ± 37 | 307 ± 48 |
| L-aspartate-β-hydroxymate | 369 ± 70 | 184 ± 27 | 133 ± 34 |

[a]Under the assay conditions used ([S] << Km), the Ki value does not differ significantly from the measured IC50.

What is claimed is:

1. A method of screening a compound for binding to an excitatory amino acid transporter in cells expressing the excitatory amino acid transporter, the method comprising the following steps:
   (a) transforming a host cell with a recombinant expression construct encoding a human excitatory amino acid transporter EAAT3, wherein the cells of the transformed cell culture express the transporter; and
   (b) assaying the transformed cell with the compound to determine whether the compound binds to the excitatory amino acid transporter.

2. The method of claim 1, wherein the human excitatory amino acid transporter is human EAAT3 having an amino acid sequence identified as SEQ ID No. 9.

3. A method of screening a compound for competitive binding to an excitatory amino acid transporter in cells expressing the excitatory amino acid transporter, the method comprising the following steps:
   (a) transforming a host cell with a recombinant expression construct encoding a human excitatory amino acid transporter EAAT3, wherein the cells of the transformed cell culture express the transporter; and
   (b) assaying the transformed cell with the compound in the presence and in the absence of an agonist for the excitatory amino acid transporter; and
   (c) determining whether the compound competes with the agonist for binding to the excitatory amino acid transporter.

4. The method of claim 3, wherein the human excitatory amino acid transporter is human EAAT3 having an amino acid sequence identified as SEQ ID No. 9.

5. The method of claim 3, wherein the compound is detectably-labeled.

6. The method of claim 3, wherein the excitatory amino acid transporter agonist is detectably-labeled.

7. The method of claim 3, wherein the excitatory amino acid transport competitor is quantitatively characterized by assaying the transformed cell culture with varying amounts of the competitor in the presence of a detectably-labeled excitatory amino acid or analogue thereof and measuring the extent of competition with excitatory amino acid transport thereby.

8. A method of screening a compound to determine if the compound is an inhibitor of an excitatory amino acid transporter in cells expressing the excitatory amino acid transporter, the method comprising the following steps:
   (a) transforming a host cell with a recombinant expression construct encoding a human excitatory amino acid transporter EAAT3, wherein the cells of the transformed cell culture express the transporter; and
   (b) assaying the transformed cell culture with the compound to determine whether the compound is capable of inhibiting excitatory amino acid transport by the excitatory amino acid transporter.

9. The method of claim 8, wherein the human excitatory amino acid transporter is human EAAT3 having an amino acid sequence identified as SEQ ID No. 9.

10. The method of claim 8, wherein the excitatory amino acid transport inhibitor is quantitatively characterized by assaying the transformed cell culture with varying amounts of the inhibitor in the presence of a detectably-labeled excitatory amino acid or analogue thereof and measuring the extent of inhibition of excitatory amino acid transport thereby.

11. The method of claim 10, wherein the human excitatory amino acid transporter is human EAAT3 having an amino acid sequence identified as SEQ ID No. 9.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 63 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CTGRGCRATG AARATGGCAG CCAGGGCYTC ATACAGGGCT GTGCCRTCCA TGTTRATGGT     60

RGC                                                                  63
```

(2) INFORMATION FOR SEQ ID NO:2:

(i) SEQUENCE CHARACTERISTICS:
      (A) LENGTH: 1680 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: 5'UTR
      (B) LOCATION: 1..30

(ix) FEATURE:
      (A) NAME/KEY: CDS
      (B) LOCATION: 31..1626

(ix) FEATURE:
      (A) NAME/KEY: 3'UTR
      (B) LOCATION: 1626..1680

(xi) SEQUENCE DESCRIPTION: SEQ ID NO:2:

```
CACCTCTAGC TCGGAGCGGC GTGTAGCGCC ATG GAG AAG AGC AAC GAG ACC AAC     54
                                Met Glu Lys Ser Asn Glu Thr Asn
```

-continued

```
                          1                   5
GGC TAC CTT GAC AGC GCT CAG GCG GGG CCT GCG GCC GGG CCC GGA GCT      102
Gly Tyr Leu Asp Ser Ala Gln Ala Gly Pro Ala Ala Gly Pro Gly Ala
         10                  15                  20

CCG GGG ACC GCG GCG GGA CGC GCA CGG CGT TGC GCG CGC TTC CTG CGG      150
Pro Gly Thr Ala Ala Gly Arg Ala Arg Arg Cys Ala Arg Phe Leu Arg
 25                  30                  35                  40

CGC CAA GCG CTG GTG CTG CTC ACC GTG TCC GGG GTG CTG GCG GGC GCG      198
Arg Gln Ala Leu Val Leu Leu Thr Val Ser Gly Val Leu Ala Gly Ala
                 45                  50                  55

GGC CTG GGC GCG GCG TTG CGC GGG CTC AGC CTG AGC CGC ACG CAG GTC      246
Gly Leu Gly Ala Ala Leu Arg Gly Leu Ser Leu Ser Arg Thr Gln Val
             60                  65                  70

ACC TAC CTG GCC TTC CCC GGC GAG ATG CTG CTC CGC ATG CTG CGC ATG      294
Thr Tyr Leu Ala Phe Pro Gly Glu Met Leu Leu Arg Met Leu Arg Met
         75                  80                  85

ATC ATC CTG CCG CTG GTG GTC TGC AGC CTG GTG TCG GGC GCC GCC TCG      342
Ile Ile Leu Pro Leu Val Val Cys Ser Leu Val Ser Gly Ala Ala Ser
 90                  95                 100

CTC GAT GCC AGC TGC CTC GGG CGT CTG GGC GGC ATC CGT GTC GCC TAC      390
Leu Asp Ala Ser Cys Leu Gly Arg Leu Gly Gly Ile Arg Val Ala Tyr
105                 110                 115                 120

TTT GGC CTC ACC ACA CTG AGT GCC TCG GCG CTC GCC GTG GCC TTG GCG      438
Phe Gly Leu Thr Thr Leu Ser Ala Ser Ala Leu Ala Val Ala Leu Ala
                125                 130                 135

TTC ATC ATC AAG CCA GGA TCC GGT GCG CAG ACC CTT CAG TCC AGC GAC      486
Phe Ile Ile Lys Pro Gly Ser Gly Ala Gln Thr Leu Gln Ser Ser Asp
            140                 145                 150

CTG GGG CTG GAG GAC TCG GGG CCT CCT CCT GTC CCC AAA GAG ACG GTG      534
Leu Gly Leu Glu Asp Ser Gly Pro Pro Pro Val Pro Lys Glu Thr Val
        155                 160                 165

GAC TCT TTC CTC GAC CTG GCC AGA AAC CTG TTT CCC TCC AAT CTT GTG      582
Asp Ser Phe Leu Asp Leu Ala Arg Asn Leu Phe Pro Ser Asn Leu Val
170                 175                 180

GTT GCA GCT TTC CGT ACG TAT GCA ACC GAT TAT AAA GTC GTG ACC CAG      630
Val Ala Ala Phe Arg Thr Tyr Ala Thr Asp Tyr Lys Val Val Thr Gln
185                 190                 195                 200

AAC AGC AGC TCT GGA AAT GTA ACC CAT GAA AAG ATC CCC ATA GGC ACT      678
Asn Ser Ser Ser Gly Asn Val Thr His Glu Lys Ile Pro Ile Gly Thr
                205                 210                 215

GAG ATA GAA GGG ATG AAC ATT TTA GGA TTG GTC CTG TTT GCT CTG GTG      726
Glu Ile Glu Gly Met Asn Ile Leu Gly Leu Val Leu Phe Ala Leu Val
            220                 225                 230

TTA GGA GTG GCC TTA AAG AAA CTA GGC TCC GAA GGA GAA GAC CTC ATC      774
Leu Gly Val Ala Leu Lys Lys Leu Gly Ser Glu Gly Glu Asp Leu Ile
        235                 240                 245

CGT TTC TTC AAT TCC CTC AAC GAG GCG ACG ATG GTG CTG GTG TCC TGG      822
Arg Phe Phe Asn Ser Leu Asn Glu Ala Thr Met Val Leu Val Ser Trp
250                 255                 260

ATT ATG TGG TAC GTA CCT GTG GGC ATC ATG TTC CTT GTT GGA AGC AAG      870
Ile Met Trp Tyr Val Pro Val Gly Ile Met Phe Leu Val Gly Ser Lys
265                 270                 275                 280

ATC GTG GAA ATG AAA GAC ATC ATC GTG CTG GTG ACC AGC CTG GGG AAA      918
Ile Val Glu Met Lys Asp Ile Ile Val Leu Val Thr Ser Leu Gly Lys
                285                 290                 295

TAC ATC TTC GCA TCT ATA TTG GGC CAT GTT ATT CAT GGA GGA ATT GTT      966
Tyr Ile Phe Ala Ser Ile Leu Gly His Val Ile His Gly Gly Ile Val
            300                 305                 310

CTG CCA CTT ATT TAT TTT GTT TTC ACA CGA AAA AAC CCA TTC AGA TTC     1014
```

```
Leu Pro Leu Ile Tyr Phe Val Phe Thr Arg Lys Asn Pro Phe Arg Phe
            315                 320                 325

CTC CTG GGC CTC CTC GCC CCA TTT GCG ACA GCA TTT GCT ACC TGC TCC      1062
Leu Leu Gly Leu Leu Ala Pro Phe Ala Thr Ala Phe Ala Thr Cys Ser
        330                 335                 340

AGC TCA GCG ACC CTT CCC TCT ATG ATG AAG TGC ATT GAA GAG AAC AAT      1110
Ser Ser Ala Thr Leu Pro Ser Met Met Lys Cys Ile Glu Glu Asn Asn
345                 350                 355                 360

GGT GTG GAC AAG AGG ATC AGC AGG TTT ATT CTC CCC ATC GGG GCC ACC      1158
Gly Val Asp Lys Arg Ile Ser Arg Phe Ile Leu Pro Ile Gly Ala Thr
                365                 370                 375

GTG AAC ATG GAC GGA GCA GCC ATC TTC CAG TGT GTG GCC GCG GTG TTC      1206
Val Asn Met Asp Gly Ala Ala Ile Phe Gln Cys Val Ala Ala Val Phe
            380                 385                 390

ATT GCG CAA CTC AAC AAC ATA GAG CTC AAC GCA GGA CAG ATT TTC ACC      1254
Ile Ala Gln Leu Asn Asn Ile Glu Leu Asn Ala Gly Gln Ile Phe Thr
        395                 400                 405

ATT CTA GTG ACT GCC ACA GCG TCC AGT GTT GGA GCA GCA GGC GTG CCA      1302
Ile Leu Val Thr Ala Thr Ala Ser Ser Val Gly Ala Ala Gly Val Pro
410                 415                 420

GCT GGA GGG GTC CTC ACC ATT GCC ATT ATC CTG GAG GCC ATT GGG CTG      1350
Ala Gly Gly Val Leu Thr Ile Ala Ile Ile Leu Glu Ala Ile Gly Leu
425                 430                 435                 440

CCT ACT CAT GAC CTG CCT CTG ATC CTG GCT GTG GAC TGG ATT GTG GAC      1398
Pro Thr His Asp Leu Pro Leu Ile Leu Ala Val Asp Trp Ile Val Asp
                445                 450                 455

CGG ACC ACC ACG GTG GTG AAT GTG GAG GGG GAT GCC CTG GGT GCA GGC      1446
Arg Thr Thr Thr Val Val Asn Val Glu Gly Asp Ala Leu Gly Ala Gly
            460                 465                 470

ATT CTC CAC CAC CTG AAT CAG AAG GCA ACA AAG AAA GGC GAG CAG GAA      1494
Ile Leu His His Leu Asn Gln Lys Ala Thr Lys Lys Gly Glu Gln Glu
        475                 480                 485

CTT GCT GAG GTG AAA GTG GAA GCC ATC CCC AAC TGC AAG TCT GAG GAG      1542
Leu Ala Glu Val Lys Val Glu Ala Ile Pro Asn Cys Lys Ser Glu Glu
        490                 495                 500

GAG ACA TCG CCC CTG GTG ACA CAC CAG AAC CCC GCT GGC CCC GTG GCC      1590
Glu Thr Ser Pro Leu Val Thr His Gln Asn Pro Ala Gly Pro Val Ala
505                 510                 515                 520

AGT GCC CCA GAA CTG GAA TCC AAG GAG TCG GTT CTG TGATGGGGCT           1636
Ser Ala Pro Glu Leu Glu Ser Lys Glu Ser Val Leu
                525                 530

GGGCTTTGGG CTTGCCTGCC AGCAGTGATG TCCCACCCTG TTCA                     1680

(2) INFORMATION FOR SEQ ID NO:3:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Lys Ser Asn Glu Thr Asn Gly Tyr Leu Asp Ser Ala Gln Ala
 1               5                  10                  15

Gly Pro Ala Ala Gly Pro Gly Ala Pro Gly Thr Ala Ala Gly Arg Ala
            20                  25                  30

Arg Arg Cys Ala Arg Phe Leu Arg Arg Gln Ala Leu Val Leu Leu Thr
        35                  40                  45

Val Ser Gly Val Leu Ala Gly Ala Gly Leu Gly Ala Ala Leu Arg Gly
```

```
                50                  55                  60
Leu Ser Leu Ser Arg Thr Gln Val Thr Tyr Leu Ala Phe Pro Gly Glu
 65                  70                  75                  80

Met Leu Leu Arg Met Leu Arg Met Ile Ile Leu Pro Leu Val Val Cys
                 85                  90                  95

Ser Leu Val Ser Gly Ala Ala Ser Leu Asp Ala Ser Cys Leu Gly Arg
                100                 105                 110

Leu Gly Gly Ile Arg Val Ala Tyr Phe Gly Leu Thr Thr Leu Ser Ala
                115                 120                 125

Ser Ala Leu Ala Val Ala Leu Ala Phe Ile Ile Lys Pro Gly Ser Gly
130                 135                 140

Ala Gln Thr Leu Gln Ser Ser Asp Leu Gly Leu Glu Asp Ser Gly Pro
145                 150                 155                 160

Pro Pro Val Pro Lys Glu Thr Val Asp Ser Phe Leu Asp Leu Ala Arg
                165                 170                 175

Asn Leu Phe Pro Ser Asn Leu Val Val Ala Ala Phe Arg Thr Tyr Ala
                180                 185                 190

Thr Asp Tyr Lys Val Val Thr Gln Asn Ser Ser Gly Asn Val Thr
                195                 200                 205

His Glu Lys Ile Pro Ile Gly Thr Glu Ile Glu Gly Met Asn Ile Leu
                210                 215                 220

Gly Leu Val Leu Phe Ala Leu Val Leu Gly Val Ala Leu Lys Lys Leu
225                 230                 235                 240

Gly Ser Glu Gly Glu Asp Leu Ile Arg Phe Phe Asn Ser Leu Asn Glu
                245                 250                 255

Ala Thr Met Val Leu Val Ser Trp Ile Met Trp Tyr Val Pro Val Gly
                260                 265                 270

Ile Met Phe Leu Val Gly Ser Lys Ile Val Glu Met Lys Asp Ile Ile
                275                 280                 285

Val Leu Val Thr Ser Leu Gly Lys Tyr Ile Phe Ala Ser Ile Leu Gly
                290                 295                 300

His Val Ile His Gly Gly Ile Val Leu Pro Leu Ile Tyr Phe Val Phe
305                 310                 315                 320

Thr Arg Lys Asn Pro Phe Arg Phe Leu Leu Gly Leu Leu Ala Pro Phe
                325                 330                 335

Ala Thr Ala Phe Ala Thr Cys Ser Ser Ser Ala Thr Leu Pro Ser Met
                340                 345                 350

Met Lys Cys Ile Glu Glu Asn Asn Gly Val Asp Lys Arg Ile Ser Arg
                355                 360                 365

Phe Ile Leu Pro Ile Gly Ala Thr Val Asn Met Asp Gly Ala Ala Ile
                370                 375                 380

Phe Gln Cys Val Ala Ala Val Phe Ile Ala Gln Leu Asn Asn Ile Glu
385                 390                 395                 400

Leu Asn Ala Gly Gln Ile Phe Thr Ile Leu Val Thr Ala Thr Ala Ser
                405                 410                 415

Ser Val Gly Ala Ala Gly Val Pro Ala Gly Gly Val Leu Thr Ile Ala
                420                 425                 430

Ile Ile Leu Glu Ala Ile Gly Leu Pro Thr His Asp Leu Pro Leu Ile
                435                 440                 445

Leu Ala Val Asp Trp Ile Val Asp Arg Thr Thr Thr Val Val Asn Val
                450                 455                 460

Glu Gly Asp Ala Leu Gly Ala Gly Ile Leu His His Leu Asn Gln Lys
465                 470                 475                 480
```

```
Ala Thr Lys Lys Gly Glu Gln Glu Leu Ala Glu Val Lys Val Glu Ala
            485                 490                 495

Ile Pro Asn Cys Lys Ser Glu Glu Thr Ser Pro Leu Val Thr His
        500                 505                 510

Gln Asn Pro Ala Gly Pro Val Ala Ser Ala Pro Glu Leu Glu Ser Lys
        515                 520                 525

Glu Ser Val Leu
    530
```

(2) INFORMATION FOR SEQ ID NO:4:

(i) SEQUENCE CHARACTERISTICS:
        (A) LENGTH: 1680 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..30

(ix) FEATURE:
        (A) NAME/KEY: CDS
        (B) LOCATION: 31..1656

(ix) FEATURE:
        (A) NAME/KEY: 3'UTR
        (B) LOCATION: 1657..1680

(xi) SEQUENCE DESCRIPTION: SEQ ID NO:4:

```
AAAGAAGAGA CCCTCCTAGA AAAGTAAAAT ATG ACT AAA AGC AAT GGA GAA GAG          54
                                Met Thr Lys Ser Asn Gly Glu Glu
                                 1               5

CCC AAG ATG GGG GGC AGG ATG GAG AGA TTC CAG CAG GGA GTC CGT AAA         102
Pro Lys Met Gly Gly Arg Met Glu Arg Phe Gln Gln Gly Val Arg Lys
 10              15                  20

CGC ACA CTT TTG GCC AAG AAG AAA GTG CAG AAC ATT ACA AAG GAG GTT         150
Arg Thr Leu Leu Ala Lys Lys Lys Val Gln Asn Ile Thr Lys Glu Val
 25              30                  35                  40

GTT AAA AGT TAC CTG TTT CGG AAT GCT TTT GTG CTG CTC ACA GTC ACC         198
Val Lys Ser Tyr Leu Phe Arg Asn Ala Phe Val Leu Leu Thr Val Thr
                 45                  50                  55

GCT GTC ATT GTG GGT ACA ATC CTT GGA TTT ACC CTC CGA CCA TAC AGA         246
Ala Val Ile Val Gly Thr Ile Leu Gly Phe Thr Leu Arg Pro Tyr Arg
         60                  65                  70

ATG AGC TAC CGG GAA GTC AAG TAC TTC TCC TTT CCT GGG GAA CTT CTG         294
Met Ser Tyr Arg Glu Val Lys Tyr Phe Ser Phe Pro Gly Glu Leu Leu
     75                  80                  85

ATG AGG ATG TTA CAG ATG CTG GTC TTA CCA CTT ATC ATC TCC AGT CTT         342
Met Arg Met Leu Gln Met Leu Val Leu Pro Leu Ile Ile Ser Ser Leu
 90                  95                 100

GTC ACA GGA ATG GCG GCG CTA GAT AGT AAG GCA TCA GGG AAG TGG GAA         390
Val Thr Gly Met Ala Ala Leu Asp Ser Lys Ala Ser Gly Lys Trp Glu
105                 110                 115                 120

TGC GGA GCT GTA GTC TAT TAT ATG ACT ACC ACC ATC ATT GCT GTG GTG         438
Cys Gly Ala Val Val Tyr Tyr Met Thr Thr Thr Ile Ile Ala Val Val
                125                 130                 135

ATT GGC ATA ATC ATT GTC ATC ATC ATC CAT CCT GGG AAG GGC ACA AAG         486
Ile Gly Ile Ile Ile Val Ile Ile Ile His Pro Gly Lys Gly Thr Lys
        140                 145                 150

GAA AAC ATG CAC AGA GAA GGC AAA ATT GTA CGA GTG ACA GCT GCA GAT         534
```

```
                                  -continued

Glu Asn Met His Arg Glu Gly Lys Ile Val Arg Val Thr Ala Ala Asp
            155                 160                 165

GCC TTC CTG GAC TTG ATC AGG AAC ATG TTA AAT CCA AAT CTG GTA GAA        582
Ala Phe Leu Asp Leu Ile Arg Asn Met Leu Asn Pro Asn Leu Val Glu
170                 175                 180

GCC TGC TTT AAA CAG TTT AAA ACC AAC TAT GAG AAG AGA AGC TTT AAA        630
Ala Cys Phe Lys Gln Phe Lys Thr Asn Tyr Glu Lys Arg Ser Phe Lys
185                 190                 195                 200

GTG CCC ATC CAG GCC AAC GAA ACG CTT GTG GGT GCT GTG ATA AAC AAT        678
Val Pro Ile Gln Ala Asn Glu Thr Leu Val Gly Ala Val Ile Asn Asn
                205                 210                 215

GTG TCT GAG GCC ATG GAG ACT CTT ACC CGA ATC ACA GAG GAG CTG GTC        726
Val Ser Glu Ala Met Glu Thr Leu Thr Arg Ile Thr Glu Glu Leu Val
            220                 225                 230

CCA GTT CCA GGA TCT GTG AAT GGA GTC AAT GCC CTG GGT CTA GTT GTC        774
Pro Val Pro Gly Ser Val Asn Gly Val Asn Ala Leu Gly Leu Val Val
                235                 240                 245

TTC TCC ATG TGC TTC GGT TTT GTG ATT GGA AAC ATG AAG GAA CAG GGG        822
Phe Ser Met Cys Phe Gly Phe Val Ile Gly Asn Met Lys Glu Gln Gly
            250                 255                 260

CAG GCC CTG AGA GAG TTC TTT GAT TCT CTT AAC GAA GCC ATC ATG AGA        870
Gln Ala Leu Arg Glu Phe Phe Asp Ser Leu Asn Glu Ala Ile Met Arg
265                 270                 275                 280

CTG GTA GCA GTA ATA ATG TGG TAT GCC CCC GTG GGT ATT CTC TTC CTG        918
Leu Val Ala Val Ile Met Trp Tyr Ala Pro Val Gly Ile Leu Phe Leu
                285                 290                 295

ATT GCT GGG AAG ATT GTG GAG ATG GAA GAC ATG GGT GTG ATT GGG GGG        966
Ile Ala Gly Lys Ile Val Glu Met Glu Asp Met Gly Val Ile Gly Gly
            300                 305                 310

CAG CTT GCC ATG TAC ACC GTG ACT GTC ATT GTT GGC TTA CTC ATT CAC       1014
Gln Leu Ala Met Tyr Thr Val Thr Val Ile Val Gly Leu Leu Ile His
            315                 320                 325

GCA GTC ATC GTC TTG CCA CTC CTC TAC TTC TTG GTA ACA CGG AAA AAC       1062
Ala Val Ile Val Leu Pro Leu Leu Tyr Phe Leu Val Thr Arg Lys Asn
330                 335                 340

CCT TGG GTT TTT ATT GGA GGG TTG CTG CAA GCA CTC ATC ACC GCT CTG       1110
Pro Trp Val Phe Ile Gly Gly Leu Leu Gln Ala Leu Ile Thr Ala Leu
345                 350                 355                 360

GGG ACC TCT TCA AGT TCT GCC ACC CTA CCC ATC ACC TTC AAG TGC CTG       1158
Gly Thr Ser Ser Ser Ser Ala Thr Leu Pro Ile Thr Phe Lys Cys Leu
                365                 370                 375

GAA GAG AAC AAT GGC GTG GAC AAG CGC GTC ACC AGA TTC GTG CTC CCC       1206
Glu Glu Asn Asn Gly Val Asp Lys Arg Val Thr Arg Phe Val Leu Pro
            380                 385                 390

GTA GGA GCC ACC ATT AAC ATG GAT GGG ACT GCC CTC TAT GAG GCT TTG       1254
Val Gly Ala Thr Ile Asn Met Asp Gly Thr Ala Leu Tyr Glu Ala Leu
            395                 400                 405

GCT GCC ATT TTC ATT GCT CAA GTT AAC AAC TTT GAA CTG AAC TTC GGA       1302
Ala Ala Ile Phe Ile Ala Gln Val Asn Asn Phe Glu Leu Asn Phe Gly
410                 415                 420

CAA ATT ATT ACA ATC AGC ATC ACA GCC ACA GCT GCC AGT ATT GGG GCA       1350
Gln Ile Ile Thr Ile Ser Ile Thr Ala Thr Ala Ala Ser Ile Gly Ala
425                 430                 435                 440

GCT GGA ATT CCT CAG GCG GGC CTG GTC ACT ATG GTC ATT GTG CTG ACA       1398
Ala Gly Ile Pro Gln Ala Gly Leu Val Thr Met Val Ile Val Leu Thr
                445                 450                 455

TCT GTC GGC CTG CCC ACT GAC GAC ATC ACG CTC ATC ATC GCG GTG GAC       1446
Ser Val Gly Leu Pro Thr Asp Asp Ile Thr Leu Ile Ile Ala Val Asp
            460                 465                 470
```

```
TGG TTC TTG GAT CGC CTC CGG ACC ACC ACC AAC GTA CTG GGA GAC TCC      1494
Trp Phe Leu Asp Arg Leu Arg Thr Thr Thr Asn Val Leu Gly Asp Ser
        475                 480                 485

CTG GGA GCT GGG ATT GTG GAG CAC TTG TCA CGA CAT GAA CTG AAG AAC      1542
Leu Gly Ala Gly Ile Val Glu His Leu Ser Arg His Glu Leu Lys Asn
        490                 495                 500

AGA GAT GTT GAA ATG GGT AAC TCA GTG ATT GAA GAG AAT GAA ATG AAG      1590
Arg Asp Val Glu Met Gly Asn Ser Val Ile Glu Glu Asn Glu Met Lys
505                 510                 515                 520

AAA CCA TAT CAA CTG ATT GCA CAG GAC AAT GAA ACT GAG AAA CCC ATC      1638
Lys Pro Tyr Gln Leu Ile Ala Gln Asp Asn Glu Thr Glu Lys Pro Ile
            525                 530                 535

GAC AGT GAA ACC AAG ATG TAGACTAACA TAAAGAAACA CTTT                   1680
Asp Ser Glu Thr Lys Met
                540
```

(2) INFORMATION FOR SEQ ID NO:5:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:5:

```
Met Thr Lys Ser Asn Gly Glu Glu Pro Lys Met Gly Gly Arg Met Glu
 1               5                  10                  15

Arg Phe Gln Gln Gly Val Arg Lys Arg Thr Leu Leu Ala Lys Lys Lys
                20                  25                  30

Val Gln Asn Ile Thr Lys Glu Val Val Lys Ser Tyr Leu Phe Arg Asn
            35                  40                  45

Ala Phe Val Leu Leu Thr Val Thr Ala Val Ile Val Gly Thr Ile Leu
        50                  55                  60

Gly Phe Thr Leu Arg Pro Tyr Arg Met Ser Tyr Arg Glu Val Lys Tyr
65                  70                  75                  80

Phe Ser Phe Pro Gly Glu Leu Leu Met Arg Met Leu Gln Met Leu Val
                85                  90                  95

Leu Pro Leu Ile Ile Ser Ser Leu Val Thr Gly Met Ala Ala Leu Asp
                100                 105                 110

Ser Lys Ala Ser Gly Lys Trp Glu Cys Gly Ala Val Val Tyr Tyr Met
            115                 120                 125

Thr Thr Thr Ile Ile Ala Val Val Ile Gly Ile Ile Ile Val Ile Ile
130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
                165                 170                 175

Met Leu Asn Pro Asn Leu Val Glu Ala Cys Phe Lys Gln Phe Lys Thr
                180                 185                 190

Asn Tyr Glu Lys Arg Ser Phe Lys Val Pro Ile Gln Ala Asn Glu Thr
            195                 200                 205

Leu Val Gly Ala Val Ile Asn Asn Val Ser Glu Ala Met Glu Thr Leu
        210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255
```

```
Ile Gly Asn Met Lys Glu Gln Gly Gln Ala Leu Arg Glu Phe Phe Asp
            260                 265                 270

Ser Leu Asn Glu Ala Ile Met Arg Leu Val Ala Val Ile Met Trp Tyr
        275                 280                 285

Ala Pro Val Gly Ile Leu Phe Leu Ile Ala Gly Lys Ile Val Glu Met
        290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Leu Pro Leu Leu
                325                 330                 335

Tyr Phe Leu Val Thr Arg Lys Asn Pro Trp Val Phe Ile Gly Gly Leu
            340                 345                 350

Leu Gln Ala Leu Ile Thr Ala Leu Gly Thr Ser Ser Ser Ala Thr
        355                 360                 365

Leu Pro Ile Thr Phe Lys Cys Leu Glu Glu Asn Asn Gly Val Asp Lys
        370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
            405                 410                 415

Asn Asn Phe Glu Leu Asn Phe Gly Gln Ile Ile Thr Ile Ser Ile Thr
                420                 425                 430

Ala Thr Ala Ala Ser Ile Gly Ala Ala Gly Ile Pro Gln Ala Gly Leu
            435                 440                 445

Val Thr Met Val Ile Val Leu Thr Ser Val Gly Leu Pro Thr Asp Asp
450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
        515                 520                 525

Asp Asn Glu Thr Glu Lys Pro Ile Asp Ser Glu Thr Lys Met
530                 535                 540

(2) INFORMATION FOR SEQ ID NO:6:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..33

(ix) FEATURE:
        (A) NAME/KEY: CDS
        (B) LOCATION: 34..1755

(ix) FEATURE:
        (A) NAME/KEY: 3'UTR
        (B) LOCATION: 1756..1800

(xi) SEQUENCE DESCRIPTION: SEQ ID NO:6:
```

```
GATAGTGCTG AAGAGGAGGG GCGTTCCCAG ACC ATG GCA TCT ACG GAA GGT GCC          54
                                    Met Ala Ser Thr Glu Gly Ala
                                     1               5

AAC AAT ATG CCC AAG CAG GTG GAA GTG CGA ATG CCA GAC AGT CAT CTT          102
Asn Asn Met Pro Lys Gln Val Glu Val Arg Met Pro Asp Ser His Leu
         10                  15                  20

GGC TCA GAG GAA CCC AAG CAC CGG CAC CTG GGC CTG CGC CTG TGT GAC          150
Gly Ser Glu Glu Pro Lys His Arg His Leu Gly Leu Arg Leu Cys Asp
     25                  30                  35

AAG CTG GGG AAG AAT CTG CTC CTC ACC CTG ACG GTG TTT GGT GTC ATC          198
Lys Leu Gly Lys Asn Leu Leu Leu Thr Leu Thr Val Phe Gly Val Ile
 40                  45                  50                  55

CTG GGA GCA GTG TGT GGA GGG CTT CTT CGC TTG GCA TCT CCC ATC CAC          246
Leu Gly Ala Val Cys Gly Gly Leu Leu Arg Leu Ala Ser Pro Ile His
                 60                  65                  70

CCT GAT GTG GTT ATG TTA ATA GCC TTC CCA GGG GAT ATA CTC ATG AGG          294
Pro Asp Val Val Met Leu Ile Ala Phe Pro Gly Asp Ile Leu Met Arg
             75                  80                  85

ATG CTA AAA ATG CTC ATT CTG GGT CTA ATC ATC TCC AGC TTA ATC ACA          342
Met Leu Lys Met Leu Ile Leu Gly Leu Ile Ile Ser Ser Leu Ile Thr
         90                  95                 100

GGG TTG TCA GGC CTG GAT GCT AAG GCT AGT GGC CGC TTG GGC ACG AGA          390
Gly Leu Ser Gly Leu Asp Ala Lys Ala Ser Gly Arg Leu Gly Thr Arg
    105                 110                 115

GCC ATG GTG TAT TAC ATG TCC ACG ACC ATC ATT GCT GCA GTA CTG GGG          438
Ala Met Val Tyr Tyr Met Ser Thr Thr Ile Ile Ala Ala Val Leu Gly
120                 125                 130                 135

GTC ATT CTG GTC TTG GCT ATC CAT CCA GGC AAT CCC AAG CTC AAG AAG          486
Val Ile Leu Val Leu Ala Ile His Pro Gly Asn Pro Lys Leu Lys Lys
                140                 145                 150

CAG CTG GGG CCT GGG AAG AAG AAT GAT GAA GTG TCC AGC CTG GAT GCC          534
Gln Leu Gly Pro Gly Lys Lys Asn Asp Glu Val Ser Ser Leu Asp Ala
            155                 160                 165

TTC CTG GAC CTT ATT CGA AAT CTC TTC CCT GAA AAC CTT GTC CAA GCC          582
Phe Leu Asp Leu Ile Arg Asn Leu Phe Pro Glu Asn Leu Val Gln Ala
        170                 175                 180

TGC TTT CAA CAG ATT CAA ACA GTG ACG AAG AAA GTC CTG GTT GCA CCA          630
Cys Phe Gln Gln Ile Gln Thr Val Thr Lys Lys Val Leu Val Ala Pro
    185                 190                 195

CCG CCA GAC GAG GAG GCC AAC GCA ACC AGC GCT GAA GTC TCT CTG TTG          678
Pro Pro Asp Glu Glu Ala Asn Ala Thr Ser Ala Glu Val Ser Leu Leu
200                 205                 210                 215

AAC GAG ACT GTG ACT GAG GTG CCG GAG GAG ACT AAG ATG GTT ATC AAG          726
Asn Glu Thr Val Thr Glu Val Pro Glu Glu Thr Lys Met Val Ile Lys
                220                 225                 230

AAG GGC CTG GAG TTC AAG GAT GGG ATG AAC GTC TTA GGT CTG ATA GGG          774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC          822
Phe Phe Ile Ala Phe Gly Ile Ala Met Gly Lys Met Gly Asp Gln Ala
        250                 255                 260

AAG CTG ATG GTG GAT TTC TTC AAC ATT TTG AAT GAG ATT GTA ATG AAG          870
Lys Leu Met Val Asp Phe Phe Asn Ile Leu Asn Glu Ile Val Met Lys
    265                 270                 275

TTA GTG ATC ATG ATC ATG TGG TAC TCT CCC CTG GGT ATC GCC TGC CTG          918
Leu Val Ile Met Ile Met Trp Tyr Ser Pro Leu Gly Ile Ala Cys Leu
280                 285                 290                 295

ATC TGT GGA AAG ATC ATT GCA ATC AAG GAC TTA GAA GTG GTT GCT AGG          966
Ile Cys Gly Lys Ile Ile Ala Ile Lys Asp Leu Glu Val Val Ala Arg
```

```
                    300                 305                 310
CAA CTG GGG ATG TAC ATG GTA ACA GTG ATC ATA GGC CTC ATC ATC CAC        1014
Gln Leu Gly Met Tyr Met Val Thr Val Ile Ile Gly Leu Ile Ile His
                315                 320                 325

GGG GGC ATC TTT CTC CCC TTG ATT TAC TTT GTA GTG ACC AGG AAA AAC        1062
Gly Gly Ile Phe Leu Pro Leu Ile Tyr Phe Val Val Thr Arg Lys Asn
                330                 335                 340

CCC TTC TCC CTT TTT GCT GGC ATT TTC CAA GCT TGG ATC ACT GCC CTG        1110
Pro Phe Ser Leu Phe Ala Gly Ile Phe Gln Ala Trp Ile Thr Ala Leu
            345                 350                 355

GGC ACC GCT TCC AGT GCT GGA ACT TTG CCT GTC ACC TTT CGT TGC CTG        1158
Gly Thr Ala Ser Ser Ala Gly Thr Leu Pro Val Thr Phe Arg Cys Leu
360                 365                 370                 375

GAA GAA AAT CTG GGG ATT GAT AAG CGT GTG ACT AGA TTC GTC CTT CCT        1206
Glu Glu Asn Leu Gly Ile Asp Lys Arg Val Thr Arg Phe Val Leu Pro
                380                 385                 390

GTT GGA GCA ACC ATT AAC ATG GAT GGT ACA GCC CTT TAT GAA GCG GTG        1254
Val Gly Ala Thr Ile Asn Met Asp Gly Thr Ala Leu Tyr Glu Ala Val
                395                 400                 405

GCC GCC ATC TTT ATA GCC CAA ATG AAT GGT GTT GTC CTG GAT GGA GGA        1302
Ala Ala Ile Phe Ile Ala Gln Met Asn Gly Val Val Leu Asp Gly Gly
            410                 415                 420

CAG ATT GTG ACT GTA AGC CTC ACA GCC ACC CTG GCA AGC GTC GGC GCG        1350
Gln Ile Val Thr Val Ser Leu Thr Ala Thr Leu Ala Ser Val Gly Ala
425                 430                 435

GCC AGT ATC CCC AGT GCC GGG CTG GTC ACC ATG CTC CTC ATT CTG ACA        1398
Ala Ser Ile Pro Ser Ala Gly Leu Val Thr Met Leu Leu Ile Leu Thr
440                 445                 450                 455

GCC GTG GGC CTG CCA ACA GAG GAC ATC AGC TTG CTG GTG GCT GTG GAC        1446
Ala Val Gly Leu Pro Thr Glu Asp Ile Ser Leu Leu Val Ala Val Asp
                460                 465                 470

TGG CTG CTG GAC AGG ATG AGA ACT TCA GTC AAT GTT GTG GGT GAC TCT        1494
Trp Leu Leu Asp Arg Met Arg Thr Ser Val Asn Val Val Gly Asp Ser
            475                 480                 485

TTT GGG GCT GGG ATA GTC TAT CAC CTC TCC AAG TCT GAG CTG GAT ACC        1542
Phe Gly Ala Gly Ile Val Tyr His Leu Ser Lys Ser Glu Leu Asp Thr
            490                 495                 500

ATT GAC TCC CAG CAT CGA GTG CAT GAA GAT ATT GAA ATG ACC AAG ACT        1590
Ile Asp Ser Gln His Arg Val His Glu Asp Ile Glu Met Thr Lys Thr
        505                 510                 515

CAA TCC ATT TAT GAT GAC ATG AAG AAC CAC AGG GAA AGC AAC TCT AAT        1638
Gln Ser Ile Tyr Asp Asp Met Lys Asn His Arg Glu Ser Asn Ser Asn
520                 525                 530                 535

CAA TGT GTC TAT GCT GCA CAC AAC TCT GTC ATA GTA GAT GAA TGC AAG        1686
Gln Cys Val Tyr Ala Ala His Asn Ser Val Ile Val Asp Glu Cys Lys
                540                 545                 550

GTA ACT CTG GCA GCC AAT GGA AAG TCA GCC GAC TGC AGT GTT GAG GAA        1734
Val Thr Leu Ala Ala Asn Gly Lys Ser Ala Asp Cys Ser Val Glu Glu
            555                 560                 565

GAA CCT TGG AAA CGT GAG AAA TAAGGATATG AGTCTCAGCA AATTCTTGAA           1785
Glu Pro Trp Lys Arg Glu Lys
            570

TAAACTCCCC AGCGT                                                       1800

(2) INFORMATION FOR SEQ ID NO:7:

(i) SEQUENCE CHARACTERISTICS:
        (A) LENGTH: 574 amino acids
        (B) TYPE: amino acid
        (D) TOPOLOGY: linear
```

(ii) MOLECULE TYPE: protein (xi) SEQUENCE DESCRIPTION: SEQ ID NO:7:

```
Met Ala Ser Thr Glu Gly Ala Asn Asn Met Pro Lys Gln Val Glu Val
  1               5                  10                  15

Arg Met Pro Asp Ser His Leu Gly Ser Glu Glu Pro Lys His Arg His
             20                  25                  30

Leu Gly Leu Arg Leu Cys Asp Lys Leu Gly Lys Asn Leu Leu Leu Thr
         35                  40                  45

Leu Thr Val Phe Gly Val Ile Leu Gly Ala Val Cys Gly Gly Leu Leu
     50                  55                  60

Arg Leu Ala Ser Pro Ile His Pro Asp Val Val Met Leu Ile Ala Phe
 65                  70                  75                  80

Pro Gly Asp Ile Leu Met Arg Met Leu Lys Met Leu Ile Leu Gly Leu
                 85                  90                  95

Ile Ile Ser Ser Leu Ile Thr Gly Leu Ser Gly Leu Asp Ala Lys Ala
                100                 105                 110

Ser Gly Arg Leu Gly Thr Arg Ala Met Val Tyr Tyr Met Ser Thr Thr
            115                 120                 125

Ile Ile Ala Ala Val Leu Gly Val Ile Leu Val Leu Ala Ile His Pro
        130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
            180                 185                 190

Lys Lys Val Leu Val Ala Pro Pro Asp Glu Glu Ala Asn Ala Thr
        195                 200                 205

Ser Ala Glu Val Ser Leu Leu Asn Glu Thr Val Thr Glu Val Pro Glu
    210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
        275                 280                 285

Pro Leu Gly Ile Ala Cys Leu Ile Cys Gly Lys Ile Ile Ala Ile Lys
    290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Leu Phe Ala Gly Ile Phe
            340                 345                 350

Gln Ala Trp Ile Thr Ala Leu Gly Thr Ala Ser Ser Ala Gly Thr Leu
        355                 360                 365

Pro Val Thr Phe Arg Cys Leu Glu Glu Asn Leu Gly Ile Asp Lys Arg
    370                 375                 380

Val Thr Arg Phe Val Leu Pro Val Gly Ala Thr Ile Asn Met Asp Gly
385                 390                 395                 400
```

```
Thr Ala Leu Tyr Glu Ala Val Ala Ala Ile Phe Ile Ala Gln Met Asn
            405                 410                 415
Gly Val Val Leu Asp Gly Gly Gln Ile Val Thr Val Ser Leu Thr Ala
            420                 425                 430
Thr Leu Ala Ser Val Gly Ala Ala Ser Ile Pro Ser Ala Gly Leu Val
            435                 440                 445
Thr Met Leu Leu Ile Leu Thr Ala Val Gly Leu Pro Thr Glu Asp Ile
            450                 455                 460
Ser Leu Leu Val Ala Val Asp Trp Leu Leu Asp Arg Met Arg Thr Ser
465                 470                 475                 480
Val Asn Val Val Gly Asp Ser Phe Gly Ala Gly Ile Val Tyr His Leu
            485                 490                 495
Ser Lys Ser Glu Leu Asp Thr Ile Asp Ser Gln His Arg Val His Glu
            500                 505                 510
Asp Ile Glu Met Thr Lys Thr Gln Ser Ile Tyr Asp Asp Met Lys Asn
            515                 520                 525
His Arg Glu Ser Asn Ser Asn Gln Cys Val Tyr Ala Ala His Asn Ser
            530                 535                 540
Val Ile Val Asp Glu Cys Lys Val Thr Leu Ala Ala Asn Gly Lys Ser
545                 550                 555                 560
Ala Asp Cys Ser Val Glu Glu Glu Pro Trp Lys Arg Glu Lys
            565                 570

(2) INFORMATION FOR SEQ ID NO:8:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..15

(ix) FEATURE:
        (A) NAME/KEY: CDS
        (B) LOCATION: 16..1590

(ix) FEATURE:
        (A) NAME/KEY: 3'UTR
        (B) LOCATION: 1591..1674

(xi) SEQUENCE DESCRIPTION: SEQ ID NO:8:

ATAGCGGCGA CAGCC ATG GGG AAA CCG GCG AGG AAA GGA TGC CCG AGT TGG         51
                Met Gly Lys Pro Ala Arg Lys Gly Cys Pro Ser Trp
                  1               5                  10

AAG CGC TTC CTG AAG AAT AAC TGG GTG TTG CTG TCC ACC GTG GCC GCG         99
Lys Arg Phe Leu Lys Asn Asn Trp Val Leu Leu Ser Thr Val Ala Ala
            15                  20                  25

GTG GTG CTA GGC ATT ACC ACA GGA GTC TTG GTT CGA GAA CAC AGC AAC        147
Val Val Leu Gly Ile Thr Thr Gly Val Leu Val Arg Glu His Ser Asn
        30                  35                  40

CTC TCA ACT CTA GAG AAA TTC TAC TTT GCT TTT CCT GGA GAA ATT CTA        195
Leu Ser Thr Leu Glu Lys Phe Tyr Phe Ala Phe Pro Gly Glu Ile Leu
45                  50                  55                  60

ATG CGG ATG CTG AAA CTC ATC ATT TTG CCA TTA ATT ATA TCC AGC ATG        243
Met Arg Met Leu Lys Leu Ile Ile Leu Pro Leu Ile Ile Ser Ser Met
            65                  70                  75
```

```
ATT ACA GGT GTT GCT GCA CTG GAT TCC AAC GTA TCC GGA AAA ATT GGT      291
Ile Thr Gly Val Ala Ala Leu Asp Ser Asn Val Ser Gly Lys Ile Gly
        80                      85                      90

CTG CGC GCT GTC GTG TAT TAT TTC TGT ACC ACT CTC ATT GCT GTT ATT      339
Leu Arg Ala Val Val Tyr Tyr Phe Cys Thr Thr Leu Ile Ala Val Ile
        95                     100                     105

CTA GGT ATT GTG CTG GTG GTG AGC ATC AAG CCT GGT GTC ACC CAG AAA      387
Leu Gly Ile Val Leu Val Val Ser Ile Lys Pro Gly Val Thr Gln Lys
    110                     115                     120

GTG GGT GAA ATT GCG AGG ACA GGC AGC ACC CCT GAA GTC AGT ACG GTG      435
Val Gly Glu Ile Ala Arg Thr Gly Ser Thr Pro Glu Val Ser Thr Val
125                     130                     135                 140

GAT GCC ATG TTA GAT CTC ATC AGG AAT ATG TTC CCT GAG AAT CTT GTC      483
Asp Ala Met Leu Asp Leu Ile Arg Asn Met Phe Pro Glu Asn Leu Val
                145                     150                     155

CAG GCC TGT TTT CAG CAG TAC AAA ACT AAG CGT GAA GAA GTG AAG CCT      531
Gln Ala Cys Phe Gln Gln Tyr Lys Thr Lys Arg Glu Glu Val Lys Pro
            160                     165                     170

CCC AGC GAT CCA GAG ATG AAC ATG ACA GAA GAG TCC TTC ACA GCT GTC      579
Pro Ser Asp Pro Glu Met Asn Met Thr Glu Glu Ser Phe Thr Ala Val
        175                     180                     185

ATG ACA ACT GCA ATT TCC AAG AAC AAA ACA AAG GAA TAC AAA ATT GTT      627
Met Thr Thr Ala Ile Ser Lys Asn Lys Thr Lys Glu Tyr Lys Ile Val
        190                     195                     200

GGC ATG TAT TCA GAT GGC ATA AAC GTC CTG GGC TTG ATT GTC TTT TGC      675
Gly Met Tyr Ser Asp Gly Ile Asn Val Leu Gly Leu Ile Val Phe Cys
205                     210                     215                 220

CTT GTC TTT GGA CTT GTC ATT GGA AAA ATG GGA GAA AAG GGA CAA ATT      723
Leu Val Phe Gly Leu Val Ile Gly Lys Met Gly Glu Lys Gly Gln Ile
                225                     230                     235

CTG GTG GAT TTC TTC AAT GCT TTG AGT GAT GCA ACC ATG AAA ATC GTT      771
Leu Val Asp Phe Phe Asn Ala Leu Ser Asp Ala Thr Met Lys Ile Val
            240                     245                     250

CAG ATC ATC ATG TGT TAT ATG CCA CTA GGT ATT TTG TTC CTG ATT GCT      819
Gln Ile Ile Met Cys Tyr Met Pro Leu Gly Ile Leu Phe Leu Ile Ala
        255                     260                     265

GGG AAG ATC ATA GAA GTT GAA GAC TGG GAA ATA TTC CGC AAG CTG GGC      867
Gly Lys Ile Ile Glu Val Glu Asp Trp Glu Ile Phe Arg Lys Leu Gly
        270                     275                     280

CTT TAC ATG GCC ACA GTC CTG ACT GGG CTT GCA ATC CAC TCC ATT GTA      915
Leu Tyr Met Ala Thr Val Leu Thr Gly Leu Ala Ile His Ser Ile Val
285                     290                     295                 300

ATT CTC CCG CTG ATA TAT TTC ATA GTC GTA CGA AAG AAC CCT TTC CGA      963
Ile Leu Pro Leu Ile Tyr Phe Ile Val Val Arg Lys Asn Pro Phe Arg
                305                     310                     315

TTT GCC ATG GGA ATG GCC CAG GCT CTC CTG ACA GCT CTC ATG ATC TCT     1011
Phe Ala Met Gly Met Ala Gln Ala Leu Leu Thr Ala Leu Met Ile Ser
            320                     325                     330

TCC AGT TCA GCA ACA CTG CCT GTC ACC TTC CGC TGT GCT GAA GAA AAT     1059
Ser Ser Ser Ala Thr Leu Pro Val Thr Phe Arg Cys Ala Glu Glu Asn
        335                     340                     345

AAC CAG GTG GAC AAG AGG ATC ACT CGA TTC GTG TTA CCC GTT GGT GCA     1107
Asn Gln Val Asp Lys Arg Ile Thr Arg Phe Val Leu Pro Val Gly Ala
        350                     355                     360

ACA ATC AAC ATG GAT GGG ACC GCG CTC TAT GAA GCA GTG GCA GCG GTG     1155
Thr Ile Asn Met Asp Gly Thr Ala Leu Tyr Glu Ala Val Ala Ala Val
365                     370                     375                 380

TTT ATT GCA CAG TTG AAT GAC CTG GAC TTG GGC ATT GGG CAG ATC ATC     1203
Phe Ile Ala Gln Leu Asn Asp Leu Asp Leu Gly Ile Gly Gln Ile Ile
                385                     390                     395
```

-continued

```
ACC ATC AGT ATC ACG GCC ACA TCT GCC AGC ATC GGA GCT GCT GGC GTG         1251
Thr Ile Ser Ile Thr Ala Thr Ser Ala Ser Ile Gly Ala Ala Gly Val
            400                 405                 410

CCC CAG GCT GGC CTG GTG ACC ATG GTG ATT GTG CTG AGT GCC GTG GGC         1299
Pro Gln Ala Gly Leu Val Thr Met Val Ile Val Leu Ser Ala Val Gly
            415                 420                 425

CTG CCC GCC GAG GAT GTC ACC CTG ATC ATT GCT GTC GAC TGG CTC CTG         1347
Leu Pro Ala Glu Asp Val Thr Leu Ile Ile Ala Val Asp Trp Leu Leu
            430                 435                 440

GAC CGG TTC AGG ACC ATG GTC AAC GTC CTT GGT GAT GCT TTT GGG ACG         1395
Asp Arg Phe Arg Thr Met Val Asn Val Leu Gly Asp Ala Phe Gly Thr
445                 450                 455                 460

GGC ATT GTG GAA AAG CTC TCC AAG AAG GAG CTG GAG CAG ATG GAT GTT         1443
Gly Ile Val Glu Lys Leu Ser Lys Lys Glu Leu Glu Gln Met Asp Val
            465                 470                 475

TCA TCT GAA GTC AAC ATT GTG AAT CCC TTT GCC TTG GAA TCC ACA ATC         1491
Ser Ser Glu Val Asn Ile Val Asn Pro Phe Ala Leu Glu Ser Thr Ile
            480                 485                 490

CTT GAC AAC GAA GAC TCA GAC ACC AAG AAG TCT TAT GTC AAT GGA GGC         1539
Leu Asp Asn Glu Asp Ser Asp Thr Lys Lys Ser Tyr Val Asn Gly Gly
            495                 500                 505

TTT GCA GTA GAC AAG TCT GAC ACC ATC TCA TTC ACC CAG ACC TCA CAG         1587
Phe Ala Val Asp Lys Ser Asp Thr Ile Ser Phe Thr Gln Thr Ser Gln
            510                 515                 520

TTC TAGGGCCCCT GGCTGCAGAT GACTGGAAAC AAGGAAGGAC ATTTCGTGAG              1640
Phe

525

AGTCATCTCA AACACGGCTT AAGGAAAAGA GAAA                                   1674
```

(2) INFORMATION FOR SEQ ID NO:9:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:9:

```
Met Gly Lys Pro Ala Arg Lys Gly Cys Pro Ser Trp Lys Arg Phe Leu
 1               5                   10                  15

Lys Asn Asn Trp Val Leu Leu Ser Thr Val Ala Ala Val Val Leu Gly
                20                  25                  30

Ile Thr Thr Gly Val Leu Val Arg Glu His Ser Asn Leu Ser Thr Leu
            35                  40                  45

Glu Lys Phe Tyr Phe Ala Phe Pro Gly Glu Ile Leu Met Arg Met Leu
        50                  55                  60

Lys Leu Ile Ile Leu Pro Leu Ile Ile Ser Ser Met Ile Thr Gly Val
65                  70                  75                  80

Ala Ala Leu Asp Ser Asn Val Ser Gly Lys Ile Gly Leu Arg Ala Val
                85                  90                  95

Val Tyr Tyr Phe Cys Thr Thr Leu Ile Ala Val Ile Leu Gly Ile Val
            100                 105                 110

Leu Val Val Ser Ile Lys Pro Gly Val Thr Gln Lys Val Gly Glu Ile
            115                 120                 125

Ala Arg Thr Gly Ser Thr Pro Glu Val Ser Thr Val Asp Ala Met Leu
            130                 135                 140
```

Asp Leu Ile Arg Asn Met Phe Pro Glu Asn Leu Val Gln Ala Cys Phe
145                 150                 155                 160

Gln Gln Tyr Lys Thr Lys Arg Glu Val Lys Pro Pro Ser Asp Pro
            165                 170                 175

Glu Met Asn Met Thr Glu Ser Phe Thr Ala Val Met Thr Thr Ala
            180                 185                 190

Ile Ser Lys Asn Lys Thr Lys Glu Tyr Lys Ile Val Gly Met Tyr Ser
            195                 200                 205

Asp Gly Ile Asn Val Leu Gly Leu Ile Val Phe Cys Leu Val Phe Gly
210                 215                 220

Leu Val Ile Gly Lys Met Gly Glu Lys Gly Gln Ile Leu Val Asp Phe
225                 230                 235                 240

Phe Asn Ala Leu Ser Asp Ala Thr Met Lys Ile Val Gln Ile Ile Met
                245                 250                 255

Cys Tyr Met Pro Leu Gly Ile Leu Phe Leu Ile Ala Gly Lys Ile Ile
                260                 265                 270

Glu Val Glu Asp Trp Glu Ile Phe Arg Lys Leu Gly Leu Tyr Met Ala
                275                 280                 285

Thr Val Leu Thr Gly Leu Ala Ile His Ser Ile Val Ile Leu Pro Leu
290                 295                 300

Ile Tyr Phe Ile Val Val Arg Lys Asn Pro Phe Arg Phe Ala Met Gly
305                 310                 315                 320

Met Ala Gln Ala Leu Leu Thr Ala Leu Met Ile Ser Ser Ser Ala
                325                 330                 335

Thr Leu Pro Val Thr Phe Arg Cys Ala Glu Glu Asn Asn Gln Val Asp
                340                 345                 350

Lys Arg Ile Thr Arg Phe Val Leu Pro Val Gly Ala Thr Ile Asn Met
                355                 360                 365

Asp Gly Thr Ala Leu Tyr Glu Ala Val Ala Ala Val Phe Ile Ala Gln
                370                 375                 380

Leu Asn Asp Leu Asp Leu Gly Ile Gly Gln Ile Ile Thr Ile Ser Ile
385                 390                 395                 400

Thr Ala Thr Ser Ala Ser Ile Gly Ala Ala Gly Val Pro Gln Ala Gly
                405                 410                 415

Leu Val Thr Met Val Ile Val Leu Ser Ala Val Gly Leu Pro Ala Glu
                420                 425                 430

Asp Val Thr Leu Ile Ile Ala Val Asp Trp Leu Leu Asp Arg Phe Arg
                435                 440                 445

Thr Met Val Asn Val Leu Gly Asp Ala Phe Gly Thr Gly Ile Val Glu
450                 455                 460

Lys Leu Ser Lys Lys Glu Leu Glu Gln Met Asp Val Ser Ser Glu Val
465                 470                 475                 480

Asn Ile Val Asn Pro Phe Ala Leu Glu Ser Thr Ile Leu Asp Asn Glu
                485                 490                 495

Asp Ser Asp Thr Lys Lys Ser Tyr Val Asn Gly Gly Phe Ala Val Asp
                500                 505                 510

Lys Ser Asp Thr Ile Ser Phe Thr Gln Thr Ser Gln Phe
                515                 520                 525

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:10:

CGCGGGTACC GCCATGGAGA AGAGCAAC                                              28

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCGTCTAGA TCACAGAACC GACTCCTTG                                             29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCGGGTACC AATATGACTA AAAGCAATG                                             29

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGTCTAGA CTACATCTTG GTTTCACTG                                             29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGGTACC ACCATGGCAT CTACGGAAG                                             29

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

-continued

```
     (xi) SEQUENCE DESCRIPTION: SEQ ID NO:15:

CGCGTCTAGA TTATTTCTCA CGTTTCCAAG                                          30

(2) INFORMATION FOR SEQ ID NO:16:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:16:

CGCGGGTACC GCCATGGGGA AACCGGCG                                            28

(2) INFORMATION FOR SEQ ID NO:17:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:17:

CGCGGGATCC CTAGAACTGT GAGGTCTG                                            28
```